United States Patent [19]
Presta et al.

[11] Patent Number: 5,877,016
[45] Date of Patent: Mar. 2, 1999

[54] HUMAN TRK RECEPTORS AND NEUROTROPHIC FACTOR INHIBITORS

[75] Inventors: Leonard G. Presta, San Francisco; David L. Shelton; Roman Urfer, both of Pacifica, all of Calif.

[73] Assignee: Genentech, Inc., South San Francisco, Calif.

[21] Appl. No.: 286,846

[22] Filed: Aug. 5, 1994

Related U.S. Application Data

[63] Continuation-in-part of Ser. No. 215,139, Mar. 18, 1994, abandoned.
[51] Int. Cl.$^6$ .............................. C12H 5/00; C07K 16/00; C07H 21/04
[52] U.S. Cl. .................... 435/325; 435/320.1; 435/69.1; 536/23.4; 530/387.3; 530/388.22
[58] Field of Search .................................. 536/23.1, 23.4; 435/320.1, 240.1, 69.1; 530/388.22, 387.3

[56] References Cited

FOREIGN PATENT DOCUMENTS

| | | | |
|---|---|---|---|
| 455460 | 11/1991 | European Pat. Off. | ........ C12N 15/12 |
| 522530 | 1/1993 | European Pat. Off. | ........ C12N 15/12 |

OTHER PUBLICATIONS

Lamballe eta l. 1991. Cell 66:967–979.
Barde et al., "Purification of a new neurotrophic factor from mammalian brain" *EMBO Journal* 1(5): 549–553 (1982).
Berkmeier et al., "Neurotrophin–5: A Novel Neurtrophic Factor That Activates trk and trkB" *Neuron* 7:857–866 (Nov. 1991).
Davies et al., "p75–Deficient Trigeminal Sensory Neurons Have an Altered Response to NGF but Not to Other Neurotrophins" *Neuron* 11:565–574 (Oct. 1993).
Ernfors et al., "Molecular cloning and neurotrophic activities of a protein with structural similarities to nerve growth factor: Developmental and topographical expression in the brain" *Proc. Natl. Acad. Sci. USA* 87:5454–5458 (Jul. 1990).
Hallbook et al., "Evolutionary Studies of the Nerve Growth Factor Family Reveal a Novel Member Abundantly Expressed in Xenopus Ovary" *Neuron* 6:845–858 (May 1991).
Herrmann et al., "Mediation of NGF–stimulated Extracellular Matrix Invasion by the Human Melanoma Low–affinity p75 Neurotrophin Receptor: Melanoma p75 Functions Independently of trkA" *Mol. Biol. Cell* 4:1205–1216 (Nov. 1993).
Hohn et al., "Identification and characterization of a novel member of the nerve growth factor/brain–derived neurotrophic factor family" *Nature* 344:339–341 (Mar. 22, 1990).
Ibanez et al., "Disruption of the Low Affinity Receptor–Binding Site in NGF Allows Neuronal Survival and Differentiation by Binding to the trk Gene Product" *Cell* 69:329–341 (Apr. 17, 1992).
Ip et al., "Mammalian neurotrophin–4: Structure, chromosomal localization, tissue distribution, and receptor specificity" *Proc. Nat. Acad. Sci. USA* 89:3060–3064 (Apr. 1992).

Jones et al., "Molecular cloning of a human gene that is a member of the nerve growth factor family" *Proc. Natl. Acad. Sci. USA* 87:8060–8064 (1990).
Kaisho et al., "Cloning and expression of a cDNA encoding a novel human neurotrophic factor" *FEBS Letters* 266(1, 2):187–191 (Jun. 1990).
Klein et al., "The trkB Tyrosine Protein Kinase Is a Receptor for Brain–Derived Neurotrophic Factor and Neurotrophin–3" *Cell* 66:395–403 (Jul. 26, 1991).
Klein et al., "trkB, a novel tyrosine protein kinase receptor expressed during mouse neural development" *EMBO Journal* 8(12) :3701–3709 (1989).
Lamballe et al., "trkC, a New Member of the trk Family of Tyrosine Protein Kinases, Is a Receptor for Neurotrophin–3" *Cell* 66:967–979 (Sep. 6, 1991).
Leibrock et al., "Molecular cloning and expression of brain–derived neurotrophic factor" *Nature* 341:149–152 (Sep. 14, 1989).
Levi–Montalcini et al., "Nerve Growth Factor" *Physiol. Rev.* 48(3) :535–569 (Jul. 1968).
Maisonpierre et al., "Neurotrophin–3: A Neurotrophic Factor Related to NGF and BDNF" *Science* 247:1446–1451 (Mar. 23, 1990).
Meakin et al., "The nerve growth factor family of receptors" *TINS* 15 (9) :323–331 (1992).
Middlemas et al., "trkB a Neural Receptor Protein–Tyrosine Kinase: Evidence for a Full–Length and Two Truncated Receptors" *Molecular & Cellular Biology* 11(1):143–153 (Jan. 1991).
Rabizadeh et al., "Induction of Apoptosis by the Low–Affinity NGF Receptor" *Science* 261:345–348 (Jul. 16, 1993).
Rodriguez–Tebar et al., "Binding of neurotrophin–3 to its neuronal receptors and interactions with nerve growth factor and brain–derived neurotrophic factor" *EMBO Journal* 11(3):917–922 (1992).
Rosenthal et al., "Primary Structure and Biological Activity of a Novel Human Neurotrophic Factor" *Neuron* 4:767–773 (May 1990).
Squinto et al., "trkB Encodes a Functional Receptor for Brain–Derived Neurotrophic Factor and Neurotrophin–3 but Not Nerve Growth Factor" *Cell* 65:885–893 (May 31, 1991).
Thoenen et al., "The Physiological Function of Nerve Growth Factor in the Central Nervous System: Comparison With the Periphery" *Rev. Physiol. Biochem. Pharmacol.* 109:146–178 (1987).
Allen et al., "Cloning of a Non–catalytic Form of Human trkB and Distribution of Messenger RNA for trkB in Human Brain" *Neuroscience* 60(3) :825–834 (1994).

(List continued on next page.)

*Primary Examiner*—Lila Feisee
*Assistant Examiner*—Minh-Tam Davis
*Attorney, Agent, or Firm*—Timothy E. Torchia

[57] ABSTRACT

The invention concerns human trkB and trkC receptors and their functional derivatives. The invention further concerns inmunoadhesins comprising trk receptor sequences fused to immunoglobulin sequences.

18 Claims, 28 Drawing Sheets

OTHER PUBLICATIONS

Dawbarn et al., "Cloning of a Human trkB Gene and Distribution in Human Brain by in situ Hybridization" *British Journal of Pharmacology* (*Proceedings Supplement*) 111 (1994), 308p.

Eager, "Molecular Characterization of Human trk Proto–oncogene Product Monoclonal Antibodies" *Oncogene* 6:819–824 (1991).

Marks, "Expression and Characterization of Hepatocyte Growth Factor Receptor–IgG Fusion Proteins" *The Journal of Biological Chemistry* 267(36):26166–26171 (1992).

McGregor et al., "Molecular Cloning of the cDNA for Human trkC (NTRK3), Chromosomal Assignment, and Evidence for a Splice Variant" *Genomics* 22:267–272 (1994).

Shelton et al., "Molecular Cloning and Expression of Human trk trkB, and trkC" *Society for Neuroscience, Abstracts* 19(1–3) :1301 (1993).

Watson et al. (1990) J. Cell Biol. 110: 2221–2229.

```
1511 TTTGTTTTGTTTCATAAGATCCCACTGGATGGGTAGCTGAAATAAAGGAAAGACAGAGAAAGACAGAGAAAGGGGCTGTGCTGCTTGTTGTTGATGCTGCCATGTAAGCTGACTCCTGGACTGCT
 436  F  V  L  F  H  K  I  P  L  D  D  G  Q

1631 GTTGGCTTATCCCGGGAAGTGCTGCTTATCTGGGGTTTCTGGTAGATGTGGGCGGTGTGTTTGGAGGCTGCTACTATATGAAGCCTGCATATACTGTGAGCTGTGATTGGGAACACCAATG

1751 CAGAGGTAACTCTCAGGCAGCTAAGCAGCACCTCAAGAAACATGTTAAATTAATGCTTCTCTTCTTACAGTAGTTCAAATACAAAACTGAAATGAAATCCCATTGATTGTACTTCTCT

```
1600 TGGGTCTTTTCAAACATAGAATCATGGGATATTAAACTTGAAGGACAATAGAGATCATCTAGTCCATCAACTCACTATATATGAGGAACCTGAGTCGGGAAGTGTCT
 498  W V F S N I D N H G I L N L K D N R D H L V P S T H Y I Y E E P E V Q S G E V S

1720 TACCCAAGTCACATGGTTTCAGAGAATTATGCATGTTGAATCCAATAAGCCTTCCCGACATTCCAAGCCTCTTAACCATGGCATCTATGTTGAGGATGTCAATGTTTATTTCAGCAAAGGA
 538  Y P R S H G F R E I M L N P I S L P G H S K P L N H G I Y V E D V N V Y F S K G

1840 CGTCATGGCTTTTAAAAAC
 578  R H G F Q
```

FIG. 2C

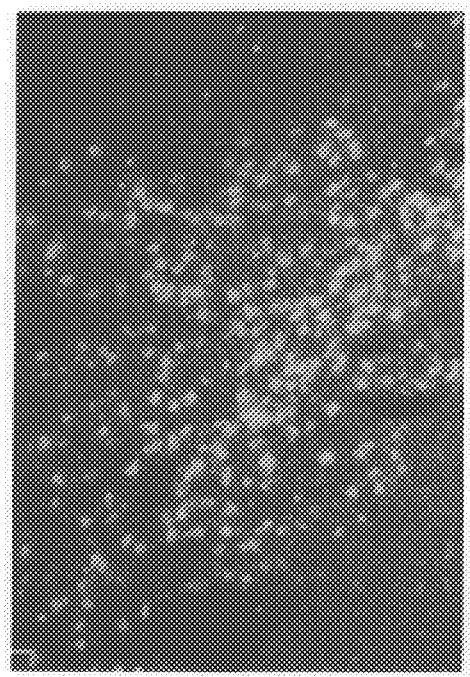 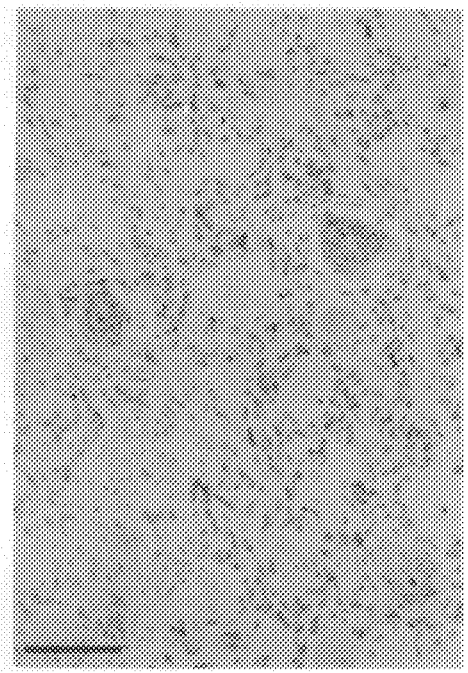
FIG. 9A　　　　　FIG. 9B
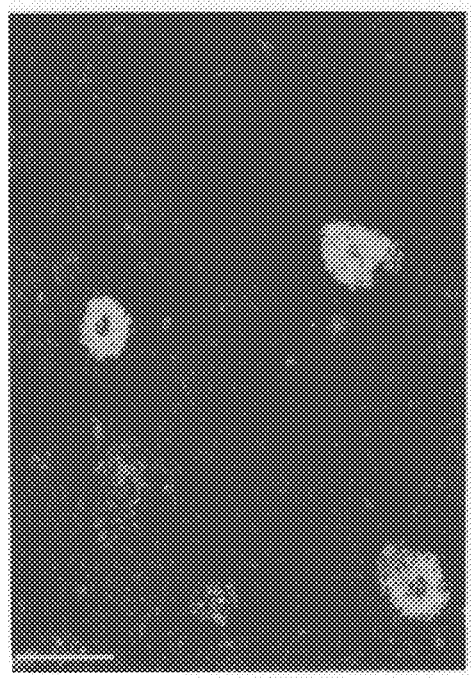 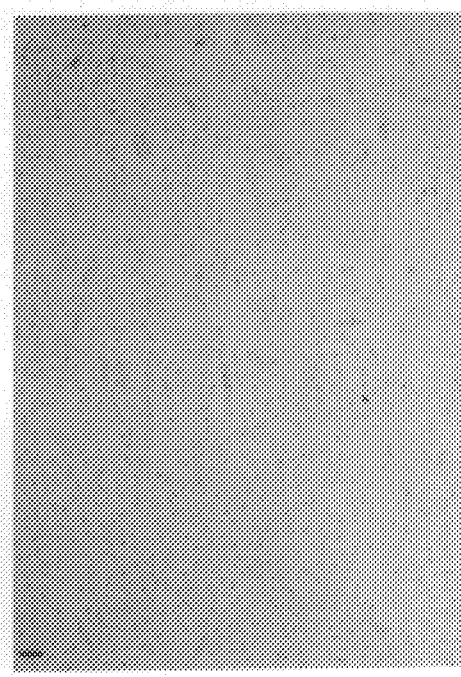
FIG. 9C　　　　　FIG. 9D

```
                  Tyrosine Kinase
trkA  532  KHLVAVKALKEASESARODFOREAELLTMLOHOHIVRFFGVCTEGRP
trkB  566  KILVAVKTLKDASDNARKDFHREAELLTNLOHEHIVKFYGVCVEGDP
trkC  566  KHLVAVKALKDPTLAARKDFOREAELLTNLOHEHIVKFYGVCGDGDP LLHVFEYHRHGDLNRFLRSHGPDAKLLAGGEDY-APGPLGLGOLLAVASOVAA
           LIHVFEYHKHGDLNKFLRAHGPDAVLHAEGNPP---TELTOSOMLHIAOOIAA
           LIHVFEYHKHGDLNKFLRAHGPDAMILVDGOPROAKGELGLSOMLHIASOIAS trkA  631  GHVYLAGLHFVHRDLATRNCLVGOGLVVKIGDFGHSRDIYSTDYYR-
trkB  663  GHVYLASOHFVHRDLATRNCLVGENLLVKIGDFGHSRDVYSTDYYR-
trkC  666  GHVYLASOHFVHRDLATRNCLVGANLLVKIGDFGHSRDVYSTDYYRL

- - - - - - VGGRTMLPIRWMPPESILYRKFTTESDVWSFGVVLWEIFT
           - - - - - - VGGHTMLPIRWMPPESIMYRKFTTESDVWSLGVVLWEIFT
           FNPSGNDFCIWCEVGGHTMLPIRWMPPESIMYRKFTTESDVWSFGVILWEIFT trkA  717  YGKOPHYOLSNTEAIDCITOGRELERPRACPPEVYAIMRGCWOREPO
trkB  749  YGKOPHYOLSNNEVIECITOGRVLORPRTCPOEVYELMLGCWOREPH
trkC  786  YGKOPWFOLSNTEVIECITOGRVLERPRVCPKEVYDVMLGCWOREPO ORHSIKDVHARLOALAOAPPVYLDVLG
           MRKNIKGIHTLLONLAKASPVYLDILG
           ORLNIKEIYKILHALGKATPIYLDILG
```

FIG. 16C

HUMAN TRK RECEPTORS AND NEUROTROPHIC FACTOR INHIBITORS

This application is a continuation-in-part of copending application Serial No. 08/215,139 filed 18 Mar. 1994, now abandoned.

FIELD OF THE INVENTION

This invention concerns human trk receptors. The invention further concerns neurotrophic factor inhibitors, and methods for inhibiting neurotrophic factor biological activity.

BACKGROUND OF THE INVENTION

Neurotrophic factors or neurotrophins are a family of small, basic proteins which play a crucial role in the development and maintenance of the nervous system. The first identified and probably best understood member of this family is nerve growth factor (NGF), which has prominent effects on developing sensory and sympathetic neurons of the peripheral nervous system (Levi-Montalcini, R. and Angeletti, P. U., *Physiol. Rev.* 48, 534–569 [1968]; Thoenen, H. et al., *Rev. Physiol. Biochem. Pharmacol.* 109, 145–178 [1987]). Although NGF and a number of animal homologs had been known for a long time, including a homolog from the mouse submandibular gland, the mature, active form of which is often referred to as β- or 2.5S NGF, it was not until recently that sequentially related but distinct polypeptides with similar functions were identified.

The first in line was a factor called brain-derived neurotrophic factor (BDNF), now also referred to as neurotrophin-2 (NT-2) which was cloned and sequenced by Leibrock, J. et al. (*Nature* 341, 149–152 [1989]). This factor was originally purified from pig brain (Barde, Y. A. et al., *EMBO J.* 1, 549–553 [1982]), but it was not until its cDNA was cloned and sequenced that its homology with NGF became apparent. The overall amino acid sequence identity between NGF and BNDF (NT-2) is about 50%. In view of this finding, Leibrock et al. speculated that there was no reason to think that BDNF and NGF should be the only members of a family of neurotrophic factors having in common structural and functional characteristics.

Indeed, further neurotrophic factors closely related to β-NGF and BDNF have since been discovered. Several groups identified a neurotrophic factor originally called neuronal factor (NF), and now referred to as neurotrophin-3 (NT-3) (Ernfors et al., *Proc. Natl. Acad. Sci. USA* 87, 5454–5458 (1990); Höhn et al., *Nature* 344, 339 [1990]; Maisonpierre et al., *Science* 247, 1446 [1990]; Rosenthal et al., *Neuron* 4, 767 [1990]; Jones and Reichardt, *Proc. Natl. Acad. Sci. USA* 87, 8060–8064 (1990); Kaisho et al., *FEBS Lett.* 266, 187 [1990]; copending U.S. application Ser. No. 07/494,024 filed 15 Mar. 1990). NT-3 shares about 50% of its amino acids with both β-NGF and BDNF (NT-2). Neurotrophins-4 and -5 (NT-4 and NT-5), have been recently added to the family (copending U.S. application Ser. No. 07/587,707 filed 25 Sep. 1990; Hallbook, F. et al., *Neuron* 6, 845–858 [1991]; Berkmeier, L. R. et al., *Neuron* 7, 857–866 [1991]; Ip et al., *Proc. Natl. Acad. Sci USA* 89, 3060–3064 [1992]). The mammalian molecule initially described by Berkmeier et al. supra, which was subsequently seen to be the homolog of Xenopus NT-4, is usually referred to as NT-4/5.

Neurotrophins, similarly to other polypeptide growth factors, affect their target cells through interactions with cell surface receptors. According to our current knowledge, two kinds of transmembrane glycoproteins serve as receptors for neurotrophins. Equilibrium binding studies have shown that neurotrophin-responsive neurons possess a common low molecular weight (65–80 kDa), low affinity receptor (LNGFR), also termed as p75$^{NTR}$ or p75, which binds NGF, BDNF, and NT-3 with a $K_D$ of $2 \times 10^{-9}$M, and large molecular weight (130–150 kDa), high affinity ($K_D$ in the $10^{-11}$M) receptors, which are members of the trk family of the receptor tyrosine kinases.

The first member of the trk receptor family, trkA, was initially identified as the result of an oncogenic transformation caused by the translocation of tropomyosin sequences onto its catalytic domain. Later work identified trkA as a signal transducing receptor for NGF. Subsequently, two other related receptors, mouse and rat trkB (Klein et al., *EMBO J.* 8, 3701–3709 [1989]; Middlemas et al., *Mol. Cell. Biol.* 11, 143–153 [1991]; EP 455,460 published 6 Nov. 1991) and porcine, mouse and rat trkC (Lamballe et al., *Cell* 66, 967–979 [1991]; EP 522,530 published 13 Jan. 1993), were identified as members of the trk receptor family. The structures of the trk receptors are quite similar, but alternate splicing increases the complexity of the family by giving rise to two known forms of trkA, three known forms of trkB (two without functional tyrosine kinase domains) and at least four forms of trkC (several without functional tyrosine kinase domain, and two with small inserts in the tyrosine kinase domain). This is summarized in FIG. 1.

The role of the p75 and trk receptors is controversial. It is generally accepted that trk receptor tyrosine kinases play an important role in conferring binding specificity to a particular neurotrophin, however, cell lines expressing trkA bind not only NGF but also NT-3 and NT-4/5 (but not BDNF), trkB expressing cells bind BDNF, NT-3, NT-4, and NT-4/5 (but not NGF), in contrast to trkC-expressing cells which have been reported to bind NT-3 alone (but not the other neurotrophins). Furthermore, it has been shown in model systems that the various forms of trk receptors, arising from alternate splicing events, can activate different intracellular signalling pathways, and therefore presumably mediate different physiological functions in vivo. It is unclear whether cells expressing a given trk receptor in the absence of p75 bind neurotrophins with low or high affinity (Meakin and Shooter, *Trends Neurosci.* 15, 323–331 [1992]).

Published results of studies using various cell lines are confusing and suggest that p75 is either essential or dispensable for neurotrophin responsiveness. Cell lines that express p75 alone bind NGF, BDNF, NT-3, and NT-4 with similar low affinity at equilibrium, but the binding rate constants are remarkably different. As a result, although p75-binding is a common property of all neurotrophins, it has been suggested the p75 receptor may also play a role in ligand discrimination (Rodriguez-Tebar et al., *EMBO J.* 11, 917–922 [1992]). It is unclear whether the p75 receptor alone is capable of mediating neurotrophin biological activity. While the trk receptors have been traditionally thought of as the biologically significant neurotrophic factor receptors, it has recently been demonstrated that in melanoma cells devoid of trkA expression, NGF can still elicit profound changes in biological behavior presumably through p75 (Herrmann et al., *Mol. Biol. Cell* 4, 1205–1216 [1993]). Recently, Davies et al. (*Neuron* 11, 565–574 [1993]) reported the results of studies investigating the role of p75 in mediating the survival response of embryonic neurons to neurotrophins in a model of transgenic mice carrying a null mutation in the p75 gene. They found that p75 enhances the sensitivity of NGF-dependent cutaneous sensory neurons to NGF.

Neurotrophins exhibit actions on distinct, but overlapping, sets of peripheral and central neurons. These effects range from playing a crucial role in ensuring the survival of developing neurons (NGF in sensory and sympathetic neurons) to relatively subtle effects on the morphology of neurons (NT-3 on purkinje cells). These activities have led to interest in using neurotrophins as treatments of certain neurodegenerative diseases. Neurotrophins have also been implicated in the mediation of inflammatory pain, and are overexpressed in certain types of malignancies. Accordingly, inhibitors of neurotrophin biological activity have therapeutic potentials, such as in pain medication and as chemotherapeutics in cancer treatment.

In order to better understand the role of trk and neurotrophin action in various human pathological states, it would be useful to identify and isolate human trkB and trkC proteins, and specifically, to determine which forms of trkB and trkC are expressed in the human Apart from their scientific and therapeutic potentials, such human trk receptor proteins would be useful in the purification of human neurotrophic factors, and in the diagnosis of various human pathological conditions associated with elevated or reduced levels of neurotrophins capable of binding trkB and/or trkC.

It would further be desirable to provide effective inhibitors of neurotrophic factor biological activity. Such inhibitors would be useful in the diagnosis and treatment of pathological conditions associated with neurotrophic factors.

SUMMARY OF THE INVENTION

The present invention is based on successful research resulting in the identification, cloning and sequencing of naturally-occurring forms of trkB and trkC receptors from the human, and in the determination of their expression pattern in various tissues by Northern and in situ hybridization analysis. The invention is further based on structure-function mutagenesis studies performed with human trkC receptor, which resulted in the identification of regions required for receptor binding and/or biological activity. The invention is additionally based on the experimental finding that expression of the extracellular domains of human trk receptors as immunoglobulin chimeras (immunoadhesins) leads to soluble molecules which retain the binding specificity of the corresponding native receptors and are capable of blocking the biological activity of their cognate neurotrophins.

In one aspect, the present invention relates to an isolated human trkB or trkC polypeptide selected from the group consisting of:

(a) a native sequence human trkB or trkC polypeptide,
(b) a polypeptide having at least 95% amino acid sequence identity with a native sequence human trkB or trkC polypeptide, exhibiting a biological property of a native human trkB or trkC polypeptide, and being non-immunogenic in the human, and
(c) a fragment of a polypeptide of (a) or (b) exhibiting a biological property of a native human trkB or trkC polypeptide, and being non-immunogenic in the human.

In another aspect, the invention concerns antibodies capable of specific binding any of the foregoing human trkB or trkC polypeptides, and to hybridoma cell lines producing such antibodies.

In yet another aspect, the invention concerns an isolated nucleic acid molecule comprising a nucleic acid sequence coding for a human trkB or trkC polypeptide as hereinabove defined.

In a further aspect, the invention concerns an expression vector comprising the foregoing nucleic acid molecule operably linked to control sequences recognized by a host cell transformed with the vector.

In a still further aspect, the invention concerns a host cell transformed with the foregoing expression vector.

In a different aspect, the invention concerns a method of using a nucleic acid molecule encoding a human trkB or trkC polypeptide as hereinabove defined, comprising expressing such nucleic acid molecule in a cultured host cell transformed with a vector comprising said nucleic acid molecule operably linked to control sequences recognized by the host cell transformed with the vector, and recovering the encoded polypeptide from the host cell.

The invention further concerns a method for producing a human trkB or trkC polypeptide as hereinabove defined, comprising inserting into the DNA of a cell containing nucleic acid encoding said polypeptide a transcription modulatory element in sufficient proximity and orientation to the nucleic acid molecule to influence the transcription thereof.

The invention also provides a method of determining the presence of a human trkB or trkC polypeptide, comprising hybridizing DNA encoding such polypeptide to a test sample nucleic acid and determining the presence of human trkB or trkC polypeptide DNA.

In a different aspect, the invention concerns a method of amplifying a nucleic acid test sample comprising priming a nucleic acid polymerase reaction with nucleic acid encoding a human trkB or trkC polypeptide, as defined above.

The invention further concerns an antagonist of a native human trkB or trkC polypeptide, as hereinabove defined.

In a further embodiment, the invention concerns a pharmaceutical composition comprising (a) a human trkB or trkC polypeptide as hereinabove defined, (b) an antagonist of a native human trkB or trkC polypeptide, or (c) an antibody specifically binding a polypeptide of (a) or (b), in admixture with a pharmaceutically acceptable carrier.

In yet another aspect, the invention concerns chimeric polypeptides comprising a trk receptor amino acid sequence capable of binding a native neurotrophic factor, linked to an immunoglobulin sequence. In a specific embodiment, the chimeric polypeptides are immunoadhesins comprising a fusion of a trk receptor amino acid sequence capable of binding a native neurotrophic factor, to an immunoglobulin sequence. The trk receptor is preferably human, and the fusion is preferably with an immunoglobulin constant domain sequence, more preferably with an immunoglobulin heavy chain constant domain sequence. In a particular embodiment, the association of two trk receptor-immunoglobulin heavy chain fusions (e.g., via covalent linkage by disulfide bond(s)) results in a homodimeric immunoglobulin-like structure. An immunoglobulin light chain may further be associated with one or both of the trk receptor-immunoglobulin chimeras in the disulfide-bonded dimer to yield a homotrimeric or homotetrameric structure.

In a further aspect, the invention concerns bispecific molecules comprising a trk receptor amino acid sequence capable of binding a native neurotrophic factor and a different binding sequence. In a special embodiment, such bispecific molecules are immunoadhesins comprising a fusion of a trk receptor amino acid sequence capable of binding a neurotrophic factor to an immunoglobulin sequence covalently associated with a fusion of a different binding sequence to an immunoglobulin sequence. The different binding sequence may, for example, be a different trk receptor amino acid sequence, capable of binding the same or a different neurotrophic factor, or may recognize a determinant on a cell type expressing the neurotrophic factor to which the first trk receptor amino acid sequence binds.

In a preferred embodiment, each of the binding sequences is fused to an immunoglobulin heavy chain constant domain sequence, and the two fusions are disulfide-bonded to provide a heterodimeric structure. Immunoglobulin light chains may be associated with the binding sequence-immunoglobulin constant domain fusions in one or both arms of the immunoglobulin-like molecule, to provide a disulfide-bonded heterotrimeric or heterotetrameric structure.

The invention further concerns nucleic acid encoding the chimeric chains of the foregoing mono- or bispecific-immunoadhesins or other bispecific polypeptides within the scope herein, expression vectors containing DNA encoding such molecules, transformed host cells, and methods for the production of the molecules by cultivating transformant host cells.

In a further aspect, the invention concerns a method for purifying a neurotrophic factor by adsorption on an immunoadhesin comprising the fusion of a trk receptor amino acid sequence capable of binding the neurotrophic factor to be purified to an immunoglobulin sequence. The trk receptor sequence preferably is of the same species that serves as the source of the neurotrophic factor to be purified.

In yet another aspect, the invention concerns a method for detecting a nucleic acid sequence coding for a polypeptide molecule which comprises all or part of a human trkB or trkC protein or a related nucleic acid sequence, comprising contacting the nucleic acid sequence with a detectable marker which binds specifically to at least part of the nucleic acid sequence, and detecting the marker so bound.

A method for the diagnosis of a pathological condition characterized by the over- or underexpression of a neurotrophic factor, comprising contacting a biological sample comprising said neurotrophic factor with a detectably labelled trk receptor polypeptide capable of binding said neurotrophic factor, and detecting the marker so bound.

The invention further concerns pharmaceutical compositions comprising a therapeutically or preventatively effective amount of a mono- or bispecific chimeric polypeptide as hereinabove defined, in admixture with a pharmaceutically acceptable carrier.

BRIEF DESCRIPTION OF THE DRAWINGS

FIGS. 1A–1C show the nucleotide sequence (SEQ ID NO: 1) and deduced amino acid sequence (SEQ ID NO: 2) of human trkB receptor. FIGS. 1A and 1B: The sequence of tyrosine kinase domain-containing trkB is shown with potential N-linked glycosylation sites boxed, predicted transmembrane domain underlined, and tyrosine kinase domain flanked by arrows. The site of the splice giving rise to the truncated form is indicated by a single vertical line. FIG. 1C: The sequence (SEQ ID NO: 40) of the alternately spliced truncated intracellular domain is shown. The amino acid sequence and the nucleotide sequence of the truncated form of human trkB receptor are attached as SEQ. ID. NOS: 4 and 7, respectively.

FIGS. 2A–2C show the nucleotide sequence (SEQ ID NO: 5) and amino acid sequence (SEQ ID NO: 6) of human trkC receptor. FIGS. 2A and 2B: The sequence of tyrosine kinase containing trkC is shown with potential N-linked glycosylation sites boxed, predicted transmembrane domain underlined, and tyrosine kinase domain flanked by arrows. The site of the splice giving rise to the truncated form is indicated by a single vertical line. The sequence of the potential inserts in the extracellular and tyrosine kinase domains are flanked by brackets. FIG. 2C: The sequence (SEQ ID NO: 41) of the alternately spliced truncated intracellular domain is shown. The amino acid sequence and the nucleotide sequence of the truncated human trkC receptor are attached as SEQ. ID NOS.: 8 and 7.

FIG. 7D shows hybridization pattern of trkA in a coronal section through nucleus basalis of Meynert (NBM) and the head of the caudate nucleus (CN), while FIG. 7E shows the pattern of trkC expression in a coronal section through hippocampus and adjacent cortex. All scale bars are 500 microns.

FIGS. 8A and 8D are darkfield photomicrographs of adjacent sections hybridized with probes for trkA and trk C in rostral DRG. FIGS. 8B and 8C and FIGS. 8E and 8F are brightfield and darkfield pairs of adjacent sections through lumbar DRG hybridized with trkA (FIGS. 8B and 8C) or trkC (FIGS. 8E and 8F). Note the differential distribution of trkA and TrkC expressing cells, with trkA expressing cells being more abundant in the more dorsal aspect of the developing ganglia and trkC expressing cells more prevalent in the ventral aspect.

FIGS. 9A–9F. In situ hybridization analysis of expression in areas of the adult human nervous system. FIG. 9A shows darkfield photomicrograph of hybridization with trkA probe in nucleus basalis of Meynert. FIGS. 9A and 9C are a bright and darkfield pair of paraffin section of adult DRG hybridized with TK-containing trkB. Note hybridization only over neurons, and that different neurons show different levels of hybridization. FIGS. 9D and 9E are bright and dark field pair showing hybridization pattern of TK-containing trkC in parietal cortex. Note the more intense hybridization over layer four and almost complete lack of hybridization in layer one. FIGS. 9F and 9G are bright and darkfield pair of trkC in cortex showing hybridization is largely confined to large neuron-like cell bodies.

FIG. 10A: Labelled NGF binding to trkA-IgG. FIG. 10B: Labelled BDNF bound to trkB-IgG. FIG. 10C: Labelled NT3 bound to trkC-IgG. Displacement was with cold NGF (●), cold BDNF (○), cold NT3 (■), or cold NT5 (□).

(FIG. 14A) Deletions of trkC. (FIG. 14B) Domain swaps of trkC with corresponding sequences from trkB. (FIG. 14C) Variants of Ig-domain 2 of trkC.

(FIG. 15A) Deletions of trkC. (FIG. 15B) Domain swaps of trkC with corresponding sequences from trkB. (FIG. 15C) Swap of Ig-domain 2 with sequence from trkB.

FIGS. 16A–16C. Comparison of the amino acid sequences of full length human trkA, trkB and trkC receptors. The concensus sequences are boxed; the boundaries of the various domains are marked by vertical lines (see SEQ. ID. NOS: 9, 2 and 6).

DETAILED DESCRIPTION OF THE INVENTION

A. Definitions

The terms "neurotrophin" and "neurotrophic factor" and their grammatical variants are used interchangeably, and refer to a family of polypeptides comprising nerve growth factor (NGF) and sequentially related homologs. NGF, brain-derived growth factor (BDNF, a.k.a. NT-2), neurotrophin-3 (NT-3), and neurotrophins-4 and -5 (NT-4/5) have so far been identified as members of this family.

The terms "neurotrophin" and "neurotrophic factor" include native neurotrophins of any (human or non-human) animal species, and their functional derivatives, whether purified from a native source, prepared by methods of recombinant DNA technology, or chemical synthesis, or any combination of these or other methods. "Native" or "native sequence," neurotrophic factors or neurotrophins have the amino acid sequence of a neurotrophin occurring in nature in any human or non-human animal species, including naturally-occurring truncated and variant forms, and naturally-occurring allelic variants.

The terms "trk", "trk polypeptide", "trk receptor" and their grammatical variants are used interchangeably and refer to polypeptides of the receptor tyrosine kinase superfamily, which are capable of binding at least one native neurotrophic factor. Currently identified members of this family are trkA (p140$^{trkA}$), trkB, and trkC, but the definition specifically includes polypeptides that might be identified in the future as members of this receptor family. The terms "trk", "trk polypeptide" and "trk receptor", with or without an affixed capital letter (e.g., A, B or C) designating specific members within this family, specifically include "native" or "native sequence" receptors (wherein these terms are used interchangeably) from any animal species (e.g. human, murine, rabbit, porcine, equine, etc.), including full length receptors, their truncated and variant forms, such as those arising by alternate splicing and/or insertion, and naturally-occurring allelic variants, as well as functional derivatives of such receptors.

Figure 4:
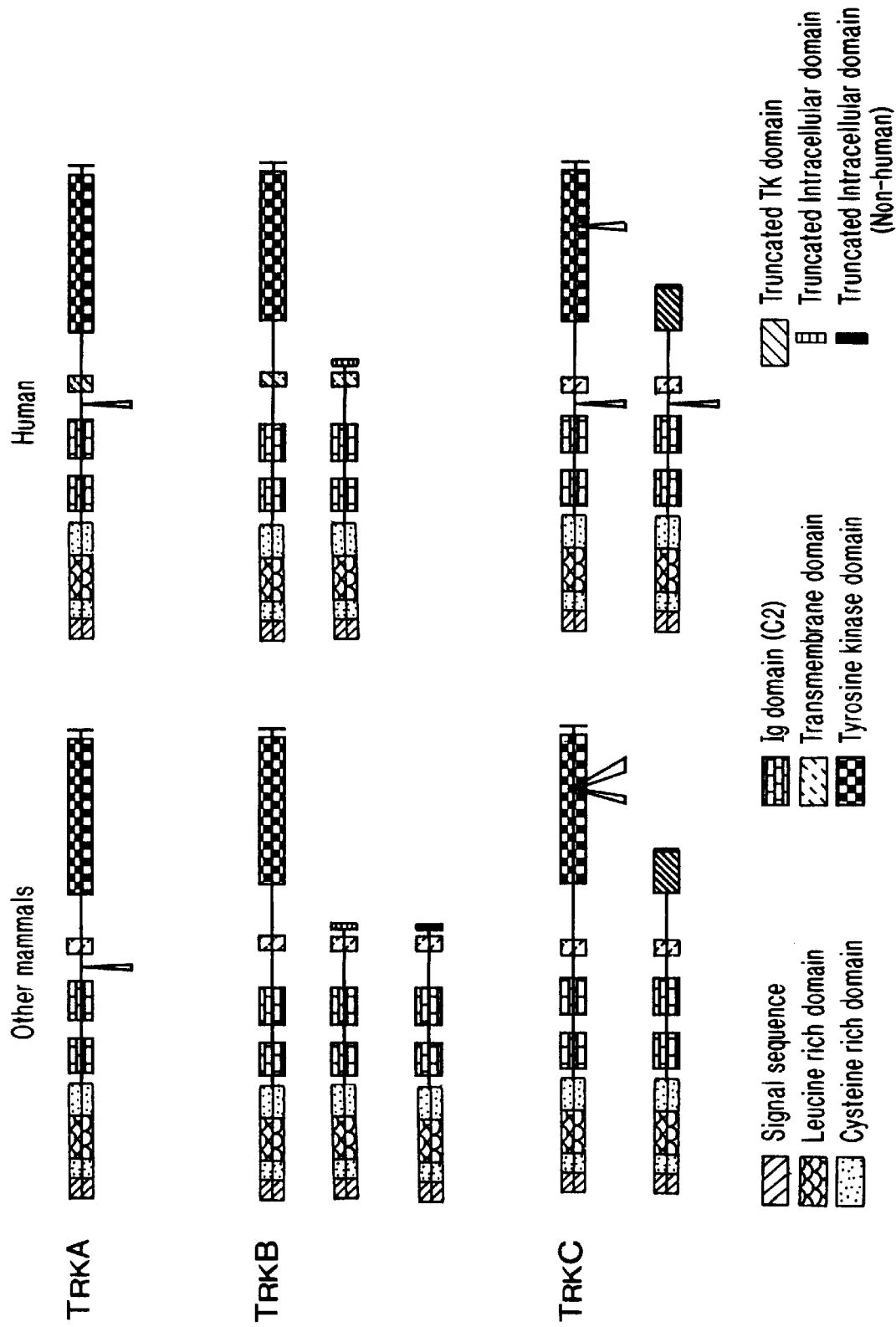
FIG. 4. Summary of the splice forms seen in human and other mammalian trks. Shown are schematic representations of the forms of the various trks arising from alternate splicing. Domains are after Schneider and Schweiger, supra. Data for is redrawn from the literature for rat trkA (Meakin, et al., *Proc. Natl. Acad. Sci. USA* 89, 2374–2378 [1992], Barker et al., *J. Biol. Chem.* 268, 15150–15157 [1993]), rat and mouse trkB (Klein, et al., *EMBO J.* 8, 3701–3709 [1989]; Klein et al., *Cell* 61, 647–656 [1990], Middlemas et al., *Mol. Cell. Biol.* 11, 143–153 [1991]) and rat and pig trkC (Lamballe, et al., *Cell* 66, 967–979 [1991]; Valenzuela et al., *Neuron* 10, 963–974 [1993]; Tsoulfas, et al., *Neuron* 10, 975–990 [1993]). Alternate forms of truncated rat trkC described by Valenzuela et al., supra are omitted for clarity. The closed triangle in trkA extracellular region represents the optionally present peptide Ser-Pro-Ser-Arg-Arg-Trp (SEQ ID NO: 39) as described in the text. The half-closed triangle in trkC extracellular region represents the optionally present 9 amino acid peptide ESTDNFILF (SEQ ID NO: 36) as described in the text. The smaller open triangle in trkC tyrosine kinase domain represents the optionally present 14 amino acid peptide LFNPSGNDFCIWCE (SEQ ID NO: 37), and the larger open triangle in non-human trkC tyrosine kinase domain represents the optionally present 25 or 39 amino acid peptides.

Thus, a "native" or "native sequence" human trkB or trkC polypeptide has the amino acid sequence of any form of a trkB or trkC receptor as occurring in the human, including full length native human trkB and trkC, truncated, tyrosine kinase (TK) domain-deleted (spliced) forms of full length native human trkB and trkC, and insertion variants of full length or truncated native human trkC, wherein the insert is within the TK domain or within the extracellular domain, and any further naturally-occurring human trkB or trkC polypeptides that might be identified in the future. A diagram of the different identified forms of human trk polypeptides in comparison to those found in animal species is shown in FIG. 4. Preceded by a signal sequence, the extracellular domains of full-length native trkA, trkB and trkC receptors have five functional domains, that have been defined with reference to homologous or otherwise similar structures identified in various other proteins (see FIGS. 16A–16C). The domains have been designated starting at the N-terminus of the amino acid sequence of the mature trk receptors as 1) a first cysteine-rich domain extending from amino acid position 1 to about amino acid position 32 of human trkA, from amino acid position 1 to about amino acid position 36 of human trkB, and from amino acid position 1 to about amino acid position 48 of human trkC; 2) a leucine-rich domain stretching from about amino acid 33 to about amino acid to about amino acid 104 in trkA; from about amino acid 37 to about amino acid 108 in trkB, and from about amino acid 49 to about amino acid 120 in trkC; 3) a second cysteine-rich domain from about amino acid 105 to about amino acid 157 in trkA; from about amino acid 109 to about amino acid 164 in trkB; and from about amino acid 121 to about amino acid 177 in trkC; 4) a first immunoglobulin-like domain stretching from about amino acid 176 to about amino acid 234 in trkA; from about amino acid 183 to about amino acid 239 in trkB; and from about amino acid 196 to about amino acid 257 in trkC; and 5) a second immunoglobulin-like domain extending from about amino acid 264 to about amino acid 330 in trkA; from about amino acid 270 to about amino acid 334 in trkB; and from about amino acid 288 to about amino acid 351 in trkC. The terms "native" or "native sequence" human trkB or trkC specifically include naturally occurring allelic variants of any native form of these receptors. It is noted that the amino acid at position 433 of human trkB was variously determined to be M or V; both sequences are specifically within the scope of the present invention.

A "functional derivative" of a native polypeptide is a compound having a qualitative biological property in common with the native polypeptide. A functional derivative of a neurotrophic factor is a compound that has a qualitative biological property in common with a native (human or non-human) neurotrophic factor. Similarly, a functional derivative of a trk receptor is a compound that has a qualitative biological property in common with a native (human or non-human) trk receptor. "Functional derivatives" include, but are not limited to, fragments of native polypeptides from any animal species (including humans), and derivatives of native (human and non-human) polypeptides and their fragments, provided that they have a biological activity in common with a corresponding native polypeptide. "Fragments" comprise regions within the sequence of a mature native neurotrophic factor or trk receptor polypeptide. Preferred fragments of trk receptors include at least the second immunoglobulin-like domain of a full length native or variant trk receptor.

The term "derivative" is used to define amino acid sequence and glycosylation variants, and covalent modifications of a native polypeptide, whereas the term "variant" refers to amino acid sequence and glycosylation variants within this definition.

"Biological property" in the context of the definition of "functional derivatives" is defined as either 1) immunological cross-reactivity with at least one epitope of a native polypeptide (e.g. neurotrophin or trk receptor), or 2) the possession of at least one adhesive, regulatory or effector function qualitatively in common with a native polypeptides (e.g. neurotrophin or trk receptor).

Preferably, the functional derivatives are polypeptides which have at least about 65% amino acid sequence identity, more preferably about 75% amino acid sequence identity, even more preferably at least about 85% amino acid sequence identity, most preferably at least about 95% amino acid sequence identity with a native polypeptide. In the context of the present invention, functional derivatives of native sequence human trkB or trkC polypeptides preferably show at least 95% amino acid sequence identity with their cognate native human receptors, and are not immunogenic in the human, or are fragments of native human trkB or trkC receptors or of polypeptides exhibiting at least 95% amino acid sequence identity with such native receptors, and are not immunogenic in the human. The fragments of native full length trk receptors preferably retain the domain or the domains within the extracellular domain that are required for ligand binding and/or biological activity. As discussed hereinabove, the extracellular domains of the trk family of proteins are build up by five domains: a first cysteine-rich domain, a leucine-rich domain, a second cysteine-rich domain, and two immunoglobulin-like domains. It is preferred to include in a functional derivative at least the second immunoglobulin-like domain of a native trk receptor, or a sequence exhibiting at least about 95% sequence identity with the second immunoglobulin-like domain of a native trk receptor, wherein the trk receptor preferably is trkB or trkC.

Amino acid sequence identity or homology is defined herein as the percentage of amino acid residues in the candidate sequence that are identical with the residues of a corresponding native polypeptide sequence, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology.

Immunologically cross-reactive as used herein means that the candidate (poly)peptide is capable of competitively inhibiting the qualitative biological activity of a corresponding native polypeptide having this activity with polyclonal antibodies or antisera raised against the known active molecule. Such antibodies and antisera are prepared in conventional fashion by injecting an animal such as a goat or rabbit, for example, subcutaneously with the known native neurotrophic factor or trk receptor in complete Feud's adjuvant, followed by booster intraperitoneal or subcutaneous injection in incomplete Freud's. "Isolated" nucleic acid or polypeptide in the context of the present invention is a nucleic acid or polypeptide that is identified and separated from contaminant nucleic acids or polypeptides present in the animal or human source of the nucleic acid or polypeptide. The nucleic acid or polypeptide may be labeled for diagnostic or probe purposes, using a label as described and defined further below in discussion of diagnostic assays.

The term "isolated human trkB and trkC polypeptide" and grammatical variants thereof refer to human trkB and trkC polypeptides (as hereinabove defined) separated from contaminant polypeptides present in the human or in other source from which the polypeptide is isolated, and fragments, amino acid sequence variants, glycosylation variants and derivatives of such native sequence polypeptides, provided that they retain the qualitative ability to bind at least one native neurotrophic factor, and are not immunogenic in humans. Such isolated human trkB and trkC polypeptides specifically include native sequence human trkB and trkC, including the native full-length human trkB and trkC receptors, their naturally-occurring truncated and amino acid (insertion) variants arising by alternate splicing, and naturally-occurring alleles. The amino acid sequence variants of native-sequence trkB or trkC polypeptides show at least about 95% homology, more preferably at least about 98% homology with their native counterparts, and are non-immunogenic to humans. Most preferably, the amino acid sequence variants within the definition of isolated native human trkB and trkC polypeptides preserve the entire native sequence of the tyrosine kinase domain, and the insertions found in naturally-occurring spliced human trkB or trkC polypeptides. The definition further includes fragments of the foregoing native polypeptides and their amino acid sequence variants, as well as their glycosylation variants and derivatives provided that they retain the qualitative ability to bind at least one native neurotrophic factor.

In general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

The term "glycosylation variant" is used to refer to a polypeptide having a glycosylation profile different from that of a corresponding native polypeptide. Glycosylation of polypeptides is typically either N-linked or O-linked. N-linked refers to the attachment of the carbohydrate moiety to the side of an asparagine residue. The tripeptide sequences, asparagine-X-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be involved in O-linked glycosylation. Any difference in the location and/or nature of the carbohydrate moieties present in a variant or fragment as compared to its native counterpart is within the scope herein.

The glycosylation pattern of native polypeptides can be determined by well known techniques of analytical chemistry, including HPAE chromatography [Hardy, M. R. et al., *Anal. Biochem.* 170, 54–62 (1988)], methylation analysis to determine glycosyl-linkage composition [Lindberg, B., *Meth. Enzymol.* 28. 178–195 (1972); Waeghe, T. J. et al., *Carbohydr. Res.* 123, 281–304 (1983)], NMR spectroscopy, mass spectrometry, etc.

"Covalent derivatives" include modifications of a native polypeptide or a fragment thereof with an organic proteinaceous or non-proteinaceous derivatizing agent, and post-translational modifications. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the trk receptor polypeptides of the present invention. Other post-translational modifications include hydroxylation of proline and lysine, phosphorylation of hydroxyl groups of seryl, tyrosine or threonyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)].

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the polypeptide chain. The DNA sequence thus codes for the amino acid sequence.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancer.

Nucleic acid is "operably linked" when it is placed into a functional relationship with another nucleic acid sequence. For example, DNA for a presequence or a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

In the context of the present invention the expressions "cell", "cell line", and "cell culture" are used interchangeably, and all such designations include progeny. Thus, the words "transformants" and "transformed (host) cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

An "eogenous" element is defined herein to mean nucleic acid sequence that is foreign to the cell, or homologous to the cell but in a position within the host cell nucleic acid in which the element is ordinarily not found.

Antibodies (Abs) and immunoglobulins (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chain s of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one and ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains [Clothia et al., *J. Mol. Biol.* 186, 651–663 (1985); Novotny and Haber, *Proc. Natl. Acad. Sci. USA* 82, 4592–4596 (1985)].

The variability is not evenly distributed through the variable regions of antibodies. It is concentrated in three segments called complementarity determining regions (CDRs) or hypervariable regions both in the light chain and the heavy chain variable regions. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies [see Kabat, E. A. et al., *Sequences of Proteins of Immunological Interest* National Institute of Health, Bethesda, Md. (1987)]. The constant domains are not involved directly in binding an antibody to an antigen, but exhibit various effector functions, such as participation of the antibody in antibody-dependent cellular toxicity.

Papain digestion of antibodies produces two identical antigen binding fragments, called Fab fragments, each with a single antigen binding site, and a residual "Fc" fragment, whose name reflects its ability to crystallize readily. Pepsin treatment yields an F(ab')$_2$ fragment that has two antigen combining sites and is still capable of cross-linking antigen. "Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab' fragments differ from Fab fragments by the addition of a few residues at the carboxy terminus of the heavy chain $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other, chemical couplings of antibody fragments are also known.

The light chains of antibodies (immunoglobulins) from any vertebrate species can be assigned to one of two clearly distinct types, called kappa and lambda (λ), based on the amino acid sequences of their constant domains.

Depending on the amino acid sequence of the constant region of their heavy chains, immunoglobulins can be assigned to different classes. There are five major classes of immunoglobulins: IgA, IgD, IgE, IgG and IgM, and several of these may be further divided into subclasses (isotypes), e.g. IgG-1, IgG-2, IgG-3, and IgG-4; IgA-1 and IgA-2. The heavy chain constant regions that correspond to the different classes of immunoglobulins are called α, delta, epsilon, λ, and μ, respectively. The subunit structures and three-dimensional configurations of different classes of immunoglobulins are well known. IgA-1 and IgA-2 are monomeric subclasses of IgA, which usually is in the form of dimers or larger polymers. Immunocytes in the gut produce mainly polymeric IgA (also referred to poly-IgA including dimers and higher polymers). Such poly-IgA contains a disulfide-linked polypeptide called the "joining" or "J" chain, and can be transported through the glandular epithelium together with the J-containing polymeric IgM (poly-IgM), comprising five subunits.

The term "antibody" is used in the broadest sense and specifically covers single anti-trk monoclonal antibodies (including agonist and antagonist antibodies) and anti-trk antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins.

The monoclonal antibodies herein include hybrid and recombinant antibodies produced by splicing a variable (including hypervariable) domain of an anti-trk antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. [See, e.g. Cabilly, et al., U.S. Pat. No. 4,816,567; Mage & Lamoyi, in *Monoclonal Anti-* body *Production Techniques and Applications*, pp.79–97 (Marcel Dekker, Inc., New York, 1987).]

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature* 256:495 (1975), or may be made by recombinant DNA methods [Cabilly, et al., supra].

"Humanized" forms of non-human (e.g. murine) antibodies are specific chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Hybridization is preferably performed under "stringent conditions" which means (1) employing low ionic strength and high temperature for washing, for example, 0.015 sodium chloride/0.0015M sodium citrate/0.1% sodium dodecyl sulfate at 50° C., or (2) employing during hybridization a denaturing agent, such as formamide, for example, 50% (vol/vol) formamide with 0.1% bovine serum albumin/ 0.1% Ficoll/0.1% polyvinylpyrrolidone/50 nM sodium phosphate buffer at pH 6.5 with 750 mM sodium chloride, 75 mM sodium citrate at 42° C. Another example is use of 50% formamide, 5× SSC (0.75M NaCl, 0.075M sodium citrate), 50 mM sodium phosphate (pH 6/8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2× SSC and 0.1% SDS.

B. Isolation of DNA encoding the term receptors

For the purpose of the present invention, DNA encoding a trk receptor can be obtained from any cDNA library prepared from tissue believed to possess the trk receptor mRNA and to express it at a detectable level. For example, a human brain cDNA library, such as that described in the examples, is a good source of trkB and trkC receptor cDNA. The trk receptor genes can also be obtained from a genomic library, such as a human genomic cosmic library.

Identification of trk receptor DNA is most conveniently accomplished by probing human or other mammalian cDNA or genomic libraries by labeled oligonucleotide sequences selected from known trk sequences (such as human trkA sequence, murine trkB sequence or murine or porcine trkC sequence) in accord with known criteria, among which is that the sequence should be sufficient in length and sufficiently unambiguous that false positives are minimized. Typically, a $^{32}$P-labeled oligonucleotide having about 30 to 50 bases is sufficient, particularly if the oligonucleotide contains one or more codons for methionine or tryptophan. Isolated nucleic acid will be DNA that is identified and separated from contaminant nucleic acid encoding other polypeptides from the source of nucleic acid.

An alternative means to isolate the gene encoding a trk receptor is to use polymerase chain reaction (PCR) methodology as described in U.S. Pat. No. 4,683,195, issued 28 Jul. 1987, in section 14 of Sambrook et al., *Molecular Cloning: A Laboratory Manual*, second edition, Cold Spring Harbor Laboratory Press. New York, 1989, or in Chapter 15 of *Current Protocols in Molecular Biology*, Ausubel et al. eds., Greene Publishing Associates and Wiley-Interscience 1991, and as illustrated in the examples.

Another alternative is to chemically synthesize the gene encoding a trk receptor, using one of the methods described in Engels and Uhlmann,*Agnew. Chem. Int. Ed. Engl.* 28, 716 (1989). These methods include triester, phosphite, phosphoramidite and H-phosphonate methods, PCR and other autoprimer methods, and oligonucleotide syntheses on solid supports.

C. Amino Acid Sequence Variants of a native trk receptor or receptor fragments

Amino acid sequence variants of native trk receptors and trk receptor fragments are prepared by methods known in the art by introducing appropriate nucleotide changes into a native or variant trk receptor DNA, or by in vitro synthesis of the desired polypeptide. There are two principal variables in the construction of amino acid sequence variants: the location of the mutation site and the nature of the mutation. With the exception of naturally-occurring alleles, which do not require the manipulation of the DNA sequence encoding the trk receptor, the amino acid sequence variants of trk receptor are preferably constructed by mutating the DNA, either to arrive at an allele or an amino acid sequence variant that does not occur in nature. In general, the mutations will be created within the extracellular domain of a native trk receptor. Sites or regions that appear to be important for the signal transduction of a neurotrophic factor, will be selected in in vitro studies of neurotrophin biological activity. Sites at such locations will then be modified in series, e.g. by (1) substituting first with conservative choices and then with more radical selections depending upon the results achieved, (2) deleting the target residue or residues, or (3) inserting residues of the same or different class adjacent to the located site, or combinations of options 1–3.

One helpful technique is called "alanine scanning" (Cunningham and Wells, *Science* 244, 1081–1085 [1989]). Here, a residue or group of target residues is identified and substituted by alanine or polyalanine. Those domains demonstrating functional sensitivity to the alanine substitutions are then refined by introducing further or other substituents at or for the sites of alanine substitution.

After identifying the desired mutation(s), the gene encoding a trk receptor variant can be obtained by chemical synthesis as hereinabove described.

More preferably, DNA encoding an trk receptor amino acid sequence variant is prepared by site-directed mutagenesis of DNA that encodes an earlier prepared variant or a nonvariant version of trk receptor. Site-directed (site-specific) mutagenesis allows the production of trk receptor variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the techniques of site-specific mutagenesis are well known in the art, as exemplified by publications such as, Edelman et al., *DNA 2*, 183 (1983). As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, A. Walton, ed., Elsevier, Amsterdam (1981). This and other phage vectors are commercially available and their use is well known to those skilled in the art. A versatile and efficient procedure for the construction of oligodeoxyribonucleotide directed site-specific mutations in DNA fragments using M13-derived vectors was published by Zoller, M. J. and Smith, M., *Nucleic Acids Res.* 10, 6487–6500 [1982]). Also, plasmid vectors that contain a single-stranded phage origin of replication (Veira et al., *Meth. Enzymol. 153, 3* [*1987*]) may be employed to obtain single-stranded DNA. Alternatively, nucleotide substitutions are introduced by synthesizing the appropriate DNA fragment in vitro, and amplifying it by PCR procedures known in the art.

In general, site-specific mutagenesis herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. USA* 75, 5765 (1978). This primer is then annealed with the single-stranded protein sequence-containing vector, and subjected to DNA-polymerizing enzymes such as, *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate host cells such as JP101 cells, and clones are selected that include recombinant vectors bearing the mutated sequence arrangement. Thereafter, the mutated region may be removed and placed in an appropriate expression vector for protein production.

The PCR technique may also be used in creating amino acid sequence variants of a trk receptor. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more) part ligation.

In a specific example of PCR mutagenesis, template plasmid DNA (1 $\mu$g) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp® kits (obtained from Perkin-Elmer Cetus, Norwalk, Conn. and Emeryville, Calif.), and 25 pmole of each oligonucleotide primer, to a final volume of 50 $\mu$l. The reaction mixture is overlayered with 35 $\mu$l mineral oil. The reaction is denatured for 5 minutes at 100° C., placed briefly on ice, and then 1 $\mu$l Thermus aquaticus (TaG) DNA polymerase (5 units/l), purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus) programmed as follows:

2 min. 55° C., 30 sec. 72° C., then 19 cycles of the following:

30 sec. 94° C., 30 sec. 55° C., and 30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to appropriate treatments for insertion into a vector.

Another method for preparing variants, cassette mutagenesis, is based on the technique described by Wells et al. [*Gene* 34, 315 (1985)]. The starting material is the plasmid (or vector) comprising the trk receptor DNA to be mutated. The codon(s) within the trk receptor to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the trk receptor DNA. After the restriction sites have been introduced into the plasmid, the plasmid is cut at these sites to linearize it. A double-stranded oligonucleotide encoding the sequence of the DNA between the restriction site but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated trk receptor DNA sequence.

Additionally, the so-called phagemid display method may be useful in making amino acid sequence variants of native or variant trk receptors or their fragments. This method involves (a) constructing a replicable expression vector comprising a first gene encoding an receptor to be mutated, a second gene encoding at least a portion of a natural or wild-type phage coat protein wherein the first and second genes are heterologous, and a transcription regulatory element operably linked to the first and second genes, thereby forming a gene fusion encoding a fusion protein; (b) mutating the vector at one or more selected positions within the first gene thereby forming a family of related plasmids; (c) transforming suitable host cells with the plasmids; (d) infecting the transformed host cells with a helper phage having a gene encoding the phage coat protein; (e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; (f) contacting the phagemid particles with a suitable antigen so that at least a portion of the phagemid particles bind to the antigen; and (g) separating the phagemid particles that bind from those that do not. Steps (d) through (g) can be repeated one or more times. Preferably in this method the plasmid is under tight control of the transcription regulatory element, and the culturing conditions are adjusted so that the amount or number of phagemid particles displaying more than one copy of the fusion protein on the surface of the particle is less than about 1%. Also, preferably, the amount of phagemid particles displaying more than one copy of the fusion protein is less than 10% of the amount of phagemid particles displaying a single copy of the fusion protein. Most preferably, the amount is less than 20%. Typically in this method, the expression vector will further contain a secretory signal sequence fused to the DNA encoding each subunit of the polypeptide and the transcription regulatory element will be a promoter system. Preferred promoter systems are selected from lac Z, $\lambda_{PL}$, tac, T7 polymerase, tryptophan, and alkaline phosphatase promoters and combinations thereof. Also, normally the method will employ a helper phage selected from M13K07, M13R408, M13-VCS, and Phi X 174. The preferred helper phage is M13K07, and the preferred coat protein is the M13 Phage gene III coat protein. The preferred host is *E. coli*, and protease-deficient strains of *E. coli*.

Further details of the foregoing and similar mutagenesis techniques are found in general textbooks, such as, for example, Sambrook et al., supra, and *Current Protocols in Molecular Biology*, Ausubel et al. eds., supra.

Amino acid substitution variants have at least one amino acid residue in a native receptor molecule removed and a different residue inserted in its place. The sites of great interest for substitutional mutagenesis include sites identified as important for signal transduction and/or ligand binding, and sites where the amino acids found in the native trk receptors from various species are substantially different in terms of side bulk, charge and/or hydrophobicity. As it will be apparent from the examples, the second immunoglobulin-like domain of the human trkC receptor has been identified as primarily responsible for neurotrophin binding. Substitutions (just as other amino acid alterations) within this region are believed to significantly affect the neurotrophin binding properties of trk receptors. Amino acid(s) primarily responsible for the binding specificity of and the diverse biological activities mediated by the individual trk receptors can be identified by a combination of the foregoing mutagenesis techniques. At least part of the amino acids distinguishing the various trk receptors from one another are believed to be within the second immunoglobulin-like domain of their extracellular region. It is possible to create trk receptor variants by substituting the region identified as responsible for ligand-specificity in one trk receptor by the ligand binding domain of another trk receptor.

Other sites of interest are those in which particular residues of the native trk receptors from various species are identical. These positions may be important for the biological function of the trk receptor. Further important sites for mutagenesis include motifs common in various members of the trk receptor family.

Naturally-occurring amino acids are divided into groups based on common side chain properties:

(1) hydrophobic: norleucine, met, ala, val, leu, ile;
(2) neutral hydrophobic: cys, ser, thr;
(3) acidic: asp, glu;
(4) basic: asn, gln, his, lys, arg;
(5) residues that influence chain orientation: gly, pro; and
(6) aromatic: trp, tyr, phe.

Conservative substitutions involve exchanging a member within one group for another member within the same group, whereas non-conservative substitutions will entail exchanging a member of one of these classes for another Variants obtained by non-conservative substitutions within the neurotrophic factor-binding region(s) of a native trk receptor sequence of a fragment thereof are expected to result in significant changes in the biological properties of the obtained variant, and may result in trk receptor variants which block the biological activity of their cognate neurotrophic factor(s), i.e. are antagonists of the biological action of the corresponding native neurotrophic factor(s), or the signaling potential of which surpasses that of the corresponding native trk receptor. Amino acid positions that are conserved among various species and/or various receptors of the trk receptor family are generally substituted in a relatively conservative manner if the goal is to retain biological activity.

Amino acid sequence deletions generally range from about 1 to 30 residues, more preferably about 1 to 10 residues, and typically are contiguous. Deletions may be introduced into regions not directly involved in signal transduction and/or ligand binding, to modify the biological activity of the trk receptor. Deletions from the regions that are directly involved in signal transduction and/or ligand binding will be more likely to modify the biological activity of the mutated trk receptor more significantly, and may potentially yield trk receptor antagonists. The number of consecutive deletions will be selected so as to preserve the tertiary structure of the trk receptor in the affected domain.

It is possible to construct trk receptor variants which combine the binding domains for and, accordingly, have the ability to signal the biological activities of more than one neurotrophic factor. Such variant can be made by inserting into the sequence of a trk receptor the neurotrophin binding domain of another trk receptor. For example, native trkB and trkC receptors do not bind to an appreciable degree NGF, which is the native ligand for the trkA receptor. Insertion of the NGF-binding sequence of a trkA receptor into a trkB or trkC receptor yields a trkB or trkC receptor variant, which (in addition to the native ligands of the native trkB and trkC receptors, respectively) binds NGF. Similarly, naturally occurring trkB receptors bind BDNF and NT4/5 but do not bind appreciably to NGF or NT-3. Thus, the insertion of the NT-3 binding sequence of trkC into a trkB receptor yields a variant receptor that is capable of binding BDNF, NT4/5 and NT-3. The resultant receptor variants will be able to mediate a broader spectrum of biological activities, which opens new ways for their application and therapeutics.

Amino acid insertions also include amino- and/or carboxyl-terminal fusions ranging in length from one residue to polypeptides containing a hundred or more residues, as well as intrasequence insertions of single or multiple amino acid residues. Intrasequence insertions (i.e. insertions within the trk receptor amino acid sequence) may range generally from about 1 to 10 residues, more preferably 1 to 5 residues, more preferably 1 to 3 residues. Examples of terminal insertions include the trk receptor with an N-terminal methionyl residue, an artifact of its direct expression in bacterial recombinant cell culture, and fusion of a heterologous N-terminal signal sequence to the N-terminus of the trk receptor molecule to facilitate the secretion of the mature trk receptor from recombinant host cells. Such signal sequences will generally be obtained from, and thus homologous to, the intended host cell species. Suitable sequences include STII or Ipp for *E. coli*, alpha factor for yeast, and viral signals such as herpes gD for mammalian cells.

Other insertional variants of the native trk receptor molecules include the fusion to the N- or C-terminus of the trk receptor of immunogenic polypeptides, e.g. bacterial polypeptides such as beta-lactamase or an enzyme encoded by the *E. coli* trp locus, or yeast protein, and C-terminal fusions with proteins having a long half-life such as immunoglobulin regions (preferably immunoglobulin constant regions), albumin, or ferritin as described in WO 89/02922 published on 6 Apr. 1989.

Since it is often difficult to predict in advance the characteristics of a variant trk receptor, it will be appreciated that some screening will be need ed to select the optimum variant.

D. Insertion of DNA into a Cloning Vehicle

Once the nucleic acid encoding a native or variant trk receptor is available, it is generally ligated into a replicable expression vector for further cloning (amplification of the DNA), or f or expression.

Expression and cloning vectors are well known in the art and contain a nucleic acid sequence that enables the vector to replicate in one or more selected host cells. The selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA of expression of DNA) and the host cell for which it is compatible. The vector components generally include, but are not limited to, one or more of the following: a signal sequence, an origin of replication, one or more marker genes, an enhancer element, a promoter, and a transcription termination sequence.

(i) Signal Sequence Component

In general, the signal sequence may be a component of the vector, or it may be a part of the trk receptor that is inserted into the vector. The native trk receptor comprises a signal sequence at the amino terminus (5' end of the DNA) of the polypeptide that is cleaved during post-translational processing of the polypeptide to form a mature trk receptor. Native trk receptor is however not secreted from the host cell as it contains a membrane anchoring domain between the extracellular domain and the cytoplasmic domain Thus, to form a secreted version of an trk receptor, the membrane anchoring domain (also referred to as transmembrane domain) is ordinarily deleted or otherwise inactivated (for example by point mutation(s)). Generally, the cytoplasmic domain is also deleted along with the membrane anchoring domain. The truncated (or transmembrane domain-inactivated) trk receptor variants may be secreted from the cell, provided that the DNA encoding the truncated variant retains the amino terminal signal sequence.

Included within the scope of this invention are trk receptors with the native signal sequence deleted and replaced with a heterologous signal sequence. The heterologous signal sequence selected should be one that is recognized and processed (i.e. cleaved by a signal peptidase) by the host cell.

For prokaryotic host cells that do not recognize and process the native trk receptor signal sequence, the signal sequence is substituted by a prokaryotic signal sequence selected, for example, from the group of the alkaline phosphatase, penicillinase, lpp, or heat-stable enterotoxin II leaders. For yeast secretion the native trk receptor signal sequence may be substituted by the yeast invertase, alpha factor, or acid phosphatase leaders. In mammalian cell expression the native signal sequence is satisfactory, although other mammalian signal sequences may be suitable.

(ii) Origin of Replication Component

Both expression and cloning vectors contain a nucleic acid sequence that enabled the vector to replicate in one or more selected host cells. Generally, in cloning vectors this sequence is one that enables the vector to replicate independently of the host chromosomes, and includes origins of replication or autonomously replicating sequences. Such sequence are well known for a variety of bacteria, yeast and viruses. The origin of replication from the well-known plasmid pBR322 is suitable for most gram negative bacteria, the $2\mu$ plasmid origin for yeast and various viral origins (SV40, polyoma, adenovirus, VSV or BPV) are useful for cloning vectors in mammalian cells. Origins of replication are not needed for mammalian expression vectors (the SV40 origin may typically be used only because it contains the early promoter). Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA is also cloned by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of the DNA encoding the desired heterologous polypeptide. However, the recovery of genomic DNA is more complex than that of an exogenously replicated vector because restriction enzyme digestion is required to excise the encoded polypeptide molecule.

(iii) Selection Gene Component

Expression and cloning vectors should contain a selection gene, also termed a selectable marker. This is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b)

complement auxotrophic deficiencies, or (c) supply critical nutrients not available from complex media, e.g. the gene encoding D-alanine racemase for bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin [Southern et al., *J. Molec. Appl. Genet.* 1, 327 (1982)], mycophenolic acid [Mulligan et al., *Science* 209, 1422 (1980)], or hygromycin [Sudgen et al., *Mol. Cel. Biol.* 5, 410–413 (1985)]. The three examples given above employ bacterial genes under eukaryotic control to convey resistance to the appropriate drug G418 or neomycin (geneticin), xgpt (mycophenolic acid), or hygromycin, respectively Other examples of suitable selectable markers for mammalian cells are dihydrofolate reductase (DHFR) or thymidine kinase. Such markers enable the identification of cells which were competent to take up the desired nucleic acid. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the desired polypeptide. Amplification is the process by which genes in greater demand for the production of a protein critical for growth are reiterated in tandem within the chromosomes of successive generations of recombinant cells. Increased quantities of the desired polypeptide (either a trk-containing chimeric polypeptide or a segment thereof) are synthesized from the amplified DNA.

For example, cells transformed with the DHFR selection gene are first identified by culturing all of the transformants in a culture medium which lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Nat'l. Acad. Sci. USA* 77, 4216 (1980). A particularly useful DHFR is a mutant DHFR that is highly resistant to MTX (EP 117,060). This selection agent can be used with any otherwise suitable host, e.g. ATCC No. CCL61 CHO-K1, notwithstanding the presence of endogenous DHFR. The DNA encoding DHFR and the desired polypeptide, respectively, then is amplified by exposure to an agent (methotrexate, or MTX) that inactivates the DHFR. One ensures that the cell requires more DHFR (and consequently amplifies all exogenous DNA) by selecting only for cells that can grow in successive rounds of ever-greater MTX concentration. Alternatively, hosts co-transformed with genes encoding the desired polypeptide, wild-type DHFR, and another selectable marker such as the neo gene can be identified using a selection agent for the selectable marker such as G418 and then selected and amplified using methotrexate in a wild-type host that contains endogenous DHFR. (See also U.S. Pat. No. 4,965,199).

A suitable selection gene for use in yeast is the trp1 gene present in the yeast plasmid YRp7 (Stinchcomb et al., 1979, *Nature* 282:39; Kingsman et al., 1979, *Gene* 7:141; or Tschemper et al., 1980, *Gene* 10:157). The trp1 gene provides a selection marker for a mutant strain of yeast lacking the ability to grow in tryptophan, for example, ATCC No. 44076 or PEP4–1 (Jones, 1977, *Genetics* 85:12). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

(iv) Promoter Component

Expression vectors, unlike cloning vectors, should contain a promoter which is recognized by the host organism and is operably linked to the nucleic acid encoding the desired polypeptide. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the desired polypeptide by removing them from their gene of origin by restriction enzyme digestion, followed by insertion 5' to the start codon for the polypeptide to be expressed. This is not to say that the genomic promoter for trk receptor is not usable. However, heterologous promoters generally will result in greater transcription and higher yields of expressed trk receptor as compared to the native trk receptor promoter.

Promoters suitable for use with prokaryotic hosts include the β-lactamase and lactose promoter systems (Chang et al., *Nature* 275:615 (1978); and Goeddel et al., *Nature* 281:544 (1979)), alkaline phosphatase, a tryptophan (trp) promoter system (Goeddel, *Nucleic Acids Res.* 8:4057 (1980) and EPO Appln. Publ. No. 36,776) and hybrid promoters such as the tac promoter (H. de Boer et al., *Proc. Nat'l. Acad. Sci. USA* 80:21–25 (1983)). However, other known bacterial promoters are suitable. Their nucleotide sequences have been published, thereby enabling a skilled worker operably to ligate them to DNA encoding trk (Siebenlist et al. *Cell* 20:269 (1980)) using linkers or adaptors to supply any required restriction sites. Promoters for use in bacterial systems also will contain a Shine-Dalgarno (S.D.) sequence operably linked to the DNA encoding trk.

Suitable promoting sequences for use with yeast hosts include the promoters for 3-phosphoglycerate kinase (Hitzeman et al. *J. Biol. Chem.* 255:2073 (1980)) or other glycolytic enzymes (Hess et al., *J. Adv. Enzyme Reg.* 7:149 (1978); and Holland, *Biochemistry* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

trk receptor transcription from vectors in mammalian host cells may be controlled by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat shock promoters, and from the promoter normally associated with the trk receptor sequence, provided such promoters are compatible with the host cell systems.

The early and late promoters of the SV40 virus are conveniently obtained as an SV40 restriction fragment which also contains the SV40 viral origin of replication [Fiers et al., Nature 273:113 (1978), Mulligan and Berg, Science 209, 1422–1427 (1980); Pavlakis et al., Proc. Natl. Acad. Sci. USA 78, 7398–7402 (1981)]. The immediate early promoter of the human cytomegalovirus is conveniently obtained as a HindIII E restriction fragment [Greenaway et al., Gene 18, 355–360 (1982)]. A system for expressing DNA in mammalian hosts using the bovine papilloma virus as a vector is disclosed in U.S. Pat. No. 4,419,446. A modification of this system is described in U.S. Pat. No. 4,601,978. See also, Gray et al., Nature 295, 503–508 (1982) on expressing cDNA encoding human immune interferon in monkey cells; Reyes et al., Nature 297, 598–601 (1982) on expressing human β-interferon cDNA in mouse cells under the control of a thymidine kinase promoter from herpes simplex virus; Canaani and Berg, Proc. Natl. Acad. Sci. USA 79, 5166–5170 (1982) on expression of the human interferon β1 gene in cultured mouse and rabbit cells; and Gorman et al., Proc. Natl. Acad. Sci. USA 79, 6777–6781 (1982) on expression of bacterial CAT sequences in CV-1 monkey kidney cells, chicken embryo fibroblasts, Chinese hamster ovary cells, HeLa cells, and mouse HIN-3T3 cells using the Rous sarcoma virus long terminal repeat as a promoter.

The actual plasmid used in the course of cloning the murine trk receptor contains the promoter of the murine 3-hydroxy-3-methylglutaryl methylglutaryl coenzyme A reductase gene [Gautier et al., Nucleic Acids Res. 17, 8389 (1989)], whereas the reporter plasmid [pUMS (GT)$_8$-Tac] used during expression cloning contained an artificial multimerized trk recepto-inducible promoter element [McDonald et al., Cell 60, 767–779 (1990)].

(v) Enhancer Element Component

Transcription of a DNA encoding the trk receptors of the present invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent having been found 5' [Laimins et al., Proc. Natl. Acad. Sci. USA 78, 993 (1981)] and 3' [Lasky et al., Mol Cel. Biol. 3, 1108 (1983)] to the transcription unit, within an intron [Banerji et al., Cell 33, 729 (1983)] as well as within the coding sequence itself [Osborne et al., Mol. Cel. Biol. 4, 1293 (1984)]. Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, Nature 297, 17–18 (1982) on enhancing elements for activation of eukaryotic promoters. The enhancer may be spliced into the vector at a position 5' or 3' to the trk receptor DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the trk receptor. The 3' untranslated regions also include transcription termination sites.

Construction of suitable vectors containing one or more of the above listed components, the desired coding and control sequences, employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform E. coli K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., Nucleic Acids Res. 9, 309 (1981) or by the method of Maxam et al., Methods in Enzymology 65, 499 (1980).

Particularly useful in the practice of this invention are expression vectors that provide for the transient expression in mammalian cells of DNA encoding an trk receptor. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient systems, comprising a suitable expression vector and a host cell, allow for the convenient positive identification of polypeptides encoded by clones DNAs, as well as for the rapid screening of such polypeptides for desired biological or physiological properties. Thus, transient expression systems are particularly useful in the invention for purposes of identifying analogs and variants of the trk receptor.

Other methods, vectors, and host cells suitable for adaptation to the synthesis of the trk receptors in recombinant vertebrate cell culture are described in Getting et al., Nature 293, 620–625 (1981); Mantel et al., Nature 281, 40–46 (1979); Levinson et al.; EP 117,060 and EP 117,058. A particularly useful plasmid for mammalian cell culture expression of the trk receptor is pRK5 (EP 307,247).

E. Selection and Transformation of Host Cells

Suitable host cells for cloning or expressing the vectors herein are the prokaryote, yeast or higher eukaryote cells described above. Suitable prokaryotes include gram negative or gram positive organisms, for example E. coli or bacilli. A preferred cloning host is E. coli 294 (ATCC 31,446) although other gram negative or gram positive prokaryotes such as E. coli B, E. coli X1776 (ATCC 31,537), E. coli W3110 (ATCC 27,325), Pseudomonas species, or Serratia Marcesans are suitable.

In addition to prokaryotes, eukaryotic microbes such as filamentous fungi or yeast are suitable hosts for vectors herein. Saccharomyces cerevisiae, or common baker's yeast, is the most commonly used among lower eukaryotic host microorganisms. However, a number of other genera, species and strains are commonly available and useful herein, such as *S. pombe* [Beach and Nurse, *Nature* 290, 140 (1981)], *Kluyveromyces lactis* [Louvencourt et al., *J. Bacteriol.* 737 (1983)]; *yarrowia* (EP 402,226); *Pichia pastoris* (EP 183,070), *Trichoderma reesia* (EP 244,234), *Neurospora crassa* [Case et al., *Proc. Natl. Acad. Sci. USA* 76, 5259–5263 (1979)]; and Aspergillus hosts such as *A. nidulans* [Ballance et al., *Biochem. Biophys. Res. Commun.* 112, 284–289 (1983); Tilburn et al., *Gene* 26, 205–221 (1983); Yelton et al., *Proc. Natl. Acad. Sci. USA* 81, 1470–1474 (1984)] and *A. niger* [Kelly and Hynes, *EMBO J.* 4, 475–479 (1985)].

Suitable host cells may also derive from multicellular organisms. Such host cells are capable of complex processing and glycosylation activities. In principle, any higher eukaryotic cell culture is workable, whether from vertebrate or invertebrate culture, although cells from mammals such as humans are preferred. Examples of invertebrate cells include plants and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melangaster* (fruitfly), and *Bombyx mori* host cells have been identified. See, e.g. Luckow et al., *Bio/Technology* 6, 47–55 (1988); Miller et al., in *Genetic Engineering*, Setlow, J. K. et al., eds., Vol. 8 (Plenum Publishing, 1986), pp. 277–279; and Maeda et al., *Nature* 315, 592–594 (1985). A variety of such viral strains are publicly available, e.g. the L-1 variant of *Autographa californica* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the trk receptor DNA. During incubation of the plant cell culture with *A. tumefaciens*, the DNA encoding trk receptor is transferred to the plant cell host such that it is transfected, and will, under appropriate conditions, express the trk receptor DNA. In addition, regulatory and signal sequences compatible with plant cells are available, such as the nopaline synthase promoter and polyadhenylation signal sequences. Depicker et al., *J. Mol. Appl. Gen.* 1, 561 (1982). In addition, DNA segments isolated from the upstream region of the T-DNA 780 gene are capable of activating or increasing transcription levels of plant-expressible genes in recombinant DNA-containing plant tissue. See EP 321,196 published 21 Jun. 1989.

However, interest has been greatest in vertebrate cells, and propagation of vertebrate cells in culture (tissue culture) is per se well known. See *Tissue Culture*, Academic Press, Kruse and Patterson, editors (1973). Examples of useful mammalian host cell lines are monkey kidney CV1 line transformed by SV40 (COS-7, ATCC CRL 1651); human embryonic kidney cell line [293 or 293 cells subcloned for growth in suspension culture, Graham et al., *J. Gen. Virol.* 36, 59 (1977)]; baby hamster kidney cells 9BHK, ATCC CCL 10); Chinese hamster ovary cells/-DHFR [CHO, Urlaub and Chasin, *Proc. Natl. Acad. Sci. USA* 77, 4216 (1980)]; mouse sertolli cells [TM4, Mather, *Biol. Reprod.* 23, 243–251 (1980)]; monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL75); human liver cells (Hep G2, HB 8065); mouse mammary tumor (MMT 060562, ATCC CCL51); TRI cells [Mather et al., *Annals N.Y. Acad. Sci.* 383, 44068 (1982)]; MRC 5 cells; FS4 cells; and a human hepatoma cell line (Hep G2). Preferred host cells are human embryonic kidney 293 and Chinese hamster ovary cells.

Particularly preferred host cells for the purpose of the present invention are vertebrate cells producing the trk receptor.

Host cells are transfected and preferably transformed with the above-described expression or cloning vectors and cultured in conventional nutrient media modified as is appropriate for inducing promoters or selecting transformants containing amplified genes.

F. Culturing the Host Cells

Prokaryotes cells used to produced the trk receptor polypeptides of this invention are cultured in suitable media as describe generally in Sambrook et al., supra.

Mammalian cells can be cultured in a variety of media. Commercially available media such as Ham's F10 (Sigma), Minimal Essential Medium (MEM, Sigma), RPMI-1640 )Sigma), and Dulbecco's Modified Eagle's Medium (DMEM, Sigma) are suitable for culturing the host cells. In addition, any of the media described in Ham and Wallace, *Meth. Enzymol.* 58, 44 (1979); Barnes and Sato, *Anal. Biochem.* 102, 255 (1980), U.S. Pat. Nos. 4,767,704; 4,657, 866; 4,927,762; or 4,560,655; WO 90/03430; WO 87/00195 or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug) trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH and the like, suitably are those previously used with the host cell selected for cloning or expression, as the case may be, and will be apparent to the ordinary artisan.

The host cells referred to in this disclosure encompass cells in in vitro cell culture as well as cells that are within a host animal or plant.

It is further envisioned that the trk receptor of this invention may be produced by homologous recombination, or with recombinant production methods utilizing control elements introduced into cells already containing DNA encoding the trk receptor.

G. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA* 77, 5201–5205 (1980)], dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as a site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to the surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hse et al., *Am. J. Clin. Pharm.* 75, 734–738 (1980).

Antibodies useful for immunohistochemical staining and/or assay of sample fluids may be either monoclonal or polyclonal, and may be prepared in any animal. Conveniently, the antibodies may be prepared against a native trk receptor polypeptide, or against a synthetic peptide based on the DNA sequence provided herein as described further hereinbelow.

H. Purification of the trk receptor

The trk receptor preferably is recovered from the cell culture medium as a secreted polypeptide, although it also may be recovered from host cell lysates when directly expressed in a form including the membrane anchoring domain, and with or without a secretory signal.

When the trk receptor is expressed in a recombinant cell other than one of human origin, the trk receptor is completely free of proteins or polypeptides of human origin. However, it is necessary to purify the trk receptor from recombinant cell proteins or polypeptides to obtained preparations that are substantially homogenous as to the trk receptor. As a first step, the culture medium or lysate is centrifuged to remove particulate cell debris. The membrane and soluble protein fractions are then separated. The trk receptor may then be purified from the soluble protein fraction and from the membrane fraction of the culture lysate, depending on whether the trk receptor is membrane bound. The following procedures are exemplary of suitable purification procedures: fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; and protein A Sepharose columns to remove contaminants such as IgG.

Trk receptor functional derivatives in which residues have been deleted, inserted and/or substituted are recovered in the same fashion as the native receptor chains, taking into account of any substantial changes in properties occasioned by the alteration. For example, fusion of the trk receptor with another protein or polypeptide, e.g. a bacterial or viral antigen, facilitates purification; an immunoaffinity column containing antibody to the antigen can be used to absorb the fusion. Immunoaffinity columns such as a rabbit polyclonal anti-trk receptor column can be employed to absorb trk receptor variant by binding to at least one remaining immune epitope. A protease inhibitor, such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native trk receptor may require modification to account for changes in the character of the trk receptor or its variants upon expression in recombinant cell culture.

I. Covalent Modifications of trk receptor

Covalent modifications of trk receptor are included within the scope herein. Such modifications are traditionally introduced by reacting targeted amino acid residues of the trk receptor with an organic derivatizing agent that is capable of reacting with selected sides or terminal residues, or by harnessing mechanisms of post-translational modifications that function in selected recombinant host cells. The resultant covalent derivatives are useful in programs directed at identifying residues important for biological activity, for immunoassays of the trk receptor, or for the preparation of anti-trk receptor antibodies for immunoaffinity purification of the recombinant. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; 0-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay.

Carboxyl side groups (aspartyl or glutamyl) are selectively modified by reaction with carbodiimides (R'—N=C=N—R') such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl, threonyl or tyrosyl residues, methylation of the α-amino groups of lysine, arginine, and histidine side chains (T. E. Creighton, *Proteins: Structure and Molecular Properties*, W. H. Freeman & Co., San Francisco, pp. 79–86 [1983]), acetylation of the N-terminal amine, and amidation of any C-terminal carboxyl group. The molecules may further be covalently linked to nonproteinaceous polymers, e.g. polyethylene glycol, polypropylene glycol or polyoxyalkylenes, in the manner set forth in U.S. Ser. No. 07/275,296 or U.S. Pat. Nos. 4,640,835; 4,496,689; 4,301,144; 4,670,417; 4,791,192 or 4,179,337.

Derivatization with bifunctional agents is useful for preparing intramolecular aggregates of the trk receptor with polypeptides as well as for cross-linking the trk receptor to a water insoluble support matrix or surface for use in assays or affinity purification. In addition, a study of interchain cross-links will provide direct information on conformational structure. Commonly used cross-linking agents include 1,1-bis(diazoacetyl)-2-phenylethane, glutaraldehyde, N-hydroxysuccinimide esters, homobifunctional imidoesters, and bifunctional maleimides. Derivatizing agents such as methyl-3-[(p-azidophenyl)dithio] propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Certain post-translational modifications are the result of the action of recombinant host cells on the expressed polypeptide. Glutaminyl and aspariginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl, threonyl or tyrosyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)].

Other derivatives comprise the novel peptides of this invention covalently bonded to a nonproteinaceous polymer. The nonproteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol.

The trk receptor may be linked to various nonproteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

The trk receptor may be entrapped in microcapsules prepared, for example, by coacervation techniques or by interfacial polymerization, in colloidal drug delivery systems (e.g. liposomes, albumin microspheres, microemulsions, nano-particles and nanocapsules), or in macroemulsions. Such techniques are disclosed in *Remington's Pharmaceutical Sciences*, 16th Edition, Osol, A., Ed. (1980).

J. Glycosylation variants of the trk receptor

The native trk receptors are glycoproteins. Variants having a glycoslation pattern which differs from that of any native amino acid sequence which might be present in the molecules of the present invention are within the scope herein. For ease, changes in the glycosylation pattern of a native polypeptide are usually made at the DNA level, essentially using the techniques discussed hereinabove with respect to the amino acid sequence variants.

Chemical or enzymatic coupling of glycosydes to the trk receptor of the molecules of the present invention may also be used to modify or increase the number or profile of carbohydrate substituents. These procedures are advantageous in that they do not require production of the polypeptide that is capable of O-linked (or N-linked) glycosylation. Depending on the coupling mode used, the sugar(s) may be attached to (a) arginine and histidine, (b) free carboxyl groups, (c) free hydroxyl groups such as those of cysteine, (d) free sulfhydryl groups such as those of serine, threonine, or hydroxyproline, (e) aromatic residues such as those of phenylalanine, tyrosine, or tryptophan or (f) the amide group of glutamine. These methods are described in WO 87/05330 (published 11 Sep. 1987), and in Aplin and Wriston, *CRC Crit. Rev. Biochem.*, pp. 259–306.

Carbohydrate moieties present on a polypeptide may also be removed chemically or enzymatically. Chemical deglycosylation requires exposure to trifluoromethanesulfonic acid or an equivalent compound. This treatment results in the cleavage of most or all sugars, except the linking sugar, while leaving the polypeptide intact. Chemical deglycosylation is described by Hakimuddin et al., *Arch. Biochem. Biophys.* 259, 52 (1987) and by Edge et al., *Anal. Biochem.* 118, 131 (1981). Carbohydrate moieties can be removed by a variety of endo- and exoglycosidases as described by Thotakura et al., *Meth. Enzymol.* 138, 350 (1987). Glycosylation is suppressed by tunicamycin as described by Duskin et al., *J. Biol. Chem.* 257, 3105 (1982). Tunicamycin blocks the formation of protein-N-glycosydase linkages.

Glycosylation variants can also be produced by selecting appropriate host cells of recombinant production. Yeast, for example, introduce glycosylation which varies significantly from that of mammalian systems. Similarly, mammalian cells having a different species (e.g. hamster, murine, insect, porcine, bovine or ovine) or tissue (e.g. lung, liver, lymphoid, mesenchymal or epidermal) origin than the source of the native trk receptor, are routinely screened for the ability to introduce variant glycosylation.

K. trk receptor-immunoglobulin chimeras (immunoadhesins)

Immunoadhesins are chimeric antibody-like molecules that combine the functional domain(s) of a binding protein (usually a receptor, a cell-adhesion molecule or a ligand) with the an immunoglobulin sequence. The immunoglobulin sequence preferably (but not necessarily) is an immunoglobulin constant domain.

Immunoglobulins (Ig) and certain variants thereof are known and many have been prepared in recombinant cell culture. For example, see U.S. Pat. No. 4,745,055; EP 256,654; Faulkner et al., *Nature* 298:286 (1982); EP 120, 694; EP 125,023; Morrison, *J. Immun.* 123:793 (1979); K öhler et al., Proc. Nat'l. Acad. Sci. USA 77:2197 (1980); Raso et al., *Cancer Res.* 41:2073 (1981); Morrison et al., *Ann. Rev. Immunol.* 2:239 (1984); Morrison, *Science* 229:1202 (1985); Morrison et al., *Proc. Nat'l. Acad. Sci. USA* 81:6851 (1984); EP 255,694; EP 266,663; and WO 88/03559. Reassorted immunoglobulin chains also are known. See for example U.S. Pat. No. 4,444,878; WO 88/03565; and EP 68,763 and references cited therein. The immunoglobulin moiety in the chimeras of the present invention may be obtained from IgG-1, IgG-2, IgG-3 or IgG-4 subtypes, IgA, IgE, IgD or IgM, but preferably IgG-1 or IgG-3.

Chimeras constructed from a receptor sequence linked to an appropriate immunoglobulin constant domain sequence (immunoadhesins) are known in the art. Immunoadhesins reported in the literature include fusions of the T cell receptor* [Gascoigne et al., *Proc. Natl.Acad. Sci. USA* 84, 2936–2940 (1987)]; CD4* [Capon et al., *Nature* 337, 525–531 (1989); Traunecker et al., *Nature* 339, 68–70 (1989); Zettmeissl et al., *DNA Cell Biol. USA* 9, 347–353 (1990); Byrn et al., *Nature* 344, 667–670 (1990)]; L-selectin (homing receptor) [Watson et al., *J. Cell. Biol.* 110, 2221–2229 (1990); Watson et al., *Nature* 349, 164–167 (1991)]; CD44* [Aruffo et al., *Cell* 61, 1303–1313 (1990)]; CD28* and B7* [Linsley et al., *J. Exp. Med.* 173, 721–730 (1991)]; CTLA-4* [Lisley et al., *J. Exp. Med.* 174, 561–569 (1991)]; CD22* [Stamenkovic et al., *Cell* 66. 1133–1144 (1991)]; TNF receptor [Ashkenazi et al., *Proc. Natl. Acad. Sci. USA* 88, 10535–10539 (1991); Lesslauer et al., *Eur. J. Immunol.* 27, 2883–2886 (1991); Peppel et al., *J. Exp. Med.* 174, 1483–1489 (1991)]; NP receptors [Bennett et al., J. Biol. Chem. 266, 23060–23067 (1991)]; IgE receptor α* [Ridgway and Gorman, *J. Cell. Biol.* 115, abstr. 1448 (1991)]; HGF receptor [Mark, M. R. et al., 1992, *J. Biol. Chem.* submitted], where the asterisk (*) indicates that the receptor is member of the immunoglobulin superfamily.

The simplest and most straightforward immunoadhesin design combined the binding region(s) of the 'adhesin' protein with the hinge and Fc regions of an immunoglobulin heavy chain. Ordinarily, when preparing the trk receptor-immunoglobulin chimeras of the present invention, nucleic acid encoding the extracellular domain or a fragment thereof of a desired trk receptor will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain.

The precise site at which the fusion is made is not critical; particular sites are well known and may be selected in order to optimize the biological activity, secretion or binding characteristics of the trk receptor-immunoglobulin chimeras.

In some embodiments, the trk receptor-immunoglobulin chimeras are assembled as monomers, or hetero- or homo-multimers, and particularly as dimers or tetramers, essentially as illustrated in WO 91/08298.

In a preferred embodiment, the trk receptor extracellular domain sequence, which preferably includes the second immunoglobulin-like domain, is fused to the N-terminus of the C-terminal portion of an antibody (in particular the Fc domain), containing the effector functions of an immunoglobulin, e.g. immunoglobulin $G_1$ (IgG-1). It is possible to fuse the entire heavy chain constant region to the trk receptor extracellular domain sequence. However, more preferably, a sequence beginning in the hinge region just upstream of the papain cleavage site (which defines IgG Fc chemically; residue 216, taking the first residue of heavy chain constant region to be 114 [Kobet et al., supra], or analogous sites of other immunoglobulins) is used in the fusion. In a particularly preferred embodiment, the trk receptor amino acid sequence is fused to the hinge region and CH2 and CH3 or CH1, hinge, CH2 and CH3 domains of an IgG-1, IgG-2, or IgG-3 heavy chain. The precise site at which the fusion is made is not critical, and the optimal site can be determined by routine experimentation.

In some embodiments, the trk receptor-immunoglobulin chimeras are assembled as multimers, and particularly as homo-dimers or -tetramers. Generally, these assembled immunoglobulins will have known unit structures. A basic four chain structural unit is the form in which IgG, IgD, and IgE exist. A four unit is repeated in the higher molecular weight immunoglobulins; IgM generally exists as a pentamer of basic four units held together by disulfide bonds. IgA globulin, and occasionally IgG globulin, may also exist in multimeric form in serum. In the case of multimer, each four unit may be the same or different.

Various exemplary assembled trk receptor-immunoglobulin chimeras within the scope herein are schematically diagrammed below:

(a) $AC_L$—$AC_L$;
(b) $AC_H$-[$AC_H$, $AC_L$-$AC_H$, $AC_L$-$V_HC_H$, or $V_LC_L$-$AC_H$];
(c) $AC_L$-$AC_H$-[$AC_L$-$AC_H$, $AC_L$-$V_HC_H$, $V_LC_L$-$AC_H$, or $V_LC_L$-$V_HC_H$];
(d) $AC_L$-$V_HC_H$-[$AC_H$, or $AC_L$-$V_HC_H$, or $V_LC_L$-$AC_H$];
(e) $V_LC_L$-$AC_H$-[$AC_L$-$V_HC_H$, or $V_LC_L$-$AC_H$]; and
(f) [$A$-$Y$]$_n$-[$V_LC_L$-$V_HC_H$]$_2$, wherein each A represents identical or different trk receptor amino acid sequences;

$V_L$ is an immunoglobulin light chain variable domain;

$V_H$ is an immunoglobulin heavy chain variable domain;

$C_L$ is an immunoglobulin light chain constant domain;

$C_H$ is an immunoglobulin heavy chain constant domain;

n is an integer greater than 1;

Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed as being present in the ordinary locations which they occupy in the immunoglobulin molecules.

Alternatively, the trk receptor extracellular domain sequences can be inserted between immunoglobulin heavy chain and light chain sequences such that an immunoglobulin comprising a chimeric heavy chain is obtained. In this embodiment, the trk receptor sequences are fused to the 3' end of an immunoglobulin heavy chain in each arm of an immunoglobulin, either between the hinge and the CH2 domain, or between the CH2 and CH3 domains. Similar constructs have been reported by Hoogenboom, H. R. et al., *Mol. Immunol.* 28, 1027–1037 (1991).

Although the presence of an immunoglobulin light chain is not required in the immunoadhesins of the present invention, an immunoglobulin light chain might be present either covalently associated to an trk receptor-immunoglobulin heavy chain fusion polypeptide, or directly fused to the trk receptor extracellular domain. In the former case, DNA encoding an immunoglobulin light chain is typically coexpressed with the DNA encoding the trk receptor-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Method suitable for the preparation of such structures are, for example, disclosed in U.S. Pat. No. 4,816,567 issued 28 Mar. 1989.

In a preferred embodiment, the immunoglobulin sequences used in the construction of the immunoadhesins of the present invention are from an IgG immunoglobulin heavy chain constant domain. For human immunoadhesins, the use of human IgG1 and IgG3 immunoglobulin sequences is preferred. A major advantage of using IgG 1 is that IgG1 immunoadhesins can be purified efficiently on immobilized protein A. In contrast, purification of IgG3 requires protein G, a significantly less versatile medium. However, other structural and functional properties of immunoglobulins should be considered when choosing the Ig fusion partner for a particular immunoadhesin construction. For example, the IgG3 hinge is longer and more flexible, so it can accommodate larger 'adhesin' domains that may not fold or function properly when fused to IgG1. Another consideration may be valency; IgG immunoadhesins are bivalent homodimers, whereas Ig subtypes like IgA and IgM may give rise to dimeric or pentameric structures, respectively, of the basic Ig homodimer unit. For trk-Ig immunoadhesins designed for in vivo application, the pharmacokinetic properties and the effector functions specified by the Fc region are important as well. Although IgG1, IgG2 and IgG4 all have in vivo half-lives of 21 days, their relative potencies at activating the complement system are different. IgG4 does not activate complement, and IgG2 is significantly weaker at complement activation than IgG1. Moreover, unlike IgG1, IgG2 does not bind to Fc receptors on mononuclear cells or neutrophils. While IgG3 is optimal for complement activation, its in vivo half-life i approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, IgG1 has only four serologically-defined allotypic sites, two of which (G1m and 2) are located in the Fc region; and one of these sites G1m1, is non-immunogenic. In contrast, there are 12 serologically-defined allotypes in IgG3, all of which are in the Fc region; only three of these sites (G3m5, 11 and 21) have one allotype which is nonimmunogenic. Thus, the potential immunogenicity of a y3 immunoadhesin is greater than that of a γ1 immunoadhesin.

In designing the trk-Ig immunoadhesins of the present invention domain that are not required for neurotrophin binding and/or biological activity may be deleted. In such structures, it is important to place the fusion junction at residues that are located between domains, to avoid misfolding. With respect to the parental immunoglobulin, a useful joining point is just upstream of the cysteines of the hinge that form the disulfide bonds between the two heavy chains. In a frequently used design, the codon for the C-terminal residue of the 'adhesin' (trk) part of the molecule is placed directly upstream of the codons for the sequence DKTHTCPPCP of the IgG1 hinge region.

The general methods suitable for the construction and expression of immunoadhesins are the same those disclosed hereinabove with regard to (native or variant) trk receptors. trk-Ig immunoadhesins are most conveniently constructed by fusing the cDNA sequence encoding the trk portion in-frame to an Ig cDNA sequence. However, fusion to genomic Ig fragments can also be used [see, e.g. Gascoigne et al., *Proc. Natl. Acad. Sci. USA* 84, 2936– 2940 (1987); Aruffo et al., *Cell* 61, 1303–1313 (1990); Stamenkovic et al., *Cell* 66, 1133–1144 (1991)]. The latter type of fusion requires the presence of Ig regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques. The cDNAs encoding the 'adhesin' and the Ig parts of the immunoadhesin are inserted in tandem into a plasmid vector that directs efficient expression in the chosen host cells. For expression in mammalian cells pRK5-based vectors [Schall et al., *Cell* 61, 361–370 (1990)] and CDM8-based vectors [Seed, *Nature* 329, 840 (1989)]. The exact junction can be created by removing the extra sequences between the designed junction codons using oligonucleotide-directed deletional mutagenesis [Zoller and Smith, *Nucleic Acids Res.* 10, 6487 (1982); Capon et al., *Nature* 337, 525–531 (1989)]. Synthetic oligonucleotides can be used, in which each half is complementary to the sequence on either side of the desired junction; ideally, these are 36 to 48-mers. Alternatively, PCR techniques can be used to join the two parts of the molecule in-frame with an appropriate vector.

The choice of host cell line for the expression of trk-Ig immunoadhesins depends mainly on the expression vector. Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient immunoadhesin expression. CDM8-based vectors can be used to transfect COS cells by the DEAE-dextran method (Aruffo et al., *Cell* 61, 1303–1313 (1990); Zettmeissl et al., *DNA Cell Biol.* (*US*) 9, 347–353 (1990)]. If larger amounts of protein are desired, the immunoadhesin can be expressed after stable transfection of a host cell line. For example, a pRK5-based vector can be introduced into Chinese hamster ovary (CHO) cells in the presence of an additional plasmid encoding dihydrofolate reductase (DHFR) and conferring resistance to G418. Clones resistant to G418 can be selected in culture; these clones are grown in the presence of increasing levels of DHFR inhibitor methotrexate; clones are selected, in which the number of gene copies encoding the DHFR and immunoadhesin sequences is co-amplified. If the immunoadhesin contains a hydrophobic leader sequence at its N-terminus, it is likely to be processed and secreted by the transfected cells. The expression of immunoadhesins with more complex structures may require uniquely suited host cells; for example, components such as light chain or J chain may be provided by certain myeloma or hybridoma cell hosts [Gascoigne et al., 1987, supra; Martin et al., *J. Virol.* 67, 3561–3568 (1993)].

Immunoadhesins can be conveniently purified by affinity chromatography. The suitability of protein A as an affinity ligand depends on the species and isotype of the immunoglobulin Fc domain that is used in the chimera. Protein A can be used to purify immunoadhesins that are based on human γ1, γ2, or γ4 heavy chains [Lindmark et al., *J. Immunol. Meth.* 62, 1–13 (1983)]. Protein G is recommended for all mouse isotypes and for human γ3 [Guss et al., *EMBO J.* 5, 15671575 (1986)]. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. One distinguishing feature of immunoadhesins is that, for human γ1 molecules, the binding capacity for protein A is somewhat diminished relative to an antibody of the same Fc type. Bound immunoadhesin can be efficiently eluted either at acidic pH (at or above 3.0), or in a neutral pH buffer containing a mildly chaotropic salt. This affinity chromatography step can result in an immunoadhesin preparation that is >95% pure.

Other methods known in the art can be used in place of, or in addition to, affinity chromatography on protein A or G to purify immunoadhesins. Immunoadhesins behave similarly to antibodies in thiophilic gel chromatography [Hutchens and Porath, *Anal. Biochem.* 159, 217–226 (1986)] and immobilized metal chelate chromatography [Al-Mashikhi and Makai, *J. Dairy Sci.* 71, 1756–1763 (1988)]. In contrast to antibodies, however, their behavior on ion exchange columns is dictated not only by their isoelectric points, but also by a charge dipole that may exist in the molecules due to their chimeric nature.

If desired, the immunoadhesins can be made bispecific, that is, directed against two distinct ligands. Thus, the immunoadhesins of the present invention may have binding specificities for two distinct neurotrophins, or may specifically bind to a neurotrophin and to an other determinant specifically expressed on the cells expressing the neurotrophin to which the trk portion of the immunoadhesin structure binds. For bispecific molecules, trimeric molecules, composed of a chimeric antibody heavy chain in one arm and a chimeric antibody heavy chain-light chain pair in the other arm of their antibody-like structure are advantageous, due to ease of purification. In contrast to antibody-producing quadromas traditionally used for the production of bispecific immunoadhesins, which produce a mixture of ten tetramers, cells transfected with nucleic acid encoding the three chains of a trimeric immunoadhesin structure produce a mixture of only three molecules, and purification of the desired product from this mixture is correspondingly easier.

L. trk receptor antibody preparation (i) Polyclonal antibodies

Polyclonal antibodies to the trk receptor generally are raised in animals by multiple subcutaneous (sc) or intraperitoneal (ip) injections of the trk receptor and an adjuvant. It may be useful to conjugate the trk receptor or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, $SOCl_2$, or $R^1N=C=NR$, where R and $R^1$ are different alkyl groups.

Animals are immunized against the immunogenic conjugates or derivatives by combining 1 mg of 1 μg of conjugate (for rabbits or mice, respectively) with 3 volumes of Freud's complete adjuvant and injecting the solution intradermally at multiple sites. One month later the animals are boosted with ⅕ to ¹⁄₁₀ the original amount of conjugate in Freud's complete adjuvant by subcutaneous injection at multiple sites. 7 to 14 days later the animals are bled and the serum is assayed for anti-trk receptor antibody titer. Animals are boosted until the titer plateaus. Preferably, the animal boosted with the conjugate of the same trk receptor, but conjugated to a different protein and/or through a different cross-linking reagent. Conjugates also can be made in recombinant cell culture as protein fusions. Also, aggregating agents such as alum are used to enhance the immune response.

(ii) Monoclonal antibodies

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, the anti-trk receptor monoclonal antibodies of the invention may be made using the hybridoma method first described by Kohler & Milstein, *Nature* 256:495 (1975), or may be made by recombinant DNA methods [Cabilly, et al., U.S. Pat. No. 4,816,567].

In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell [Goding, *Monoclonal Antibodies: Principles and Practice*, pp.59–103 (Academic Press, 1986)].

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA.

Culture medium in which hybridoma cells are growing is assayed for production of monoclonal antibodies directed against trk receptor. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson & Pollard, Anal. Biochem. 107:220 (1980).

After hybridoma cells are identified that produce antibodies of the desired specificity, affinity, and/or activity, the clones may be subcloned by limiting dilution procedures and grown by standard methods. Goding, *Monoclonal Antibodies: Principles and Practice*, pp.59–104 (Academic Press, 1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-trk monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for an trk receptor and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; biotin; radioactive isotopic labels, such as, e.g., $^{125}I$, $^{32}P$, $^{14}C$, or $^3H$, or an enzyme, such as alkaline phosphatase, beta-galactosidase or horseradish peroxidase.

Any method known in the art for separately conjugating the antibody to the detectable moiety may be employed, including those methods described by Hunter, et al., *Nature* 144:945 (1962); David, et al., *Biochemistry* 13:1014 (1974); Pain, et al., *J. Immunol. Meth.* 40:219 (1981); and Nygren, *J. Histochem. and Cytochem.* 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques*, pp.147–158 (CRC Press, Inc., 1987).

Competitive binding assays rely on the ability of a labeled standard (which may be an trk receptor or an immunologically reactive portion thereof) to compete with the test sample analyte (trk receptor) for binding with a limited amount of antibody. The amount of trk receptor in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

(iii) Humanized antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature* 321, 522–525 (1986); Riechmann et al., *Nature* 332, 323–327 (1988); Verhoeyen et al., *Science* 239, 1534–1536 (1988)], by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed 21 Aug. 192, which is a continuation-in-part of application Ser. No. 07/715,272 filed 14 Jun. 1991.

(iv) Human antibodies

Human monoclonal antibodies can be made by the hybridoma method. Human myeloma and mouse-human heteromyeloma cell lines for the production of human monoclonal antibodies have been described, for example, by Kozbor, *J. Immunol.* 133, 3001 (1984), and Brodeur, et al., *Monoclonal Antibody Production Techniques and Applications*, pp.51–63 (Marcel Dekker, Inc., New York, 1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germ-line mutant mice result s in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA* 90, 2551–255 (1993); Jakobovits et al., *Nature* 362 255–258 (1993).

Alternatively, the phage display technology (McCafferty et al., *Nature* 348, 552–553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimicks some of the properties of the B-cell. Phage display can be performed in a variety of formats; for their review see, e.g. Johnson, Kevin S. and Chiswell, David J., *Current Opinion in Structural Biology* 3, 564–571 (1993). Several sources of V-gene segments can be used for phage display. Clackson et al., *Nature* 352, 624–628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222, 581–597 (1991), or Griffith et al., *EMBO J.* 12, 725–734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., *Bio/Technol.* 10, 779–783 [1992]). In this method, the affinity of "primary" human antibodies obtained by phage display can be improved by sequentially replacing the heavy and light chain V region genes with repertoires of naturally occurring variants (repertoires) of V domain genes obtained from unimmunized donors. This techniques allows the production of antibodies and antibody fragments with affinities in the nM range. A strategy for making very large phage antibody repertoires (also known as "the mother-of-all libraries") has been described by Waterhouse et al., *Nucl. Acids Res.* 21, 2265–2266 (1993), and the isolation of a high affinity human antibody directly from such large phage library is reported by Griffith et al., *EMBO J.* (1994), in press. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213, published 1 Apr. 1993). Unlike traditional humanization of rodent antibodies by CDR grafting, this technique provides completely human antibodies, which have no framework or CDR residues of rodent origin.

(v) Bispecific antibodies

Bispecific antibodies are monoclonal, preferably human or humanized, antibodies that have binding specificities for at least two different antigens. In the present case, one of the binding specificities is for a trk receptor, the other one is for any other antigen, and preferably for another receptor or receptor subunit. For example, bispecific antibodies specifically binding a trk receptor and neurotrophic factor, or two different trk receptors are within the scope of the present invention.

Methods for making bispecific antibodies are known in the art.

Traditionally, the recombinant production of bispecific antibodies is based on the coexpression of two immunoglobulin heavy chain-light chain pairs, where the two heavy chains have different specificities (Millstein and Cuello, *Nature* 305, 537–539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published 13 May 1993), and in Traunecker et al., *EMBO* 10, 3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in copending application Ser. No. 07/931,811 filed 17 Aug. 1992.

For further details of generating bispecific antibodies see, for example, Suresh et al., *Methods in Enzymology* 121, 210 (1986).

(v) Heteroconjugate antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

M. Use of the trk-Ig immunoadhesins (i) Ligand binding

As in antibodies, the Fc region of immunoadhesins provides a convenient handle not only for purification, but also for capture and detection. This is useful for quantitation of the immunoadhesin (e.g., in transfected cell supernatants) using a sandwich ELISA with two different anti-Fc antibodies. In addition, the Fc handle facilitates investigating the interaction of the trk portion with the corresponding neurotrophin(s). For example, a microtiter plate binding assay format can be used, in which the immunoadhesin is immobilized onto wells that have been pre-coated with anti-Fc antibody. This positions the immunoadhesin in an orientation which leaves the trk portion accessible for binding by a cognate neurotrophin ligand. The ligand is then added and incubated with the immobilized immunoadhesin. After removal of the unbound ligand by washing, binding is quantitated by counting radioactivity if the neurotrophin ligand is radiolabeled, or by anti-neurotrophin antibodies. Nonspecific binding can be determined by omitting the immunoadhesin or by including an isotype-matched immunoadhesin with an irrelevant 'adhesin' portion. This assay format can be used for the diagnosis of pathological conditions characterized by the under- or overexpression of certain neurotrophins, and is also useful in comparing the binding of various neurotrophic factors to a trkA, trkB or trkC receptor, and in efforts aimed at finding new ligands for trk receptors, e.g., in screening libraries of synthetic or natural organic compounds.

(ii) Ligand identification/isolation

Another area in which trk-Ig immunoadhesins can be used is search for further neurotrophins in the human or in various animal species, and for purifying such ligands. Ligands identified so far by this approach include two L-selectin ligands, GlyCAM-1 and CD34, which were identified and purified using an L-selectin-IgG affinity column (Imai et al., *J. Cell. Biol.* 113, 1213–1221 (1991); Watson et al., *J. Cell. Biol.* 110, 2221–2229 (1990); Watson et al., *J. Cell. Biol.* 349, 164–167 (1991)].

(iii) Production of large quantities of purified soluble trk receptors

The structural similarity between immunoadhesins and antibodies suggested that it might be possible to cleave immunoadhesins by proteolytic enzymes such as papain, to generate Fd-like fragments containing the 'adhesin' portion. In order to provide a more generic approach for cleavage of immunoadhesins, proteases which are highly specific for their target sequence are to be used. A protease suitable for this purpose is an engineered mutant of subtilisin BPN, which recognizes and cleaves the sequence AAHYTL. Introduction of this target sequence into the support hinge region of a trk-IgG1 immunoadhesin facilitates highly specific cleavage between the Fc and trk domains. The immunoadhesin is purified by protein A chromatography and cleaved with an immobilized for of the enzyme. Cleavage results in two products; the Fc region and the trk region. These fragments can be separated easily by a second passage over a protein A column to retain the Fc and obtain the purified trk fragments in the flow-through fractions. A similar approach can be used to generate a dimeric trk portion, by placing the cleavable sequence at the lower hinge.

N. Use of trk receptors (i) Kinase receptor activation assay

The trk receptors can be used in the kinase receptor activation (KIRA) assay. This ELISA-type assay is suitable for qualitative or quantitative measurement of kinase activation by measuring the autophosphorylation of the kinase domain of a receptor protein tyrosine kinase (rPTK, e.g. trk receptor), as well as for identification and characterization of potential agonist or antagonists of a selected rPTK. The first stage of the assay involves phosphorylation of the kinase domain of a kinase receptor, e.g. a trk receptor, wherein the receptor is present in the cell membrane of a eukaryotic cell. The receptor may be an endogenous receptor or nucleic acid encoding the receptor, or a receptor construct, may be transformed into the cell. Typically, a first solid phase (e.g., a well of a first assay plate) is coated with a substantially homogeneous population of such cells (usually a mammalian cell line) so that the cells adhere to the solid phase. Often, the cells are adherent and thereby adhere naturally to the first solid phase. If a "receptor contruct" is used, it usually comprises a fusion of a kinase receptor and a flag polypeptide. The flag polypeptide is recognized by the capture agent, often a capture antibody, in the ELISA part of the assay. An analyte is then added to the wells having the adhering cells, such that the tyrosine kinase receptor (e.g. trk receptor) is exposed to (or contacted with) the analyte. This assay enables identification of agonist and antagonist ligands for the tyrosine kinase receptor of interest (e.g. trk A, trk B or trk C). In order to detect the presence of an antagonist ligand which blocks binding of an agonist to the receptor, the adhering cells are exposed to the suspected antagonist ligand first, and then to the agonist ligand, so that competitive inhibition of receptor binding and activation can be measured. Also, the assay can identify an antagonist which binds to the agonist ligand and thereby reduces or eliminates its ability to bind to, and activate, the rPTK. To detect such an antagonist, the suspected antagonist and the agonist for the rPTK are incubated together and the adhering cells are then exposed to this mixture of ligands. Following exposure to the analyte, the adhering cells are solubilized using a lysis buffer (which has a solubilizing detergent therein) and gentle agitation, thereby releasing cell lysate which can be subjected to the ELISA part of the assay directly, without the need for concentration or clarification of the cell lysate. The cell lysate thus prepared is then ready to be subjected to the ELISA stage of the assay. As a first step in the ELISA stage, a second solid phase (usually a well of an ELISA microtiter plate) is coated with a capture agent (often a capture antibody) which binds specifically to the tyrosine kinase receptor, or, in the case of a receptor construct, to the flag polypeptide. Coating of the second solid phase is carried out so that the capture agent adheres to the second solid phase. The capture agent is generally a monoclonal antibody, but, as is described in the examples herein, polyclonal antibodies may also be used. The cell lysate obtained is then exposed to, or contacted with, the adhering capture agent so that the receptor or receptor construct adheres to (or is captured in) the second solid phase. A washing step is then carried out, so as to remove unbound cell lysate, leaving the captured receptor or receptor construct. The adhering or captured receptor or receptor construct is then exposed to, or contacted with, an anti-phosphotyrosine antibody which identifies phosphorylated tyrosine residues in the tyrosine kinase receptor. In the preferred embodiment, the anti-phosphotyrosine antibody is conjugated (directly or indirectly) to an enzyme which catalyses a color change of a non-radioactive color reagent. Accordingly, phosphorylation of the receptor can be measured by a subsequent color change of the reagent. The enzyme can be bound to the anti-phosphotyrosine antibody directly, or a conjugating molecule (e.g., biotin) can be conjugated to the anti-phosphotyrosine antibody and the enzyme can be subsequently bound to the anti-phosphotyrosine antibody via the conjugating molecule. Finally, binding of the anti-phosphotyrosine antibody to the captured receptor or receptor construct is measured, e.g., by a color change in the color reagent.

(ii) Therapeutic use

The trkB and trkC receptor polypeptides of the present invention as well as the antibodies specifically binding such receptors, either in monospecific or bispecific or heteroconjugate form, are useful in signaling, enhancing or blocking the biological activity of neurotrophins capable of binding at least one of these receptors. The trk-Ig immunoadhesins of the present invention have been found to block the interaction of the trk receptors with their neurotrophic ligands, and thereby inhibit neurotrophin biological activity. This antagonist activity is believed to be useful in the treatment of pathological conditions associated with endogenous neurotrophin production, such as inflammatory pain (trkA-immunoadhesin; see Example 5), pancreas (trkB-immunoadhesin), kidney disorders, lung disorders, cardiovascular disorders (trkC-immunoadhesins), various types of tumors (trkA-, trkB- and trkC-immunoadhesins), aberrant sprouting in epilepsy, psychiatric disorders (trkB- and trkC-immunoadhesins). Human immunoadhesins can be based on human sequences of both the trk and Ig portions of the molecule, such that the only novel sequence which may be recognized as 'foreign' by the human immune system is the junction. Therefore, human immunoadhesins, in contrast to chimeric (humanized) antibodies, are minimally immunogenic in humans. This reduced immunogenicity is an important advantage especially for indications that require multiple administrations.

Therapeutic formulations of the present invention are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules) or in macroemulsions. Such techniques are disclosed in *Remington's Pharmaceutical Sciences*, supra.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Suitable examples of sustained release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (U. Sidman et al., 1983, "Biopolymers" 22 (1): 547–556), poly (2-hydroxyethyl-methacrylate) (R. Langer, et al., 1981, "J. Biomed. Mater. Res." 15: 167–277 and R. Langer, 1982, Chem. Tech." 12: 98–105), ethylene vinyl acetate (R. Langer et al., Id.) or poly-D-(-)-3-hydroxybutyric acid (EP 133, 988A). Sustained release compositions also include liposomes. Liposomes containing a molecule within the scope of the present invention are prepared by methods known per se: DE 3,218,121A; Epstein et al., 1985, "Proc. Natl. Acad. Sci. USA" 82: 3688–3692; Hwang et al., 1980, "Proc. Natl. Acad. Sci. USA" 77: 4030–4034; EP 52322A; EP 36676A; EP 88046A; EP 143949A; EP 142641A; Japanese patent application 83-118008; U.S. Pat. Nos. 4,485,045 and 4,544, 545; and EP 102,324A. Ordinarily the liposomes are of the small (about 200–800 Angstroms) unilamelar type in which the lipid content is greater than about 30 mol. % cholesterol, the selected proportion being adjusted for the optimal NT-4 therapy.

An effective amount of a molecule of the present invention to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 μg/kg to up to 100 mg/kg or more, depending on the factors mentioned above. Typically, the clinician will administer a molecule of the present invention until a dosage is reached that provides the required biological effect. The progress of this therapy is easily monitored by conventional assays The invention will be further illustrated by the following non-limiting examples. For the experiments described in the Examples, human brain cDNA, poly α+ RNA, genomic and cDNA libraries were obtained from Clontech (Palo Alto, Calif.). pGEM was obtained from Promega (Madison, Wis.), restriction enzymes from New England Biolabs (Beverly, Mass.). Taq polymerase was from Perkin-Elmer (Norwalk, Conn.), while all other enzymes, frozen competent E. coli and tissue culture media were purchased from Gibco-BRL (Raithersburg, Md.).

EXAMPLE 1

Cloning of Human trkB and trkC Receptors

A. Generation of Human trkB and trkC Probes

Human brain cDNA, polyA+ RNA, genomic and cDNA libraries were obtained from Clontech (Palo Alto).

In order to amplify fragments of the human trkB and trkC sequences for use in probing cDNA libraries, the PCR with degenerate primers based on known sequences of rat trkB or pig trkC (see Table 1), was employed. PCR reaction buffer consisted of 10 mM Tris pH 8.4 at room temperature, 2.0 mM $MgCl_2$ and 50 mM KCl. A "hot start" procedure was used for all reactions, samples without enzyme were incubated for ten minutes at 98° C., equilibrated to 65° C. and enzyme added. They were then cycled thirty-five times through 94° C. for 45 seconds; 600 for 45 seconds; and 72° C. for 60 seconds and a final extension at 72° C. for ten minutes.

Fragments amplified by this procedure were subcloned into pGEM vector (Promega, Madison, Wis.) and sequenced. Inserts from clones with sequences similar to known trkB and C sequences were then excised, gel-purified and labeled by random priming with 32 P dCTP. These were used to probe $10^6$ cDNA clones which had been plated at $5\times10^4$ plaques per 15 cm dish, transferred to nitrocellulose (Schleicher and Schuell, Keene, N.H.) in duplicate, denatured with alkali, neutralized and baked at 80° C. for two hours. Filters were prehybridized at 42° C. for at least four hours in 50% formamide, 5× SSC, 5× Denhardt's, 20 mM NaPO4, pH 7.0, 0.1% SDS, and 100 micrograms/ml salmon sperm DNA and hybridized overnight in the same conditions with Denhardt's reduced to 1×. Filters were then washed four times in 2× SSC, 0.1% SDS and twice with 0.1× SSC, 0.1% SDS at room temperature and twice with 0.1× SSC, 0.1% SDS at 42° C. Clones which were positive on both sets of filters were plaque purified and the inserts subcloned either by helper mediated excision (lambda DR2 libraries) or by standard subcloning into PGEM. Oligonucleotide probes were either end labeled using polynucleotide kinase or labeled by "fill-in" reactions using Klenow fragment of DNA polymerase and hybridized to filters under the same conditions but with formamide reduced to 35%. Genomic clones hybridizing to the 5' probe for trkB were digested with Sau3a and resulting fragments were subcloned into BamHI cut M13 mp18. These clones were rescreened as for the lambda libraries (with no denaturation step) and positive clones were plaque purified and sequenced. DNA encoding the full coding region of trkB and trkC were reconstructed using standard techniques.

B. Characterization of human trkB clones

Six clones were obtained using the probe for human trkB. These were mapped using the PCR and primers designed from the sequence obtained in the initial probe and the clones with the greatest 3' and 5' extent were sequenced. Sequence analysis revealed that these clones encoded a protein highly homologous to rodent trkB which contained an entire tyrosine kinase domain and were intact to the 3' poly A+ tail, but were apparently incomplete at the 5' end. An oligonucleotide probe designed from the 5' end of the rat trkB sequence was used to rescreen the initial library and subsequently four other dT primed human brain libraries with no positive clones found. Four positive clones were obtained when a random primed human brain library was screened with this probe. Sequence analysis of these clones indicated that they overlapped with the previous human clones, but, by comparison with the rat, were still missing seventeen bases of coding region at the 5' end. A human genomic library was then probed with the 5' oligonucleotide probe and genomic clones isolated. Sau3a fragments of these clones were then subcloned into M13, rescreened, and positive subclones were sequenced to obtain the last of the coding sequence. The final nucleotide and deduced amino acid sequence of human trkB obtained from the overlapping regions of the cDNA clones is shown in FIGS. 1A–1C.

C. Characterization of human trkC clones

A similar strategy was used to generate probes specific for the extracellular domain of human trkC, and two initial clones were obtained. Both of these were found to contain sequences corresponding to the truncated form of trkC described in the pig and rat (Lamballe et al., [1991] supra; Tsoulfas, [1993] supra; Valenzuela et al., [1993], supra), since the sequence encoded the complete extracellular domain of trkC, a transmembrane domain and a short cytoplasmic domain which contained no TK-like sequences. In order to isolate clones encoding the tyrosine kinase domain of trkC, libraries were reprobed in duplicate with oligonucleotides corresponding to the C-terminal tail of pig trkC and the juxtamembrane region of the intracellular domain of human trkC. Double positive clones were analyzed and found to contain sequence overlapping with the truncated trkC clones and also containing a tyrosine kinase coding sequence. The nucleotide and deduced amino acid sequence obtained from the overlapping regions of these clones is shown in FIGS. 2A–2C.

D. Cloning of human trkA

In addition, trk A was recloned from human brain with the PCR by using exact match primers and human brain cDNA as a template. A resulting clone was sequenced, and five discrepancies with the previously published sequence were seen. Each of these areas were examined by direct sequencing of several different amplification reactions and true errors in the clone sequenced were corrected by site specific mutagenesis. There remained one difference with the previously determined sequence, a GC for CG transposition leading to a switch from serine to cysteine at residue 300 in the deduced amino acid sequence. Due to the sequencing of multiple reactions, and the conservation of this cysteine in rat trkA (Meakin et al., [1992], supra) and all other known trks (see below), it seems likely that the original sequence is in error.

E. Results

Figure 3:
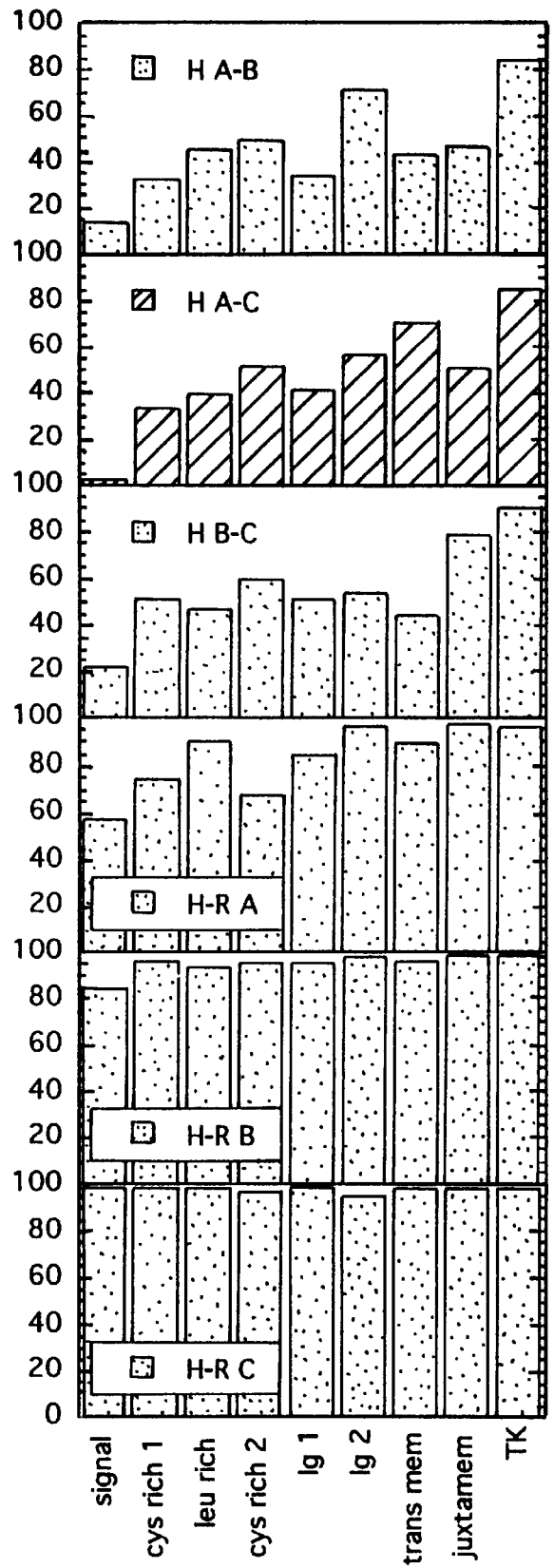
FIG. 3. Similarities of various domains of trk family members from rat and human. Percent similarity based on the PAM250 matrix (Dayhoff et al., 1983) was determined for different trk domains as defined by Schneider and Schweiger, *Oncogene* 6, 1807–1811 (1991). Pairwise comparison were made between human trkA and human trkB (H A-B), human trkA and human trkC (H A-C), human trkB and human trkC (H B-C), human trkA and rat trkA (H-R A), human trkB and rat trkB (H-R B), and human trkC and rat trkC (H-R C).

Examination of the sequences obtained from the human clones and comparison to the known structure of rat and mouse trkB and rat and pig trkC indicates that there is a very high degree of overall sequence similarity across these mammalian species. The overall structural motifs identified by Schneider and Schweiger (1991), supra are maintained, namely, a signal sequence, predicted to be clipped at residues 31 for both trkB and C (later confirmed by N-terminal sequence analysis, see expression of trk immunoadhesins), two cysteine rich domains flanking a leucine rich domain, two Ig like domains of the C2 type, a transmembrane domain, and a tyrosine kinase domain showing high similarity to other known tyrosine kinases. There are 11 and 13 potential N-linked glycosylation sites in the extracellular domains of trkB and C, respectively. The similarity of different regions of the known trks within and across species is shown in FIG. 3.

During sequence analysis of several of the different clones obtained for trkB and C, multiple forms apparently arising from alternate splicing were seen. Variant forms were observed as a possible insert in the extracellular domain of trkC, truncated, non TK forms of trkB and C, and a possible insert within the TK domain of trkC. Using library screening with specific oligonucleotide probes, and the PCR, a more systematic search was then undertaken to search for potential other variants at these sites in the different human trks. A diagram of the different forms found in the different human trks and comparison to those found in other known trks is shown in FIG. 4.

In the extracellular domain of human trkC, there was a possible deletion of nine amino acids compared to rat and pig trkC at a site near to that where the extracellular insert was described in rat and human trkA (Barker et al., *J. Biol. Chem.* 268, 1510–15157 [1993]; FIG. 2). PCR analysis of this region in human trkC showed only two bands, corresponding in length to that expected for the insert-containing and insert-deleted forms. PCR analysis of this region in human trkB showed no detectable length polymorphisms, but amplification using trkA specific primers did show two distinct bands which were cloned and sequenced. The potential nucleotide insert was TCTCCTTCTCGCCGGTGG (SEQ. ID. NO: 38) at position 1297 coding for the identical peptide insert (SEQ ID NO: 39) previously described in rat and human trk-A (Barker, et al., supra).

From the human brain libraries, both trkB and C clones were obtained which did not encode a TK domain but instead showed an alternate, truncated intracellular domain. In trkB, this consisted of eleven new amino acids added after position 435 which are identical to those previously identified in the rat as t1 (Middlemas, et al., [1991], supra) and in the mouse as the truncated form (Klein et al., *EMBO J.* 8, 3701–3709 [1989]). All attempts using cDNA libraries probed with oligonucleotides or using PCR, failed to yield sequences from the human similar to those identified in the rat as t2 (Middlemas, et al. [1991], supra). The PCR readily yielded sequences similar to t2 when either mouse or rat brain cDNA was used as a template, showing that t2 is not unique to the rat and that the techniques used were capable of detecting t2 like sequences at least from the rodent (data not shown).

The truncated form of trkC was longer than that in trkB, and similar to that previously described in pig trkC (Lamballe, et al. [1991], supra) and in the rat (Tsoulfas et al., [1993], supra) or as the ic158 form of rat trkC (Valenzuela et al., [1993], supra). This form consisted of 83 additional amino acids starting at position 498, which were highly conserved across species. In this span, there were only two differences, an aspartate to glutamate and a serine to proline substitution, seen across all three species.

Figure 5:
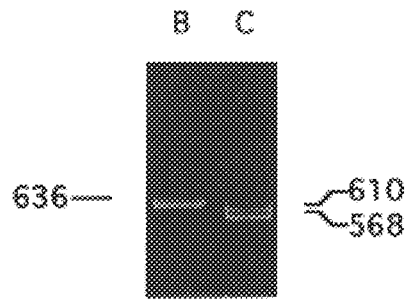
FIG. 5. Amplification of region containing potential insert of tyrosine kinase domain of trkB and trkC. Brain cDNA was amplified with primers selective for the region surrounding the site of the observed insert in the TK domain of trkC. Using primers selective for trkC, two bands of sizes corresponding to the no insert (568) or 14 amino acid insert (610) form are amplified, with no evidence for any larger forms. Using primers selective for trkB, only one band corresponding to the no insert form (636) is detected.

The TK domain of trkC obtained in the CDNA clones contained an apparent insert of fourteen amino acids between subdomains VII and VIII (Hanks et al., *Science* 241: 42–52 [1988] and Hanks et al., *Methods in Enzymol.* 200: 38–62 [1991]. This sequence is inserted in the same site as the observed potential inserts seen in the rat trkC TK domain and is identical in sequence to the fourteen amino acid insert seen there (Hanks et al., [1988], supra; Valenzuela et al., [1993], supra). In addition to the fourteen amino acid insert seen in rat trkC, longer inserts of twenty-five (Tsoulfas et al., [1993], supra) or thirty-nine (Valenzuela et al., [1993], supra) amino acids have been seen. In an attempt to determine if these longer inserts were expressed in the human, brain cDNA was used as a template for PCR amplification across this region (see FIG. 5). These experiments consistently showed two bands of lengths corresponding to the two already observed splice forms, i.e., with and without the fourteen amino acid insert. Cloning and sequencing of these two bands verified that they correspond to the two forms with and without the previously seen fourteen residue insert. Interestingly, this splicing was tissue specific as only the band corresponding to the insert-free form was seen in amplifications using cDNA from a non-neural tissue expressing high levels of trkC, the testis (data not shown). PCR of human brain cDNA using oligos specific for the same region of trkB TK domain showed no evidence for length polymorphisms in this region (see FIG. 5).

F. Discussion

By examining the degrees of similarity between the different trks in a single species and the same trk in different species, certain generalizations may be drawn. The comparison of the three human trks to each other and the equivalent trk from the rat is shown for the different domains as defined by Schneider and Schweiger (1991), supra in FIG. 3. Each of the trks is quite conserved between human and rat, with trkB and trkC being almost identical across these two mammalian species. Each individual domain of trk B and trkC is at least 85% similar between rat and human. On the other hand, trkA, although its overall degree of similarity between human and rat is quite high, shows regions of significant sequence divergence. In particular, in the extracellular domain, it is only the leucine rich and second Ig-like domain which are at least 85%. similar. This may have implications for the localization of the neurotrophin binding domain(s) of the trks. The transmembrane and intracellular domains of trkA are highly conserved between rat and human, similar to trkB and trkC. When similarity comparisons of different trks in the human are examined, it is readily apparent that the TK domain is the most highly conserved across the different trks. Of the extracellular domains, it is again the second Ig-like domain, along with the second cysteine rich domain which are most similar between the different human trks.

In contrast to the conservation of sequence, were the observed differences between the human and previously known trks in the form of differently processed transcripts. In the rodent, trkB contains at least two different truncated forms and northern blots probed for trkB exhibit a complex pattern with many transcript sizes. We failed to find evidence for the existence of the t2 form in the human despite considerable effort and observed a much simpler transcript pattern. for trkB. While we cannot rule out the existence of a homolog of this form in the human, a t2 equivalent seems unlikely to be expressed as abundantly as in the rodent.

One of the proposed roles for the truncated forms of the trks is to act as a dominant negative influence on signal transduction by neurotrophin in the expressing cell (Jing et al., *Neuron* 9, 1067–1079 [1992]). This is consistent with the relative lack of efficacy of neurotrophin signalling seen in tissue from the adult brain when stimulated by neurotrophins (Knusel et al., *J. Neurosci.* [1994]), as the ratio of truncated to non truncated forms of the trks is quite high in the adult (see FIG. 6). If this is the main role for truncated trks, then the apparent absence of t2 in the human is all the more interesting, as it has been shown that, in the rodent, t2 is primarily expressed in neurons, while the other truncated form of trkB, t1, is primarily in non-neuronal cells. If this localization were also true in humans, then human neurons, without t2, would express a much lower level of truncated form of trkB relative to rodents. Thus, the proposed dominant negative effect might not be as important in human neurons as in the rodent.

There are also differences between human and previously described transcripts of trk C. In the extracellular domain, there is apparent alternate splicing giving rise to two forms, with and without an insert of nine amino acids. This apparent insertion site aligns with the previously characterized insertion site in rat trkA. As yet, no functional differences in binding or signal transduction have been detected between the two splice forms in the rat trkA where the insert is six amino acids (Barker et al., *J. Biol. Chem.* 268, 1510–15157 [1993]), but perhaps the there will be greater differences in the human trkC forms with a nine amino acid insert. Whatever the biological role for the differently spliced forms, they are quite species specific, since no evidence of an insert in this location was seen in human trkB in this study, and previous work has not detected the insert in trkC outside the human (Valenzuela et al. [1993], supra; Tsoulfas, [1993], supra; Lamballe, et al. [1991], supra).

We also found examples of various forms of human trkC presumably due to alternate spicing in the intracellular part of the molecule. We observed the presence of a truncated form of trkC, which does not contain any of the consensus tyrosine kinase domain. Unlike trkB, where the truncated forms have a very short cytoplasmic tail, the cytoplasmic portion of truncated human trkC is 83 residues long. In addition, there is a very high degree of conservation among species in this region, suggesting that it may have an important function, perhaps serving as a signal to specify subcellular localization.

As has been described for rat trkC, there are forms of human trkC which contain an insert in the TK domain. Unlike the rat, where there are possible inserts of fourteen and twenty-five or thirty-nine amino acids, there appears to be only a fourteen amino acid insert possible at this site in the human. It is likely that these inserts play an important role in modulating the signalling cascade induced by ligand binding to trkC. Using PC12 cells expressing various forms of trkC as the assay system for signal transduction, it has been shown that expression of trkC with no insert in the TK domain confers on the expressing cells the ability to respond to NT3 with neurite outgrowth as well as NT3-induced autophosphorylation. Cells expressing trkC containing a TK insert are capable of ligand induced autophosphorylation, but do not respond to NT3 with neurite outgrowth. There are no differences yet described between the various inserts in this regard, but there are many downstream sequelae to neurotrophin binding and very few have been examined to date. This processing is tissue specific, as no evidence of the fourteen residue insert containing form was observed in human testis.

EXAMPLE 2

Expression Pattern of trk Receptors in Human Tissues

A. Northern Analysis

Probes used for Northern analysis were labeled using the PCR and the primers indicated in Table 1 on appropriate cloned template DNA. PCR reactions were run as described for initial cloning except that unlabeled dCTP was replaced in the reaction with gamma 32P dCTP at a concentration of 8 mCi/ml (3,000 Ci/mmole) and the reaction was only run for twenty cycles. Probes were separated from unincorporated nucleotides and boiled for five minutes before being added to Nytran blots containing 2 micrograms of poly A+ RNA per lane (Clontech, Palo Alto, Calif.) which had been prehybridized in 5× SSPE, 10× Denhardt's, 100 ug/ml salmon sperm DNA, 50% formamide, and 20% SDS. Hybridization was carried out at 50° C. in the same solution overnight and then blots were washed as for library filters but with the final wash at 50° C. Autoradiograms were obtained using a Fuji BAS2000 image analyzer after exposing the imaging plate for ten to twenty hours.

Results

Figure 6:
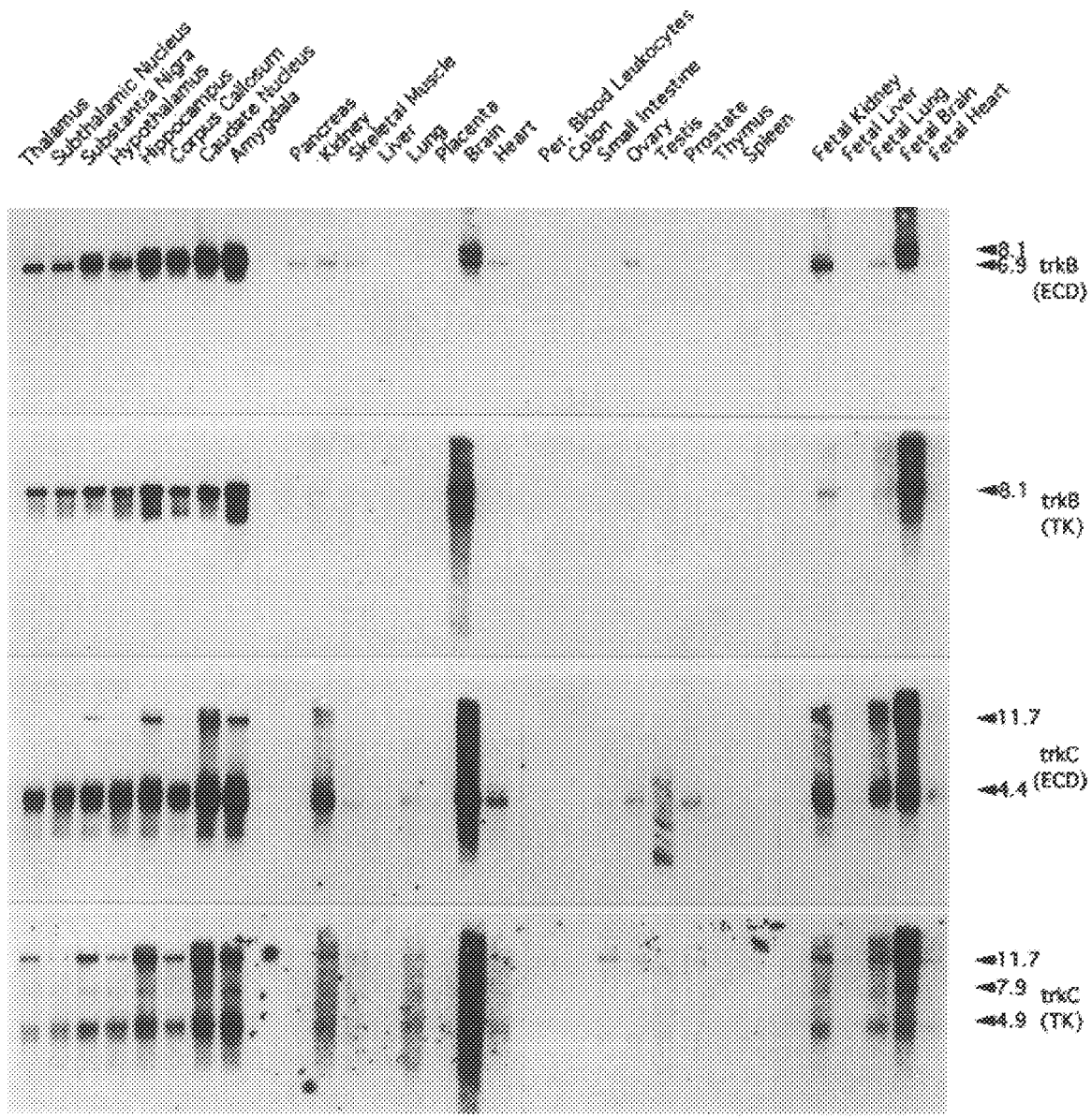
FIG. 6. Northern analysis of trk B and trkC expression in human tissues. Two micrograms of poly A+ RNA from the regions indicated was hybridized with probes specific for the trkB extracellular domain (ECD) or tyrosine kinase domain (TK) or the trkC extracellular (ECD) or tyrosine kinase (TK) domains. Note that the blot containing the brain regions was image processed differently than those containing the other tissues. In order to better display the range of hybridization signals present in the wide variety of tissues examined, a higher contrast setting was used for the brain regions hybridized with the trkB probes and a lower sensitivity was used for brain regions hybridized with the trkC probes.

The expression pattern and transcript size of the trks in human tissues was examined by using Northern analysis (FIG. 6). Hybridization with probes for trkB yielded an apparently simple pattern, with a transcript of 6.9 kb hybridizing to both an extracellular and TK specific probes, and a transcript of 8.1 kb hybridizing only to the TK specific probe. On the basis of this simple result, the 8.1 kb transcript presumably corresponds to the full length, TK-containing message, while the 6.9 kb transcript corresponds to message encoding the single truncated form seen in human. As might be expected from the greater number of potential splice variants detected while cloning trkC, probing Northerns for this molecule led to a more complex pattern of hybridization. Transcripts of 11.7, 7.9 and 4.9 kb were detected with a probe specific for the TK domain, while an additional transcript of 4.4 kb was detected with the extracellular domain probe (see FIG. 6).

Of the human tissues examined, both trkB and trkC were expressed in greatest abundance in the brain. However, there was expression in a variety of locations outside the nervous system in both adult and fetal tissues. The 8.1 kb transcript of trkB containing the TK domain was expressed in kidney, skeletal muscle and pancreas, while in heart, spleen and ovary expression of only the truncated form was detected. In fetal tissues, TK containing trk B was found not only in brain, but also in kidney and lung, while truncated trkB was found in brain, kidney, lung and heart. It was apparent that the ratio of TK-containing to truncated trkB transcripts was much higher in fetal than adult brain.

Although the highest expression level of trkC was in brain, there was widespread expression of trkC outside the nervous system. In the adult, TK containing trkC was expressed in kidney, skeletal muscle, lung, heart, small intestine, ovary, testis, and prostate, while in the fetus, the greatest expression was in brain, kidney, lung, and heart. The 4.4 kb transcript corresponding to the truncated form of trkC was detected in all tissues examined except peripheral blood leukocytes. Similar to the case for trkB, the ratio of TK containing to truncated trkC was higher in fetal compared to adult brain.

Discussion

Analysis of the transcripts for trkB using Northern blots showed a relatively simple pattern compared to that seen in the rodent. This is consistent with the idea that there is only a single main truncated form of trkB in the human. Analysis of the trk C showed a more complete pattern of transcript sizes, in keeping with the greater number of forms detected during sequence analysis of the clones. No evidence was seen for a transcript hybridizing with the kinase probe but not with the extracellular probe as has been described in rat trkC [Valenzuela et al., [1993], supra). In analyzing different tissues, the primary location of trkB and trkC expression was in the nervous system and specifically in the regions of the CNS. Unexpected was the finding that there is low level expression of trkB and trkC in a wide variety of tissues outside the nervous system. The levels of expression were quite low compared to those found in various regions of the brain, but still quite detectable above background. Some of the expression seen in certain tissues may be due to expression on elements of the nervous system sparsely scattered through the tissue. For example, expression of trkC in the small intestine may turn out to be due in whole or in part to expression by the neurons of the enteric nervous system. Final elucidation of this will have to await a detailed in situ hybridization analysis of tissues outside the nervous system.

B. In Situ Hybridization

In situ hybridization was carried out by a modification of a previously published procedure (Phillips et al., *Science* 250, 290–294 [1990]). Tissue was prepared for hybridization by a variety of techniques. Autolysis times on all samples were under 24 hours. Whole, unfixed embryos were embedded in OCT, frozen by floating the blocks in petri dishes on liquid nitrogen, and sectioned with the aid of a cryostat. Sections were thaw-mounted onto slides (superfrost plus, Fisher), air-dried, baked at 55° C. for 10 ", and stored in sealed boxes with desiccant at −70° C. until use. Adult dorsal root ganglia were fixed by immersion in 4% formaldehyde and either processed for paraffin sectioning or for crysosectioning. Brain specimens were fixed by immersion for 24 hours in 4% formaldehyde, cryoprotected for 24 hours in buffered sucrose, frozen on dry ice, and cut on a freezing sliding microtome. Sections were stored (less than 48 hours) in phosphate buffered saline at 4° C., mounted onto gelatin-subbed slides, air-dried, and stored at 4° C. Care was taken to avoid any condensation of moisture on all tissue sections during storage of the tissue.

On the day of hybridization, tissue sections were differentially pretreated according to the fixation and sectioning protocol employed to generate the sections. Unfixed tissue sections were fixed by immersion in 4% formaldehyde, 1% glutaraldehyde in 0.1M sodium phosphate for 30 " at 4° C., rinsed in 0.5× SSC (20× SSC is 3M NaCl and 0.3M sodium citrate), and placed directly into prehybridization solution. Cryosections of immersion-fixed tissue were fixed in 4% formaldehyde in 0.1M sodium phosphate for 5 minutes, rinsed 0.5× SSC, digested for 30 minutes at room temperature with proteinase-K (Boehringer-Manheim; 25 μg/ml in 0.5M NaCl and 10 mM Tris, pH 8.0), rinsed, refixed for 10 minutes in 4% formaldehyde, dehydrated in a series of alcohols (50% ethanol containing 0.3% ammonium acetate; 70% ethanol containing ammonium acetate; 100% ethanol; 2 minutes per incubation), rehydrated through the same series of ethanols, and rinsed again in 0.5× SSC prior to prehybridization. For paraffin-embedded tissue, deparaffinzation was performed by 2 rinses in xylene (2 " each), after which tissue was rehydrated through a series of alcohol solutions ( 100% ethanol twice, 95% ethanol, 70% ethanol; 2 " each). Tissue sections were then fixed in 4% formaldehyde for 10 ", digested for 30" with proteinase k (25 or 50 ug/ml ; room temperature or 37° C.), rinsed, refixed for 10", and rinsed again in 0.5× SSC prior to prehybridization.

Prehybridization, hybridization, and posthybridization RNAase treatment and stringency washes were identical for all tissues carried out as previously described (Phillips et al, 1990).

Figure 7A:
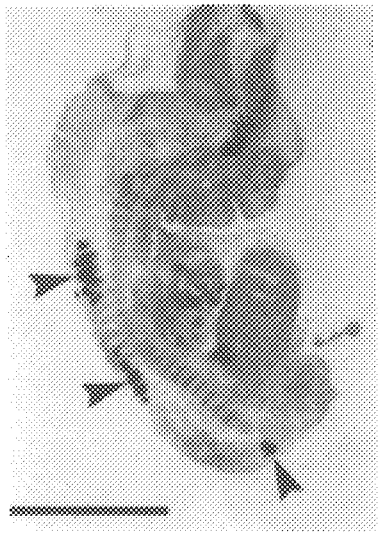
FIGS. 7A–7E. In Situ hybridization analysis of embryos and adult brain. In situ hybridization using probes for trkA (FIGS. 7A and 7D) TK-containing trkB (FIG. 7B) and TK-containing trkC (FIGS. 7C and 7E). Shown are sheet film autoradiographs of sagittal sections of eight week old human embryos (FIGS. 7A, 7B and 7C) with arrowheads pointing to developing DRG and asterisks signifying trigeminal ganglion.
Figure 7B:
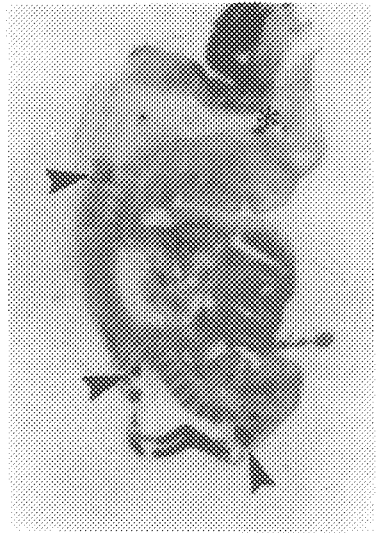
Figure 7C:

In situ hybridization with probes to human trkA, and the TK-containing forms of trkB, and trkC was conducted on a limited series of embryonic and adult human tissue prepared by a variety of protocols. In two embryos of 6 & 8 weeks gestation (fresh-frozen), trkA expression was restricted to dorsal root and cranial sensory ganglia, including the trigeminal ganglion (FIG. 7A). In contrast, trkB and trkC were not only expressed in sensory ganglia, but prominent expression was also seen within the developing brain and spinal cord (FIGS. 7B & C). In addition, trkC expression was observed in the developing vasculature.

Results

Figure 9E:
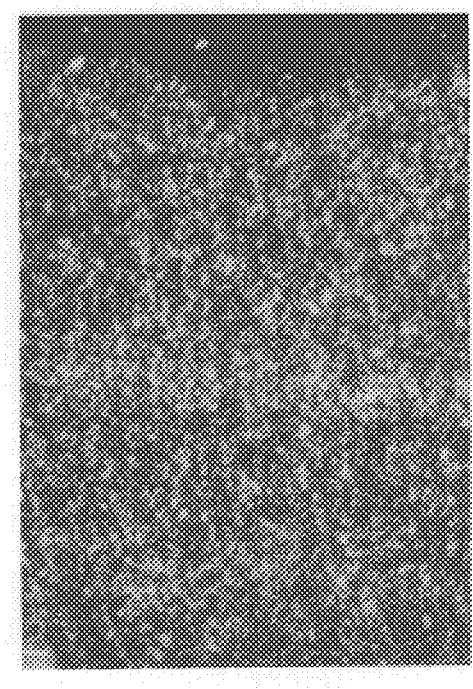
Figure 9F:
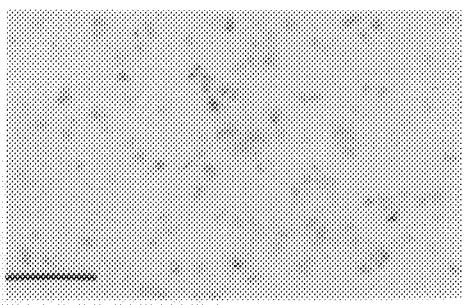
Figure 9G:
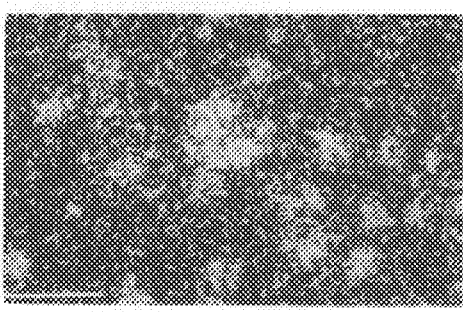

Within developing dorsal root ganglia, trkC was strongly expressed in ganglia from both the 6 and 8 week embryos. Curiously, in both embryos, there was a marked tendency for trkC-expressing cells to localize in the ventral end of the ganglia (FIGS. 8A–8F). In contrast, trkA positive cells were largely restricted to dorsal portions of the ganglia (FIGS. 8A–8F). In adult dorsal root ganglia (paraffin-embedded or cryosectioned fixed tissue), a subpopulation of DRG neurons was labelled with each of the three trk probes (trkB, FIGS. 9B & C; trkA and C data not shown). Cells labelled with probes to each of the three trks appeared to be randomly distributed throughout the ganglia. No labelling of non-neuronal cells was observed with any of the probes.

Figure 7D:
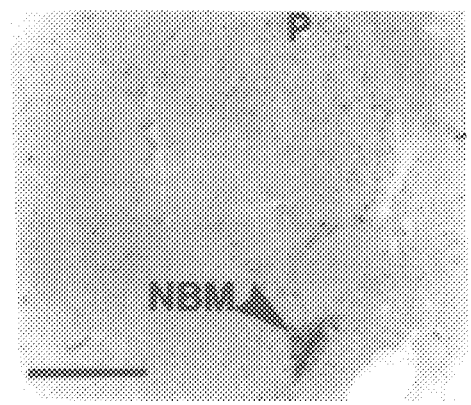
Figure 7E:
Figure 8A:
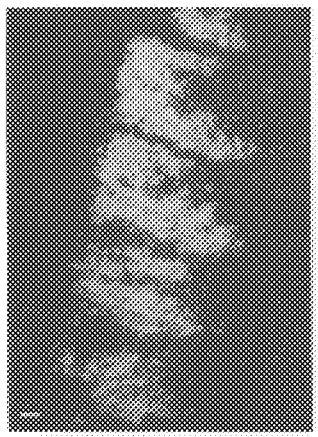
FIGS. 8A–8F. In situ hybridization of developing DRG with trkA and trkC. Emulsion autoradiography of developing DRG from human embryos hybridized with probes for trkA (FIGS. 8A, 8B, and 8C) and trkC (FIGS. 8D, 8E, and 8F). Ventral is to the right in all panels, and scale bars are 100 microns.
Figure 8B:
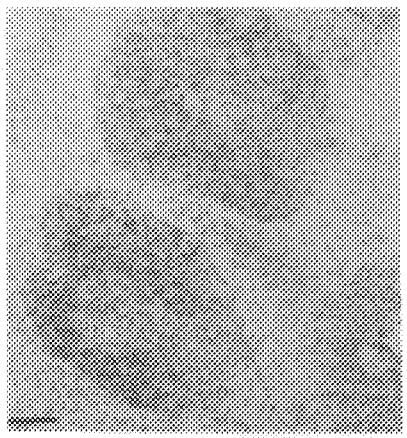
Figure 8C:
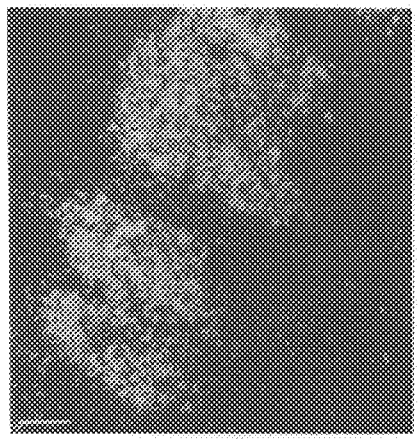
Figure 8D:
Figure 8E:
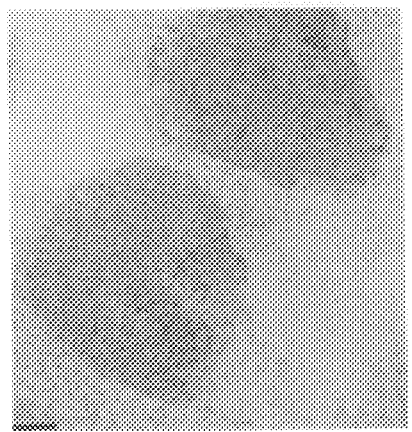
Figure 8F:
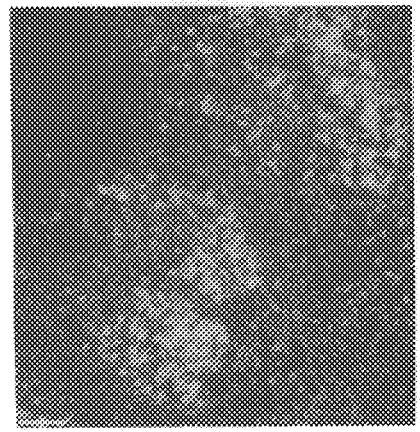

In the adult human forebrain (fixed, cryosectioned tissue), cells strongly labelled for trkA expression were observed in the nucleus basalis of Meynert and scattered throughout the head of the caudate nucleus (FIG. 7D). Labelled cells were of large diameter and conform to the expected appearance of cholinergic cells (FIG. 9A). trkC was widely expressed throughout the human forebrain, including prominent expression in hippocampus and neocortex (FIGS. 7E; 9D & E) and labelled cells appeared to be exclusively of neuronal morphology (FIGS. 9A–9G).

Discussion

The in situ hybridization analysis of the expression of the members of the trk family in the human nervous system confirmed that the overall expression pattern is similar to that seen in other mammals. This should provide a foundation for further studies designed to examine the expression of the differently spliced forms of the human trks in detail in certain areas of normal and pathological tissues. In this regard, given the difficulty of obtaining human tissue, it is encouraging that the in situ hybridization was performed on tissues handled in a variety of ways post mortem. Sections were cut unfixed, fixed and frozen, and fixed and paraffin-embedded, and all of these methods yielded useful results. One unexpected finding was the apparent polarization of the developing human DRG, with trkA cells predominant in the dorsal and trkC expressing cells predominant in the ventral area of the developing ganglia. This polarization of trk expression was not apparent in sections from the adult human DRG or in rat embryos hybridized with rat trkA and trkC probes (data not shown).

EXAMPLE 3

Expression of trk Immunoadhesins

A. Construction of trk-Ig immunoadhesins

Using protein engineering techniques, the human trks were expressed as chimeras of trk extracellular domain with the Fc domain of human IgG heavy chain. DNA constructs encoding the chimeras of trk extracellular domain and IgG-1 Fc domains were made with the Fc region clones of human IgG-1 (Ashkenazi et al., *Immunoadhesins Intern. Rev. Immunol.* 10, 219–227 [1993]). More specifically, the source of the IgG-1 encoding sequence was the CD4-IgG-1 expression plasmid pRKCD4$_2$Fc$_1$ (Capon et al., *Nature* 334, 525 [1989]; Byrn et al., *Nature* 344, 667 [1990]) containing a cDNA sequence encoding a hybrid polypeptide consisting of residues 1–180 of the mature human CD4 protein fused to human IgG-1 sequences beginning at aspartic acid 216 (taking amino acid 114 as the first residue of the heavy chain constant region (Kabat et al., *Sequences of Proteins of Immunological Interest* 4th ed. [1987]), which is the first residue of the IgG-1 hinge after the cysteine residue involved in heavy-light chain bonding, and ending with residues 441 to include the CH2 and CH3 Fc domains of IgG-1.

The CD4-encoding sequence was deleted from the expression plasmid pRKCD4$_2$Fc$_1$ and the vector was fused to DNA encoding the trk receptors, with the splice between aspartate 216 of the IgG-1 and valine 402 of trkA, threonine 423 of trkB numbering from the translation start methionine or threonine 413 of trkC deleted variant, numbering from the translation start methionine. DNAs encoding whole receptor or IgG chimeras were subcloned into pRK for transient expression in 293 cells using calcium phosphate (Suva et al., *Science* 237, 893–896 [1987]). For purification of trk-IgG chimeras, cells were changed to serum free media the day after transfection and media collected after a further two to three days. Media was filtered, bound to a protein A column (Hi-Trap A, Pharmacia), the column washed with PBS, bound protein eluted with 0.1M glycine, pH 3.0, and immediately neutralized with tris buffer. Concentration was estimated by absorbance at 280 nm using an extinction coefficient of 1.5. SDS-PAGE analysis showed the resulting protein to be a single detectable band.

Cells transiently transfected with these DNA constructs secreted protein which bound to protein A and migrated with an approximate molecular weight of 125 kD on reducing SDS-polyacrylamide gels. Purified trk-IgG chimeras could be easily isolated from conditioned media in a single round of affinity chromatography on a protein A column. Sequence analysis of these purified proteins verified the predicted signal sequence cleavage site, and resulting N-termini (data not shown).

B. Binding assays

Figure 10A:
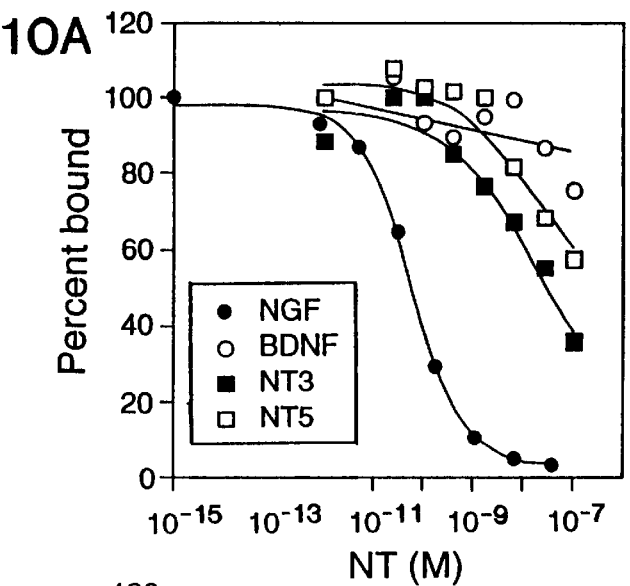
FIGS. 10A–10C. Competitive displacement of neurotrophins bound to trk-IgG. Radiolabelled neurotrophins (25 to 35 pM) were bound to trk-IgG in the presence of increasing concentrations of various unlabelled neurotrophins.
Figure 10B:
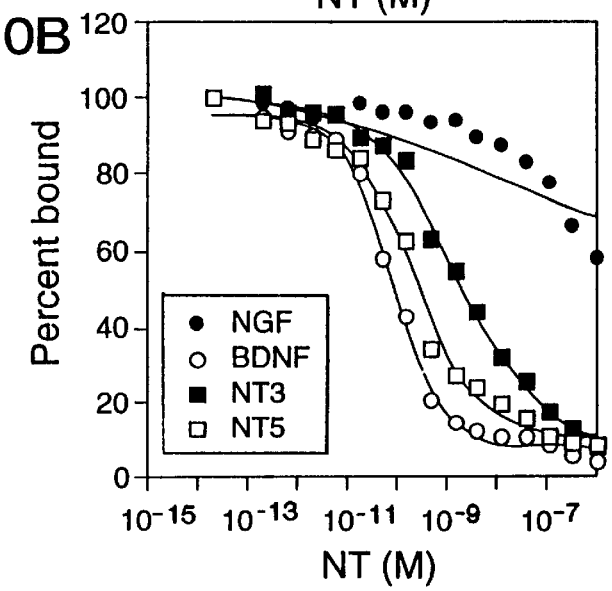
Figure 10C:
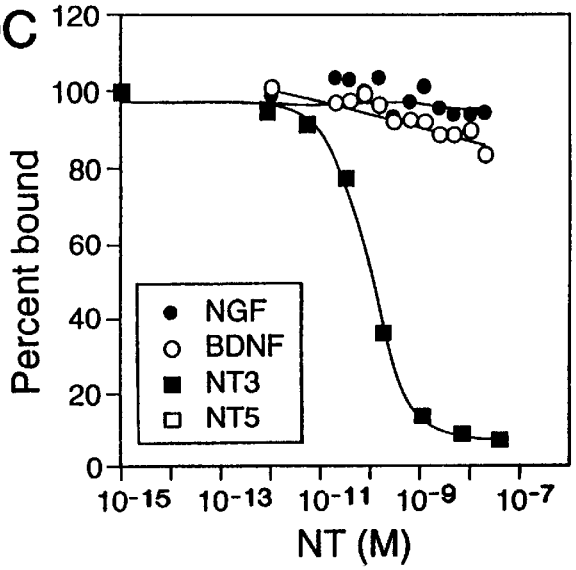

In order to test whether these chimeric proteins retained the binding specificity expected of the trk extracellular domain in a cellular environment, competitive displacement assays were done with iodinated neurotrophins. As can be seen from the results shown in FIG. 10, the trk-IgG chimeras did show specific binding to the expected neurotrophin(s). Chimeras containing trkA extracellular domain bound NGF well and NT3 and NT5 with much lower affinity. Chimeras containing trkB bound BDNF and NT5 well but only slightly better than NT3, and showed almost no detectable binding to NGF. Chimeras containing trkC were highly specific for NT3 over the other neurotrophins. The apparent affinity of the chimeras for their preferred ligand as determined in these competitive displacement assays is in the range of that determined for the majority of the binding sites on cells transfected with and expressing the various trk proteins. In one experiment, the IC50s obtained for trkA were 62 pM for NGF and 20 nM for NT3, for trkB were 81 pM for BDNF, 200 pM for NT4/5 and 18 nM for NT3 and for trkC was 95 pM for NT3. The ratio of specific to nonspecific binding are quite high in assays done with these reagents, usually at least ten to one (see FIGS. 10A–10C).

Figure 11A:
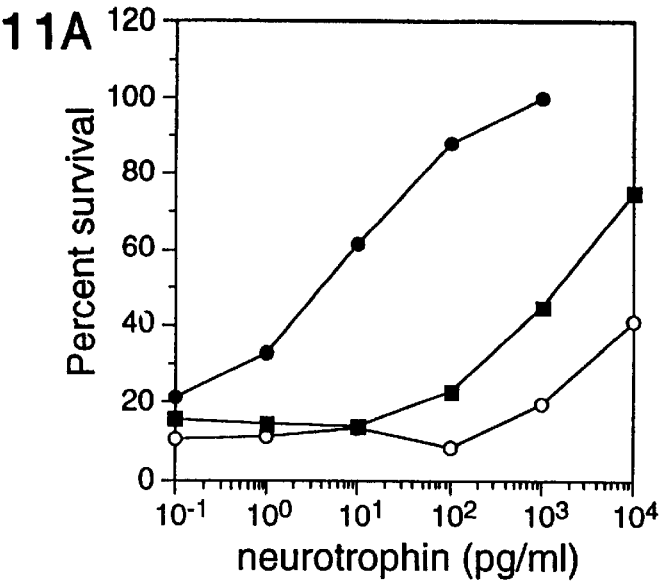
FIGS. 11A–11C. Neurotrophin bioactivity is blocked by trk immunoadhesins. Neurotrophin bioactivity was assessed by measuring the survival of chick dorsal root (FIGS. 11A and 11B) or sympathetic (FIG. 11C) ganglion neurons in the absence or presence of trk immunoadhesins.
Figure 11B:
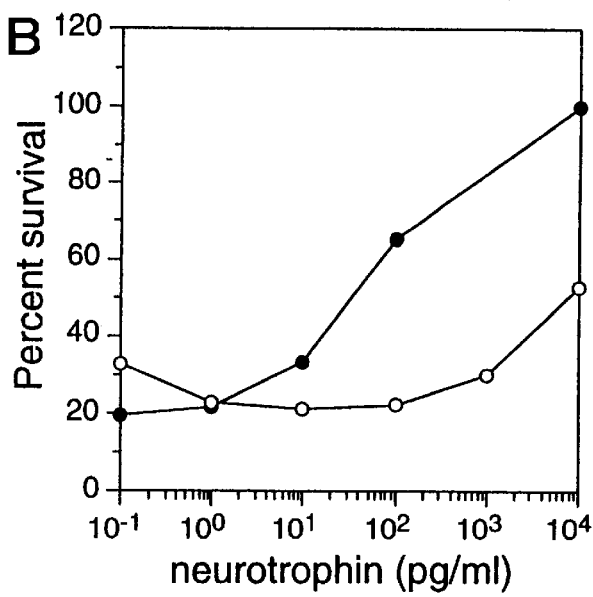
Figure 11C:
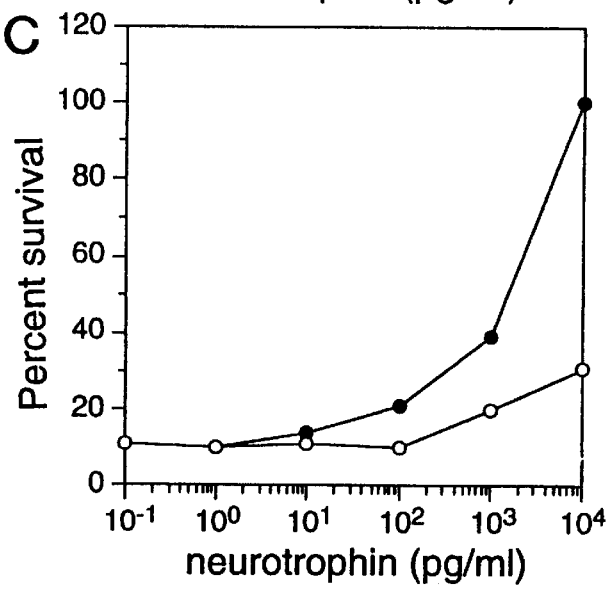

To check whether the trk-IgG chimeras might be capable of blocking the biological activity of their cognate ligands, the neurotrophin induced survival of peripheral neurons was assayed in the presence of the appropriate trk-IgG chimera. As can be seen in FIGS. 11a–11C, trkA-IgG is a potent inhibitor of NGF biological activity, trkB-IgG of BDNF, and trkC-IgG of NT3. In all cases, addition of excess neurotrophin is capable of overcoming this blockade, indicating that the trk-IgG chimeras are not generally toxic to the neurons.

The binding data presented here demonstrates that the trk-IgG fusions bind neurotrophins with a selectivity and affinity similar to that seen by expression of the whole receptor in cells. The binding assays as reported here are very simple to do in large numbers, have excellent reproducibility and low background, and retain the specificity of the native trks. These qualities have proven quite valuable in analyzing the binding characteristics of mutant neurotrophins (Laramee et al., High resolution mapping of NGF-trkA and p75 receptor interactions by mutagenesis.

In addition to their utility in analyzing the binding of neurotrophins, the trk-IgG chimeras are useful inhibitors of the biological activity of their cognate neurotrophin. All of the experiments shown here have been performed in in vitro systems, but preliminary experiments indicate that trkA-IgG is capable of inhibiting NGF activity in vivo as well (data not shown). This will fill an unmet need for the trkB and trkC chimeras, as it has been difficult to raise good blocking antisera to BDNF, NT3 and NT4/5.

With the information in hand about the forms of trk present in human, it is possible to begin to investigate the expression of these forms in the normal and diseased state. Knowledge of the expression levels of the entire spectrum of forms of each trk will be crucial, as the different forms can display different and sometimes counteracting signal transduction properties in response to neurotrophins. In addition, the availability of soluble forms of the human trks should, by allowing the blocking of endogenous bioactivity, accelerate the investigation of the biology of neurotrophins in vivo.

EXAMPLE 4

Mutagenesis of Human trkC

Mutagenesis studies were performed in order to determine which amino acids of the extracellular domain of the trkC protein determine affinity and specificity to the neurotrophin NT-3. The three-dimensional structure of trkC is unknown, however, a putative domain organization was proposed. According to this model, the extracellular domains of the trk family of proteins are built up by five domains. Proceeded by a signal sequence, the domains are: a first cysteine-rich domain, a leucine-rich domain, a second cystein-rich domain, and two immunoglobulin-like domains.

Figure 12:
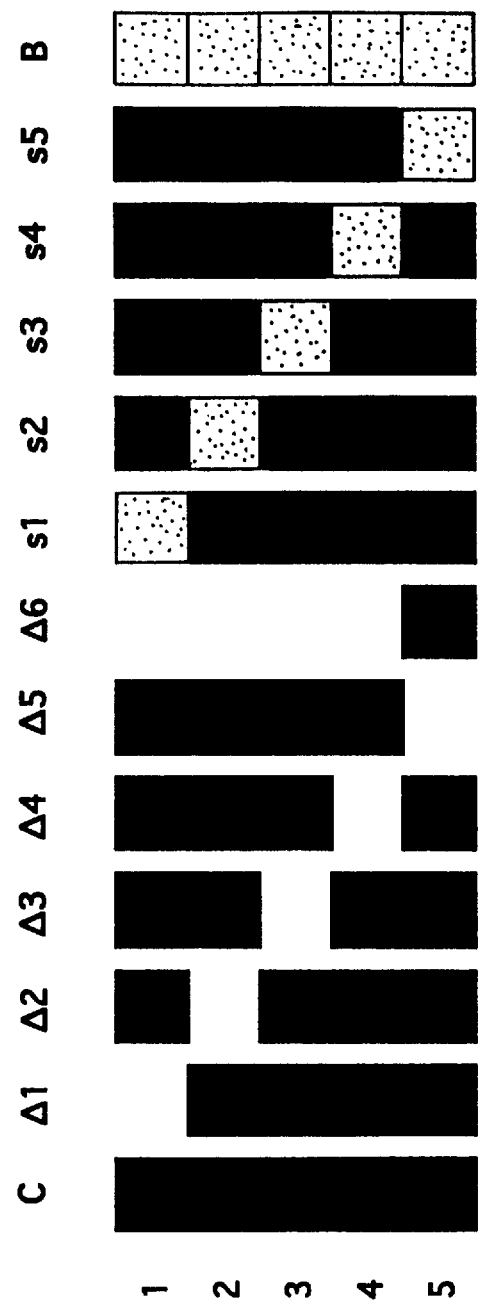
FIG. 12. Structures of trkC deletions and swaps with trkB. Structural domains of trkC and trkB in black and grey, respectively.
Figure 13:
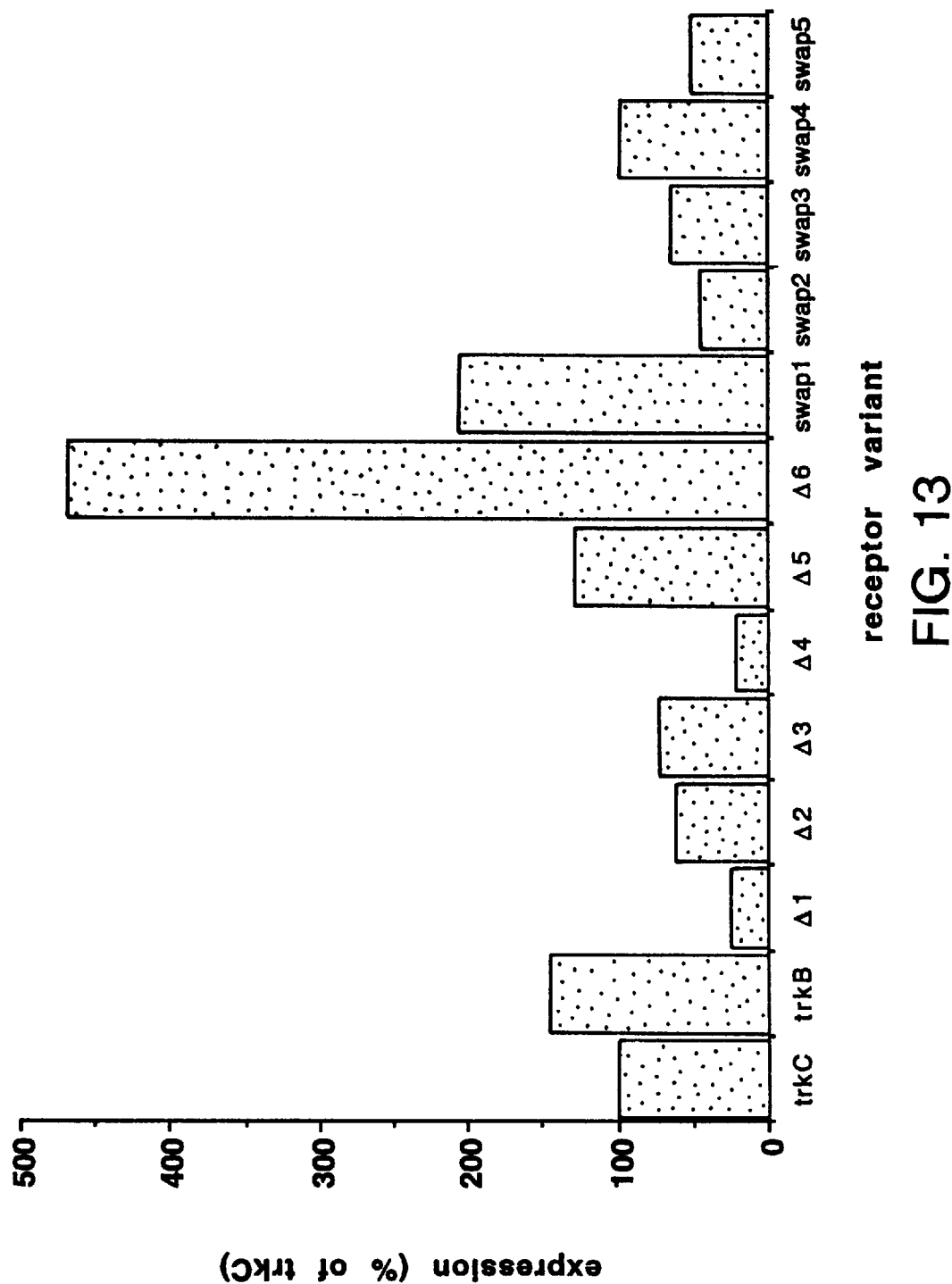
FIG. 13. Expression of trkC deletions and swaps with trkB. One particular representative experiment is shown. Concentrations were determined using an anti-Fc ELISA. Values of trkC variants are expressed as percentage of trkC wild-type expression.

In order to investigate the function of the trkC receptor domains, five trkC variants were constructed, lacking each of the five domains individually (Δ1–Δ5) and one variant where all domains except the second immunoglobulin-like domain are deleted (Δ6). The structures are illustrated in FIG. 12. In addition to these variants, also all five domains were exchanged individually by the corresponding trkB sequence (s1–s5) in order to determine the remaining affinity to NT-3 and to test for recruitment of BDNF binding. All trkC variants, including the trkC, trkB chimeras, were studied in the form of immunoadhesins. The immunoadhesins were constructed on the analogy of the process described in Example 3, and expressed in the human embryonic kidney cell line 293, using a pRK5 (EP 307,247) or pRK7 vector. pRK7 is identical to pRK5 except that the order of the endonuclease restriction sites in the polylinker region between ClaI and HindIII is reversed. (See U.S. Pat. No. 5,108,901 issued 28 Apr. 1992). The proteins were secreted into serum free medium, 20× concentrated and quantified with an anti-Fc ELISA assay. The results of a typical expression are presented in FIG. 13. Variants of particular interest, trkC, Δ6, Δ5, s5 and trkB were purified to homogeneity over Protein A using standard protocols. The N-terminal sequences of these variants were determined and were as predicted.

Figure 14A:
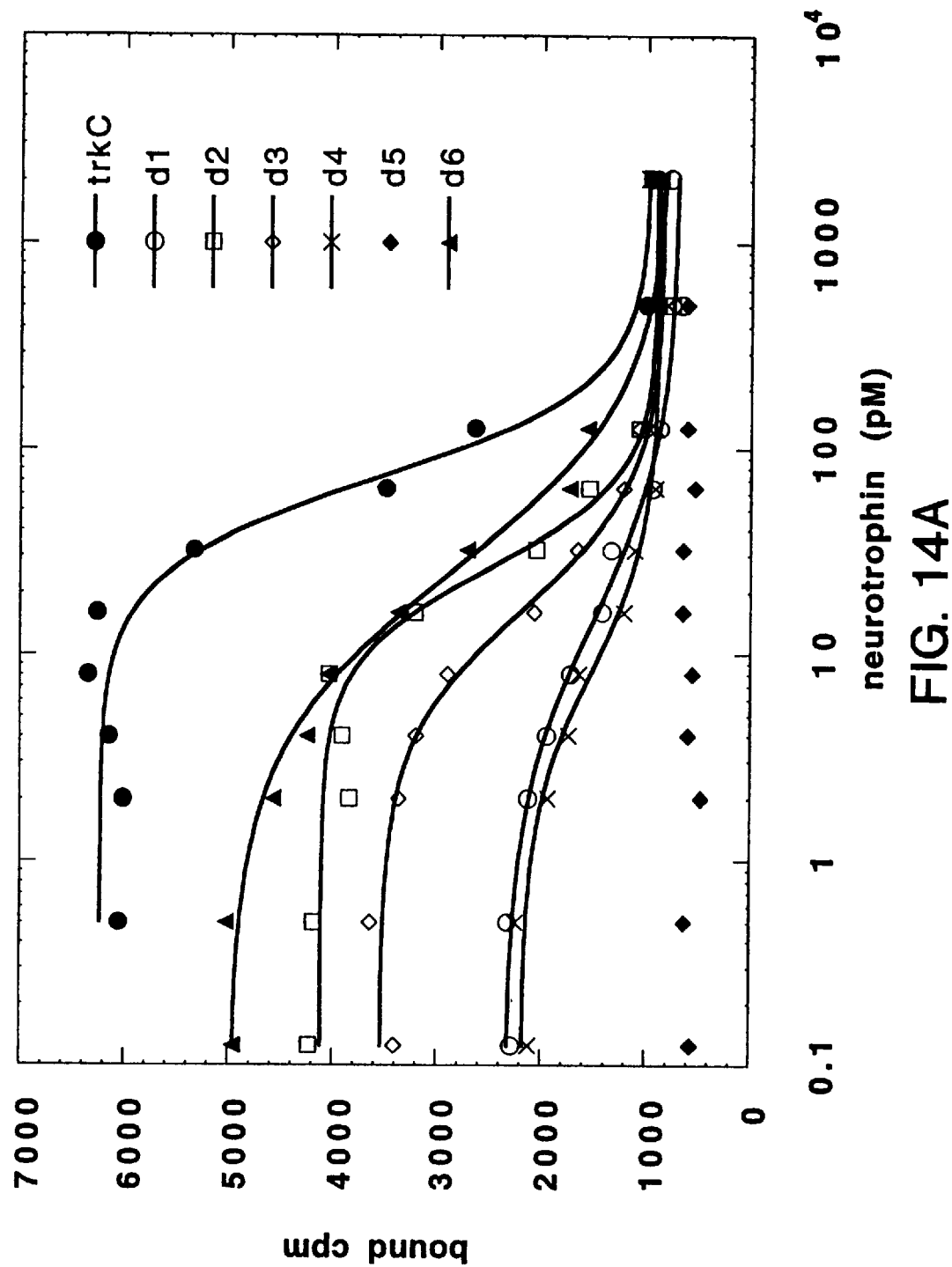
FIGS. 14A–14C. Competitive displacement of NT-3 bound to trkC variants. Radiolabeled NT-3 (50 pM) was bound to trkC variants in the presence of increasing amounts of unlabeled NT-3.
Figure 14B:
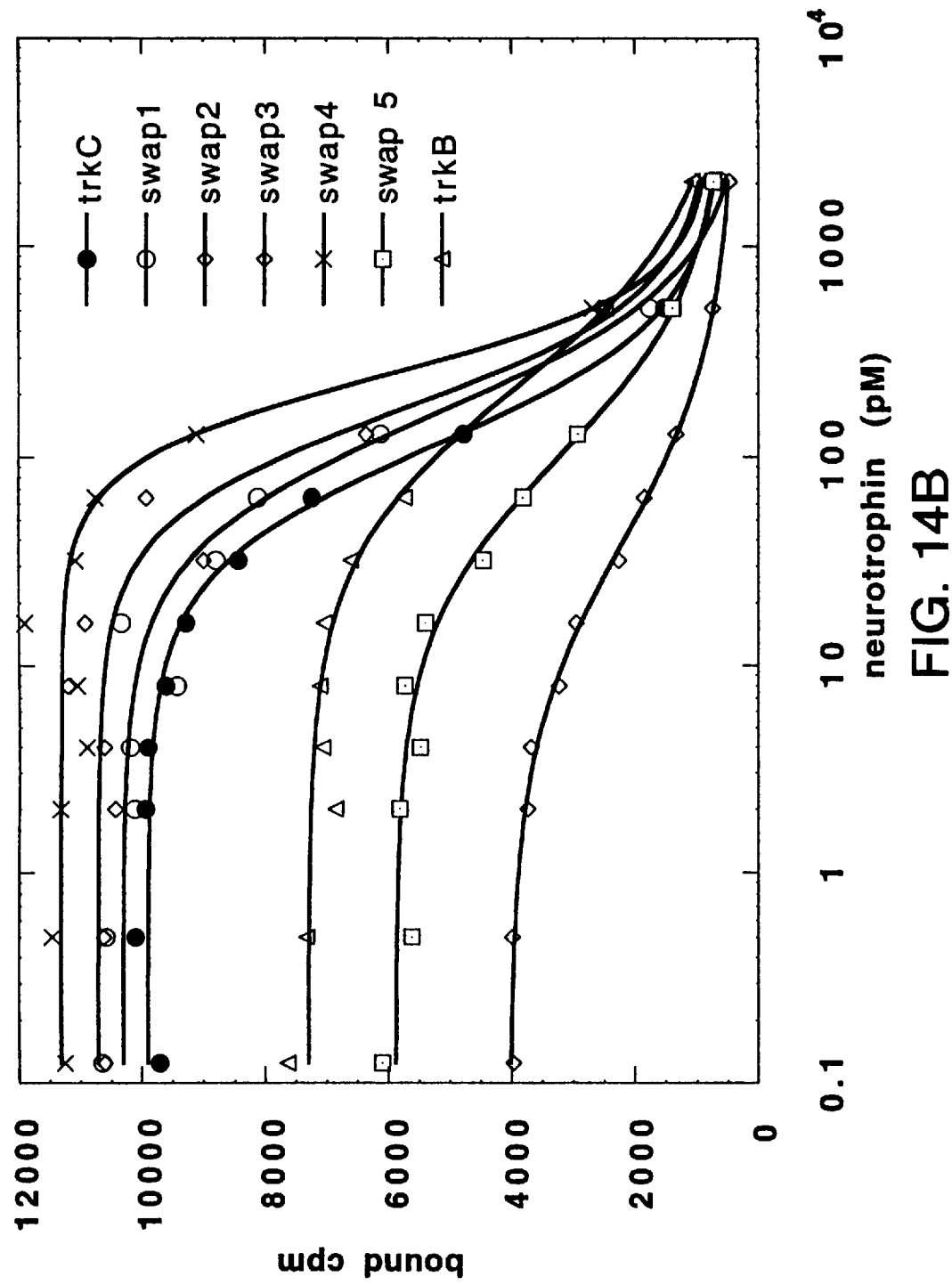
Figure 14C:
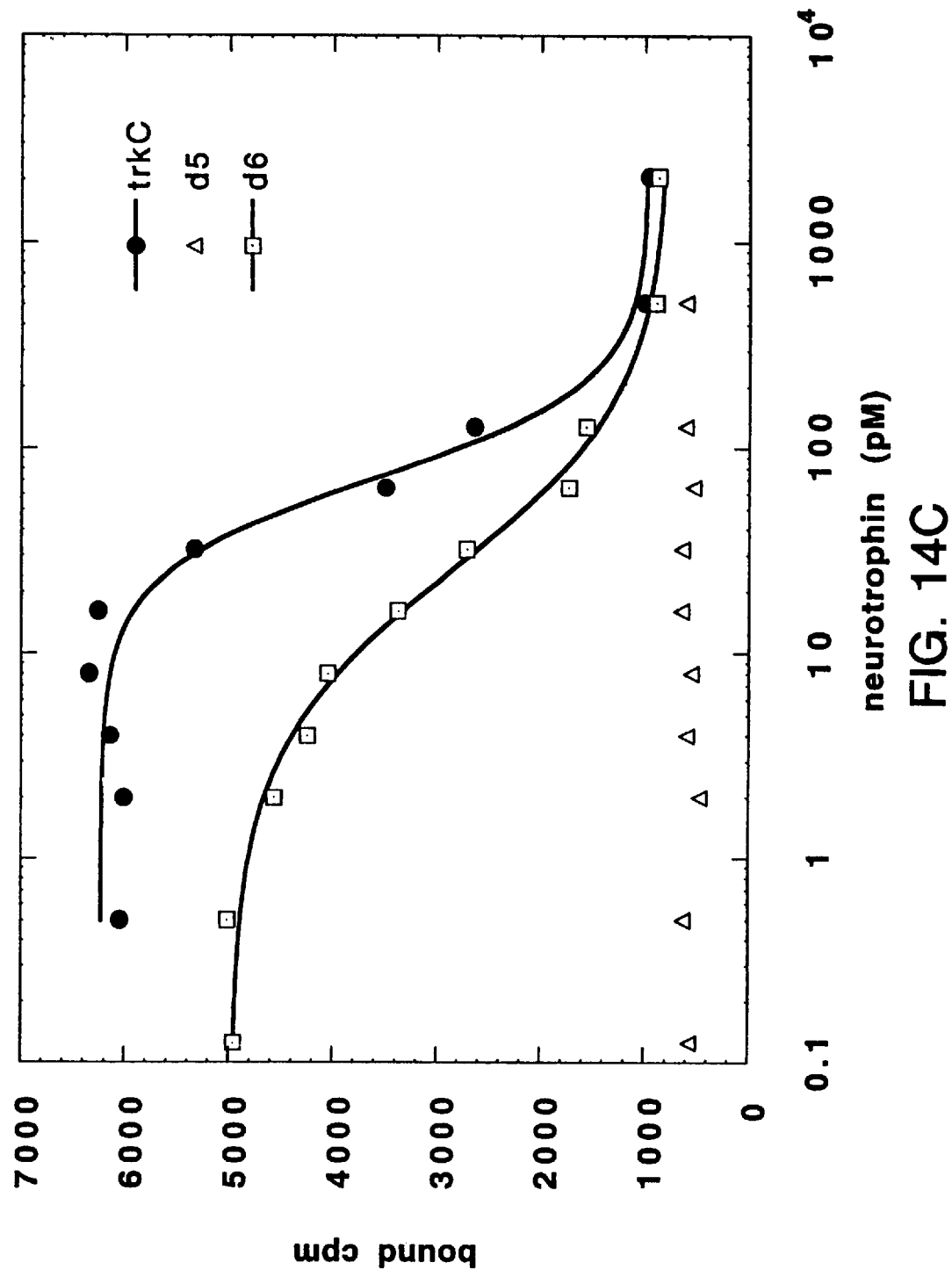

All receptor variants were tested for their ability to bind labeled NT-3 in competitive displacement assays using standard immunoadhesion technology. All the fusions and swaps were still able to bind NT-3 with similar affinity as trkC with the exception of Δ5. Although the total bound labeled NT-3 for several variants was low (i.e. Δ1, Δ4, s2), the IC-50 values were all close to the trkC value (FIGS. 14A and 14B). Most importantly, the variant Δ6, which lacks all but the second immunoglobulin-like domain, retained most of the binding capability of the trkC full length receptor. In addition, deletion of this domain in Δ5 leads to a molecule that is not able to bind NT-3 at all (FIG. 14C).

Figure 15A:
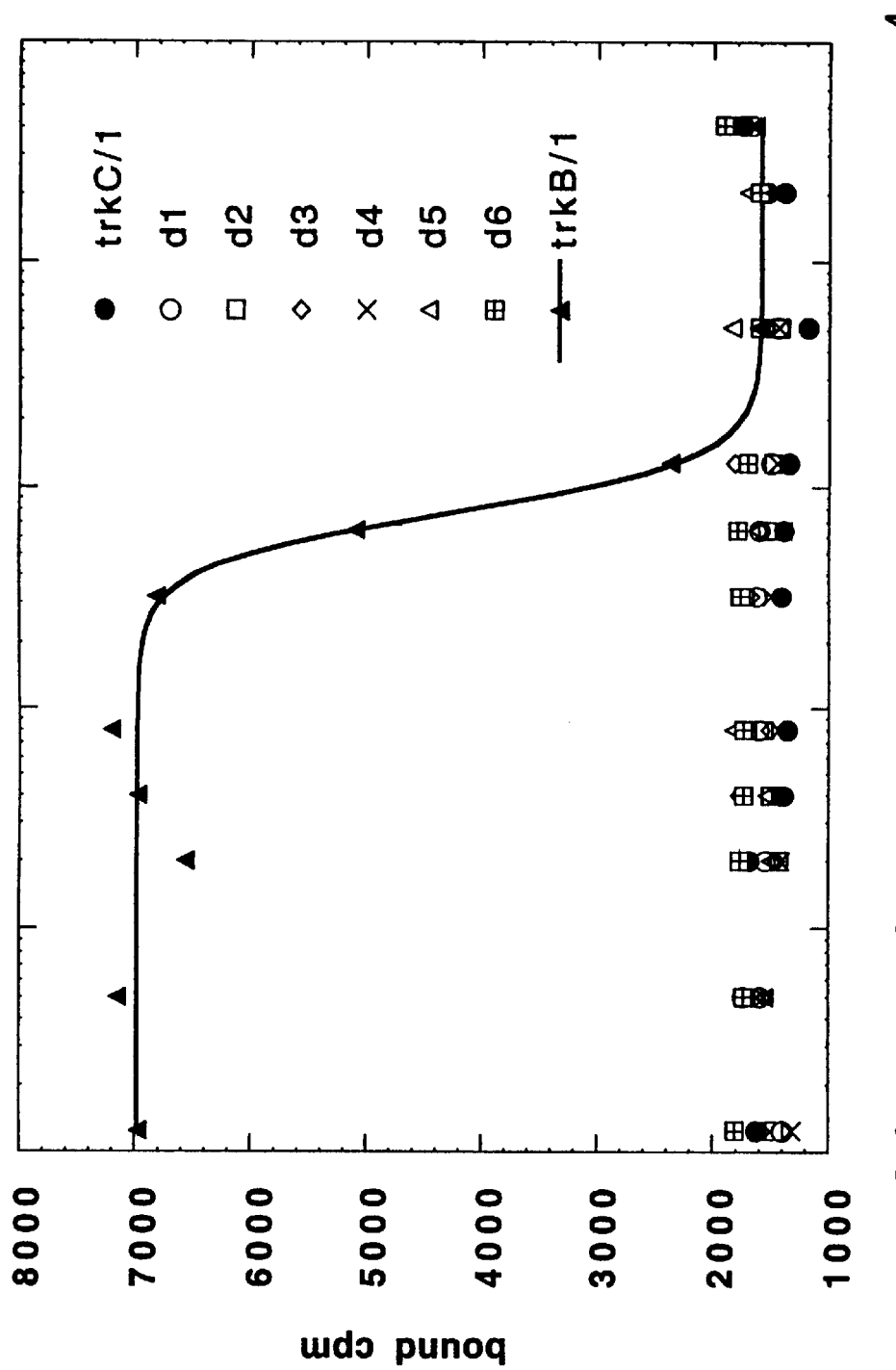
FIGS. 15A–15C. Competitive displacement of BDNF bound to trkC variants. Radiolabeled BDNF (50 pM) was bound to trkC variants in the presence of increasing amounts of unlabeled BDNF.
Figure 15B:
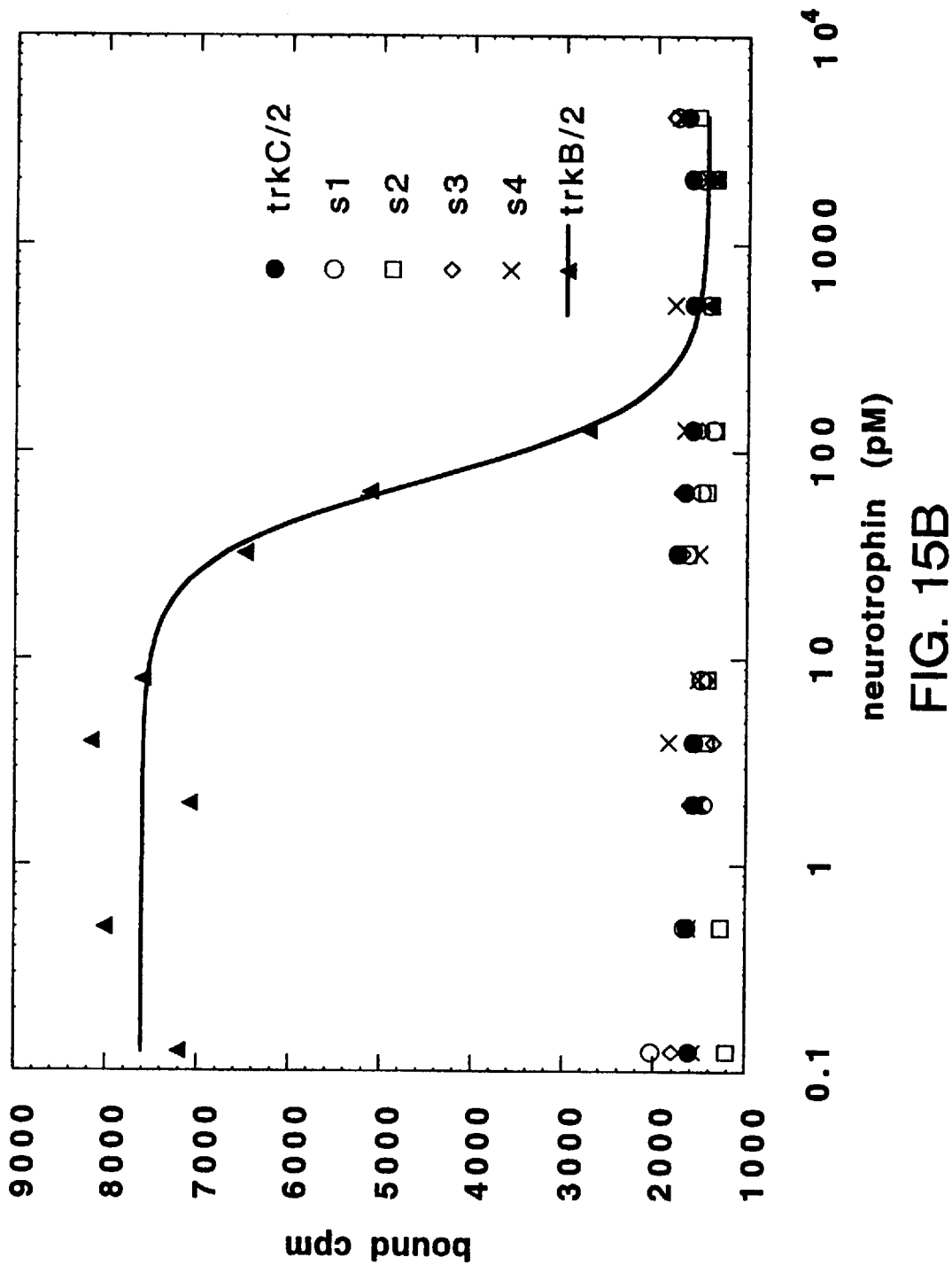
Figure 15C:
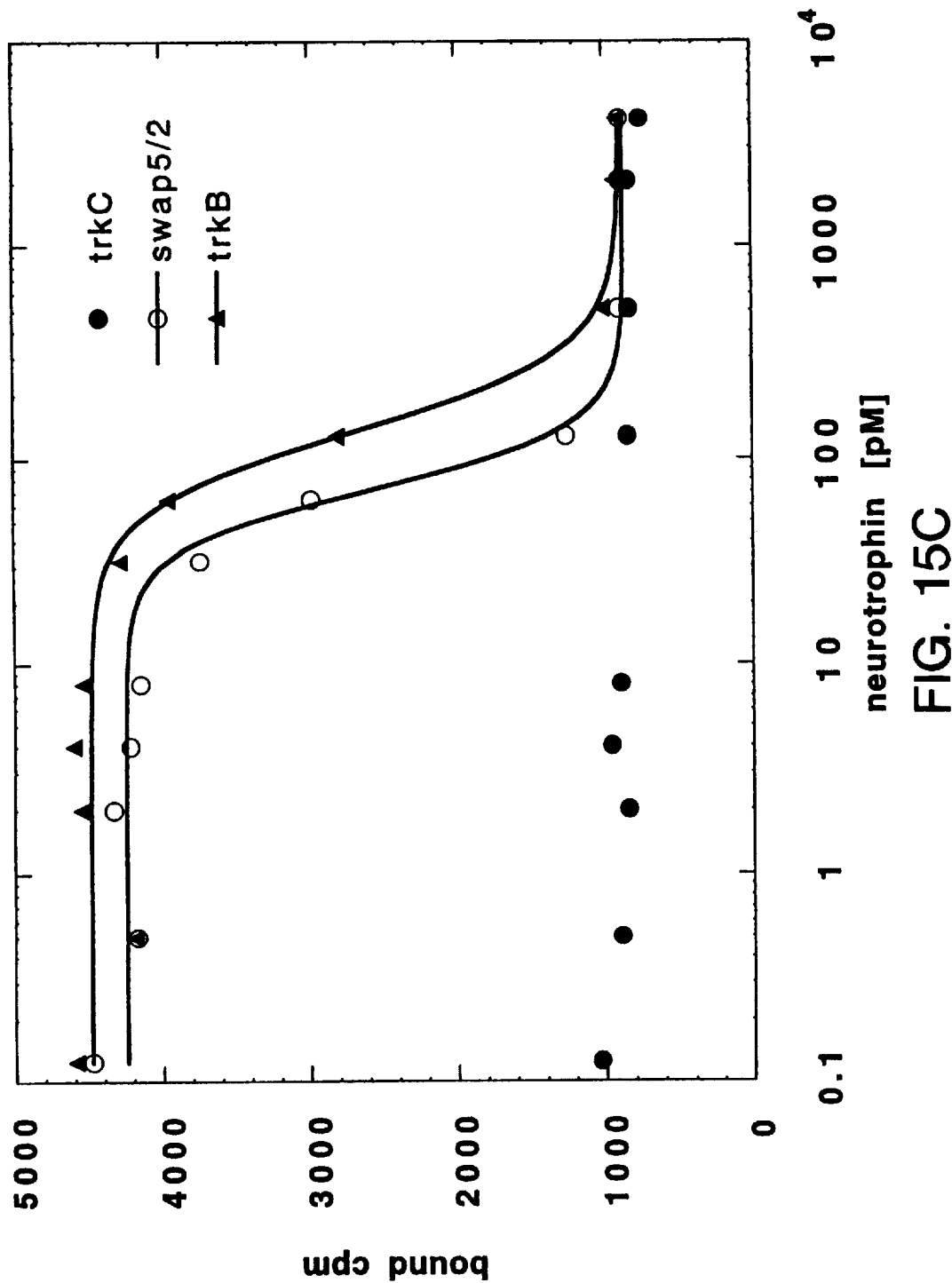
Figure 17:
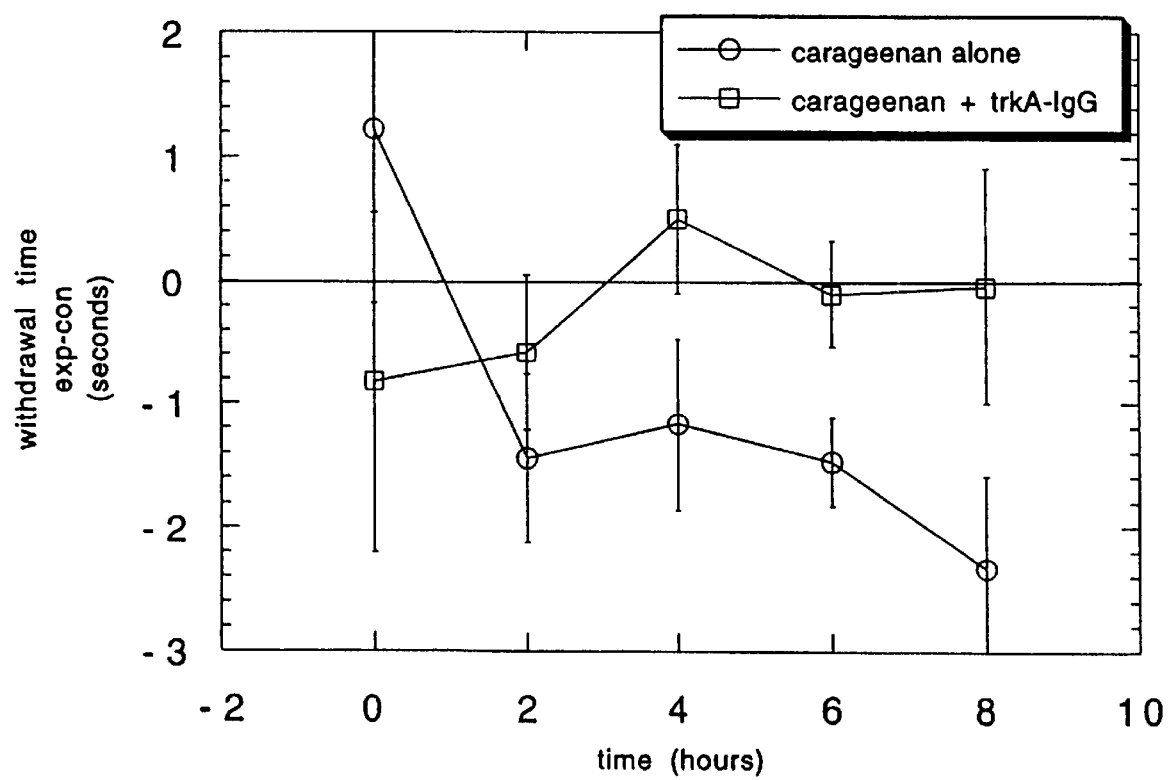
FIG. 17. Effect of a trkA-IgG immunoadhesin on carageenan induced hyperalgesia in rats.

All receptor variants were tested for their ability to bind labeled BDNF in competitive diplacement assays using the same type of assay as for the NT-3 binding. Note that trkC is not able to bind BDNF. All variants but one failed to bind BDNF (FIGS. 15A–C). The only variant which bound BDNF was swap5 where the second immunoglobulin-like domain of trkC is exchanged by the one of trkB (FIG. 15C). This variant bound BDNF as well as the trkB full length receptor.

trkA-IgG chimera prepared in Example 3 was injected into one hind paw of four adult male Wistar rats at time zero. The latency of withdrawal to a noxious heat stimulus was measured for each hind paw in triplicate every two hours thereafter. The paw injected with carageenan alone showed distinct inflammation and hyperalgesia (decreased latency to withdrawal compared to contralateral control paw) within two hours. Rats injected with carageenan plus trkA-IgG showed distinct inflammation, but showed no evidence of hyperalgesia compared to the contralateral control paw. Pooled data from carageenan alone vs. carageenan plus trkA-IgG at four, six and eight hour time points is significantly different at p >0.02 (see FIG. 17).

B. trkA-IgG immunoadhesin leads to hypoalgesia

Figure 18:
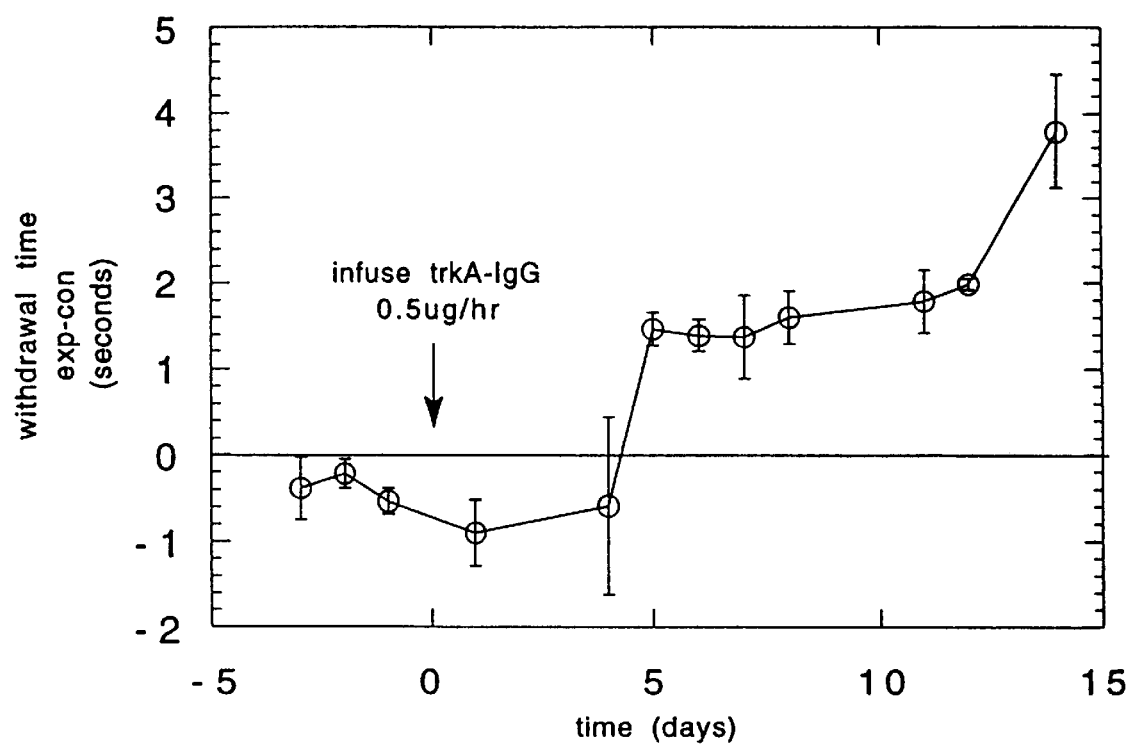
FIG. 18. TrkA-IgG infusion leads to hypoalgesia in rats.

The trkA-IgG immunoadhesin was infused continuously under the skin of the dorsolateral surface of one hind paw of four adult male Wistar rats at a rate of 0.5 μg/hr. Latency of withdrawal of control and infused paws was determined in triplicate at various times thereafter., After five days of infusion, there was a pronounced hypoalgesia on the infused side when compared to the control side. Withdrawal time difference of all time points five days and after significantly differed from the pooled preinfusion time difference at p>0.05 (see FIG. 18).

TABLE 1

| USE | trkA | trkB | trkC |
|---|---|---|---|
| degenerate sense | | TGYGAYATHATGTGGYTNAARAC SEQ. ID. NO: 10 | TGGATGCARYTNTGGCARCARCA SEQ. ID. NO: 11 |
| degenerate anti | | YTCRTCYTTNCCRTAYTCRTT SEQ. ID. NO: 12 | CCYTCYTGRTARTAYTCNACGTG SEQ. ID. NO: 13 |
| ECD insert sense | CACGTCAACAACGGCAACTACA SEQ. ID. NO: 14 | GGAAGGATGAGAAACAGATTTCTGC SEQ. ID. NO: 15 | CATCAATGGCCACTTCCTCAAGG SEQ. ID. NO: 16 |
| ECD insert anti | AGGTGTTTCGTCCTTCTTCTCC SEQ. ID. NO: 17 | GAGATGTGCCCGACCGGTTGTATC SEQ. ID. NO: 18 | CACAGTGATAGGAGGTGTGGGA SEQ. ID. NO: 19 |
| TK insert sense | GGATGTGGCTCCAGGCCCC SEQ. ID. NO: 20 | GGGCAACCCGCCCACGGAA SEQ. ID. NO: 21 | ACGCCAGGCCAAGGGTGAG SEQ. ID. NO: 22 |
| TK insert anti | TAACCACTCCCAGCCCCTGG SEQ. ID. NO: 23 | TTGGTGGCCTCCAGCGGCAG SEQ. ID. NO: 24 | AATTCATGACCACCAGCCACCA SEQ. ID. NO: 25 |
| Probes | | | |
| ECD sense | GCTCCTCGGGACTGCGATGC SEQ. ID. NO: 26 | ATGTCGCCCTGGCCGAGGTGGCAT SEQ. ID. NO: 27 | AAGCTCAACAGCCAGAACCTC SEQ. ID. NO: 28 |
| ECD anti | CAGCTCTGTGAGGATCCAGCC SEQ. ID. NO: 29 | CCGACCGGTTTTATCAGTGAC SEQ. ID. NO: 30 | ATGATCTTGGACTCCCGCAGAGG SEQ. ID. NO: 31 |
| TK specific sense | | CTTGGCCAAGGCATCTCCGGT SEQ. ID. NO: 32 | ATGTGCAGCACATTAAGAGGA SEQ. ID. NO: 33 |
| TK specific anti | | TTATACACAGGCTTAAGCCATCCA SEQ. ID. NO: 34 | AGGAGGCATCCAGCGAATG SEQ. ID. NO: 35 |

The paramount importance of the second immunoglobulin-like domain for the function of trkC and trkB is apparent from the foregoing results. Deletion of all but this domain retained essentially the full binding capacity of trkC. Deletion of this domain removed the ability of trkC to bind NT-3. Exchanging this domain created a trkC variant that was able to bind BDNF with similar affinity as trkB.

EXAMPLE 5

Use of trkA-IgG Immunoadhesin in the Treatment of Inflammatory Pain

A. Blocking of carageean-induced hyperalgesia in rats

50 μl of a 2% aqueous solution of carageenan (Sigma, Lot # 21H0322) alone or in combination with 15 μg of the The entire disclosures of all citations cited throughout the specification, and the references cited therein, are hereby expressly incorporated by reference.

Although the foregoing refers to particular preferred embodiments, it will be understood that the present invention is not so limited. It will occur to those ordinarily skilled in the art that various modifications may be made to the disclosed embodiments without diverting from the overall concept of the invention. All such modifications are intended to be within the scope of the present invention.

SEQUENCE LISTING ( 1 ) GENERAL INFORMATION:

( i i i ) NUMBER OF SEQUENCES: 41

( 2 ) INFORMATION FOR SEQ ID NO:1:

( i ) SEQUENCE CHARACTERISTICS:
( A ) LENGTH: 3194 base pairs
( B ) TYPE: Nucleic Acid
( C ) STRANDEDNESS: Single
( D ) TOPOLOGY: Linear ( i i ) MOLECULE TYPE: nucleic acid ( x i ) SEQUENCE DESCRIPTION: SEQ ID NO:1:

| | | | | | |
|---|---|---|---|---|---|
| GGAAGGTTTA | AAGAAGAAGC | CGCAAAGCGC | AGGGAAGGCC | TCCCGGCACG | 50 |
| GGTGGGGGAA | AGCGGCCGGT | GCAGCGCGGG | GACAGGCACT | CGGGCTGGCA | 100 |
| CTGGCTGCTA | GGGATGTCGT | CCTGGATAAG | GTGGCATGGA | CCCGCCATGG | 150 |
| CGCGGCTCTG | GGGCTTCTGC | TGGCTGGTTG | TGGGCTTCTG | GAGGGCCGCT | 200 |
| TTCGCCTGTC | CCACGTCCTG | CAAATGCAGT | GCCTCTCGGA | TCTGGTGCAG | 250 |
| CGACCCTTCT | CCTGGCATCG | TGGCATTTCC | GAGATTGGAG | CCTAACAGTG | 300 |
| TAGATCCTGA | GAACATCACC | GAAATTTTCA | TCGCAAACCA | GAAAAGGTTA | 350 |
| GAAATCATCA | ACGAAGATGA | TGTTGAAGCT | TATGTGGGAC | TGAGAAATCT | 400 |
| GACAATTGTG | GATTCTGGAT | TAAAATTTGT | GGCTCATAAA | GCATTTCTGA | 450 |
| AAAACAGCAA | CCTGCAGCAC | ATCAATTTTA | CCCGAAACAA | ACTGACGAGT | 500 |
| TTGTCTAGGA | AACATTTCCG | TCACCTTGAC | TTGTCTGAAC | TGATCCTGGT | 550 |
| GGGCAATCCA | TTTACATGCT | CCTGTGACAT | TATGTGGATC | AAGACTCTCC | 600 |
| AAGAGGCTAA | ATCCAGTCCA | GACACTCAGG | ATTTGTACTG | CCTGAATGAA | 650 |
| AGCAGCAAGA | ATATTCCCCT | GGCAAACCTG | CAGATACCCA | ATTGTGGTTT | 700 |
| GCCATCTGCA | AATCTGGCCG | CACCTAACCT | CACTGTGGAG | GAAGGAAAGT | 750 |
| CTATCACATT | ATCCTGTAGT | GTGGCAGGTG | ATCCGGTTCC | TAATATGTAT | 800 |
| TGGGATGTTG | GTAACCTGGT | TTCCAAACAT | ATGAATGAAA | CAAGCCACAC | 850 |
| ACAGGGCTCC | TTAAGGATAA | CTAACATTTC | ATCCGATGAC | AGTGGGAAGC | 900 |
| AGATCTCTTG | TGTGGCGGAA | AATCTTGTAG | GAGAAGATCA | AGATTCTGTC | 950 |
| AACCTCACTG | TGCATTTTGC | ACCAACTATC | ACATTCTCG | AATCTCCAAC | 1000 |
| CTCAGACCAC | CACTGGTGCA | TTCCATTCAC | TGTGAAAGGC | AACCCAAAAC | 1050 |
| CAGCGCTTCA | GTGGTTCTAT | AACGGGGCAA | TATTGAATGA | GTCCAAATAC | 1100 |
| ATCTGTACTA | AAATACATGT | TACCAATCAC | ACGGAGTACC | ACGGCTGCCT | 1150 |
| CCAGCTGGAT | AATCCCACTC | ACATGAACAA | TGGGGACTAC | ACTCTAATAG | 1200 |
| CCAAGAATGA | GTATGGGAAG | GATGAGAAAC | AGATTTCTGC | TCACTTCATG | 1250 |
| GGCTGGCCTG | GAATTGACGA | TGGTGCAAAC | CCAAATTATC | CTGATGTAAT | 1300 |
| TTATGAAGAT | TATGGAACTG | CAGCGAATGA | CATCGGGGAC | ACCACGAACA | 1350 |
| GAAGTAATGA | AATCCCTTCC | ACAGACGTCA | CTGATAAAAC | CGGTCGGGAA | 1400 |
| CATCTCTCGG | TCTATGCTGT | GGTGGTGATT | GCGTCTGTGG | TGGGATTTTG | 1450 |
| CCTTTTGGTA | ATGCTGTTTC | TGCTTAAGTT | GGCAAGACAC | TCCAAGTTTG | 1500 |

| | | | | |
|---|---|---|---|---|
| GCATGAAAGG | CCCAGCCTCC | GTTATCAGCA | ATGATGATGA | CTCTGCCAGC | 1550
| CCACTCCATC | ACATCTCCAA | TGGGAGTAAC | ACTCCATCTT | CTTCGGAAGG | 1600
| TGGCCCAGAT | GCTGTCATTA | TTGGAATGAC | CAAGATCCCT | GTCATTGAAA | 1650
| ATCCCCAGTA | CTTTGGCATC | ACCAACAGTC | AGCTCAAGCC | AGACACATTT | 1700
| GTTCAGCACA | TCAAGCGACA | TAACATTGTT | CTGAAAAGGG | AGCTAGGCGA | 1750
| AGGAGCCTTT | GGAAAAGTGT | TCCTAGCTGA | ATGCTATAAC | CTCTGTCCTG | 1800
| AGCAGGACAA | GATCTTGGTG | GCAGTGAAGA | CCCTGAAGGA | TGCCAGTGAC | 1850
| AATGCACGCA | AGGACTTCCA | CCGTGAGGCC | GAGCTCCTGA | CCAACCTCCA | 1900
| GCATGAGCAC | ATCGTCAAGT | TCTATGGCGT | CTGCGTGGAG | GGCGACCCCC | 1950
| TCATCATGGT | CTTTGAGTAC | ATGAAGCATG | GGACCTCAA  | CAAGTTCCTC | 2000
| AGGGCACACG | GCCCTGATGC | CGTGCTGATG | GCTGAGGGCA | ACCCGCCCAC | 2050
| GGAACTGACG | CAGTCGCAGA | TGCTGCATAT | AGCCCAGCAG | ATCGCCGCGG | 2100
| GCATGGTCTA | CCTGGCGTCC | CAGCACTTCG | TGCACCGCGA | TTTGGCCACC | 2150
| AGGAACTGCC | TGGTCGGGGA | GAACTTGCTG | GTGAAAATCG | GGACTTTGG  | 2200
| GATGTCCCGG | GACGTGTACA | GCACTGACTA | CTACAGGGTC | GGTGGCCACA | 2250
| CAATGCTGCC | CATTCGCTGG | ATGCCTCCAG | AGAGCATCAT | GTACAGGAAA | 2300
| TTCACGACGG | AAAGCGACGT | CTGGAGCCTG | GGGGTCGTGT | TGTGGGAGAT | 2350
| TTTCACCTAT | GGCAAACAGC | CCTGGTACCA | GCTGTCAAAC | AATGAGGTGA | 2400
| TAGAGTGTAT | CACTCAGGGC | CGAGTCCTGC | AGCGACCCCG | CACGTGCCCC | 2450
| CAGGAGGTGT | ATGAGCTGAT | GCTGGGGTGC | TGGCAGCGAG | AGCCCCACAT | 2500
| GAGGAAGAAC | ATCAAGGGCA | TCCATACCCT | CCTTCAGAAC | TTGGCCAAGG | 2550
| CATCTCCGGT | CTACCTGGAC | ATTCTAGGCT | AGGGCCTTT  | TCCCCAGACC | 2600
| GATCCTTCCC | AACGTACTCC | TCAGACGGGC | TGAGAGGATG | AACATCTTTT | 2650
| AACTGCCGCT | GGAGGCCACC | AAGCTGCTCT | CCTTCACTCT | GACAGTATTA | 2700
| ACATCAAAGA | CTCCGAGAAG | CTCTCGAGGG | AAGCAGTGTG | TACTTCTTCA | 2750
| TCCATAGACA | CAGTATTGAC | TTCTTTTGG  | CATTATCTCT | TTCTCTCTTT | 2800
| CCATCTCCCT | TGGTTGTTCC | TTTTTCTTTT | TTTAAATTTT | CTTTTTCTTC | 2850
| TTTTTTTCG  | TCTTCCCTGC | TTCACGATTC | TTACCCTTTC | TTTTGAATCA | 2900
| ATCTGGCTTC | TGCATTACTA | TTAACTCTGC | ATAGACAAAG | GCCTTAACAA | 2950
| ACGTAATTTG | TTATATCAGC | AGACACTCCA | GTTTGCCCAC | CACAACTAAC | 3000
| AATGCCTTGT | TGTATTCCTG | CCTTTGATGT | GGATGAAAAA | AAGGGAAAAC | 3050
| AAATATTTCA | CTTAAACTTT | GTCACTTCTG | CTGTACAGAT | ATCGAGAGTT | 3100
| TCTATGGATT | CACTTCTATT | TATTTATTAT | TATTACTGTT | CTTATTGTTT | 3150
| TTGGATGGCT | TAAGCCTGTG | TATAAAAAAA | AAAAAAATC  | TAGA | 3194

( 2 ) INFORMATION FOR SEQ ID NO:2:

( i ) SEQUENCE CHARACTERISTICS:
        ( A ) LENGTH: 822 amino acids
        ( B ) TYPE: Amino Acid
        ( D ) TOPOLOGY: Linear ( x i ) SEQUENCE DESCRIPTION: SEQ ID NO:2:

Met  Ser  Ser  Trp  Ile  Arg  Trp  His  Gly  Pro  Ala  Met  Ala  Arg  Leu
 1             5                      10                     15

-continued

| | | | | | | | | | | | |
|---|---|---|---|---|---|---|---|---|---|---|---|
| Trp | Gly | Phe | Cys | Trp 20 | Leu | Val | Val | Gly | Phe 25 | Trp | Arg | Ala | Ala | Phe 30 |
| Ala | Cys | Pro | Thr | Ser 35 | Cys | Lys | Cys | Ser | Ala 40 | Ser | Arg | Ile | Trp | Cys 45 |
| Ser | Asp | Pro | Ser | Pro 50 | Gly | Ile | Val | Ala | Phe 55 | Pro | Arg | Leu | Glu | Pro 60 |
| Asn | Ser | Val | Asp | Pro 65 | Glu | Asn | Ile | Thr | Glu 70 | Ile | Phe | Ile | Ala | Asn 75 |
| Gln | Lys | Arg | Leu | Glu 80 | Ile | Ile | Asn | Glu | Asp 85 | Asp | Val | Glu | Ala | Tyr 90 |
| Val | Gly | Leu | Arg | Asn 95 | Leu | Thr | Ile | Val | Asp 100 | Ser | Gly | Leu | Lys | Phe 105 |
| Val | Ala | His | Lys | Ala 110 | Phe | Leu | Lys | Asn | Ser 115 | Asn | Leu | Gln | His | Ile 120 |
| Asn | Phe | Thr | Arg | Asn 125 | Lys | Leu | Thr | Ser | Leu 130 | Ser | Arg | Lys | His | Phe 135 |
| Arg | His | Leu | Asp | Leu 140 | Ser | Glu | Leu | Ile | Leu 145 | Val | Gly | Asn | Pro | Phe 150 |
| Thr | Cys | Ser | Cys | Asp 155 | Ile | Met | Trp | Ile | Lys 160 | Thr | Leu | Gln | Glu | Ala 165 |
| Lys | Ser | Ser | Pro | Asp 170 | Thr | Gln | Asp | Leu | Tyr 175 | Cys | Leu | Asn | Glu | Ser 180 |
| Ser | Lys | Asn | Ile | Pro 185 | Leu | Ala | Asn | Leu | Gln 190 | Ile | Pro | Asn | Cys | Gly 195 |
| Leu | Pro | Ser | Ala | Asn 200 | Leu | Ala | Ala | Pro | Asn 205 | Leu | Thr | Val | Glu | Glu 210 |
| Gly | Lys | Ser | Ile | Thr 215 | Leu | Ser | Cys | Ser | Val 220 | Ala | Gly | Asp | Pro | Val 225 |
| Pro | Asn | Met | Tyr | Trp 230 | Asp | Val | Gly | Asn | Leu 235 | Val | Ser | Lys | His | Met 240 |
| Asn | Glu | Thr | Ser | His 245 | Thr | Gln | Gly | Ser | Leu 250 | Arg | Ile | Thr | Asn | Ile 255 |
| Ser | Ser | Asp | Asp | Ser 260 | Gly | Lys | Gln | Ile | Ser 265 | Cys | Val | Ala | Glu | Asn 270 |
| Leu | Val | Gly | Glu | Asp 275 | Gln | Asp | Ser | Val | Asn 280 | Leu | Thr | Val | His | Phe 285 |
| Ala | Pro | Thr | Ile | Thr 290 | Phe | Leu | Glu | Ser | Pro 295 | Thr | Ser | Asp | His | His 300 |
| Trp | Cys | Ile | Pro | Phe 305 | Thr | Val | Lys | Gly | Asn 310 | Pro | Lys | Pro | Ala | Leu 315 |
| Gln | Trp | Phe | Tyr | Asn 320 | Gly | Ala | Ile | Leu | Asn 325 | Glu | Ser | Lys | Tyr | Ile 330 |
| Cys | Thr | Lys | Ile | His 335 | Val | Thr | Asn | His | Thr 340 | Glu | Tyr | His | Gly | Cys 345 |
| Leu | Gln | Leu | Asp | Asn 350 | Pro | Thr | His | Met | Asn 355 | Asn | Gly | Asp | Tyr | Thr 360 |
| Leu | Ile | Ala | Lys | Asn 365 | Glu | Tyr | Gly | Lys | Asp 370 | Glu | Lys | Gln | Ile | Ser 375 |
| Ala | His | Phe | Met | Gly 380 | Trp | Pro | Gly | Ile | Asp 385 | Asp | Gly | Ala | Asn | Pro 390 |
| Asn | Tyr | Pro | Asp | Val 395 | Ile | Tyr | Glu | Asp | Tyr 400 | Gly | Thr | Ala | Ala | Asn 405 |
| Asp | Ile | Gly | Asp | Thr | Thr | Asn | Arg | Ser | Asn | Glu | Ile | Pro | Ser | Thr |

-continued

|     |     |     |     |     | 410 |     |     |     |     | 415 |     |     |     |     | 420 |
| --- | --- | --- | --- | --- | --- | --- | --- | --- | --- | --- | --- | --- | --- | --- | --- |
| Asp | Val | Thr | Asp | Lys | Thr | Gly | Arg | Glu | His | Leu | Ser | Val | Tyr | Ala |
|     |     |     |     | 425 |     |     |     |     | 430 |     |     |     |     | 435 |
| Val | Val | Val | Ile | Ala | Ser | Val | Val | Gly | Phe | Cys | Leu | Leu | Val | Met |
|     |     |     |     | 440 |     |     |     |     | 445 |     |     |     |     | 450 |
| Leu | Phe | Leu | Leu | Lys | Leu | Ala | Arg | His | Ser | Lys | Phe | Gly | Met | Lys |
|     |     |     |     | 455 |     |     |     |     | 460 |     |     |     |     | 465 |
| Gly | Pro | Ala | Ser | Val | Ile | Ser | Asn | Asp | Asp | Ser | Ala | Ser | Pro |
|     |     |     |     | 470 |     |     |     |     | 475 |     |     |     |     | 480 |
| Leu | His | His | Ile | Ser | Asn | Gly | Ser | Asn | Thr | Pro | Ser | Ser | Ser | Glu |
|     |     |     |     | 485 |     |     |     |     | 490 |     |     |     |     | 495 |
| Gly | Gly | Pro | Asp | Ala | Val | Ile | Ile | Gly | Met | Thr | Lys | Ile | Pro | Val |
|     |     |     |     | 500 |     |     |     |     | 505 |     |     |     |     | 510 |
| Ile | Glu | Asn | Pro | Gln | Tyr | Phe | Gly | Ile | Thr | Asn | Ser | Gln | Leu | Lys |
|     |     |     |     | 515 |     |     |     |     | 520 |     |     |     |     | 525 |
| Pro | Asp | Thr | Phe | Val | Gln | His | Ile | Lys | Arg | His | Asn | Ile | Val | Leu |
|     |     |     |     | 530 |     |     |     |     | 535 |     |     |     |     | 540 |
| Lys | Arg | Glu | Leu | Gly | Glu | Gly | Ala | Phe | Gly | Lys | Val | Phe | Leu | Ala |
|     |     |     |     | 545 |     |     |     |     | 550 |     |     |     |     | 555 |
| Glu | Cys | Tyr | Asn | Leu | Cys | Pro | Glu | Gln | Asp | Lys | Ile | Leu | Val | Ala |
|     |     |     |     | 560 |     |     |     |     | 565 |     |     |     |     | 570 |
| Val | Lys | Thr | Leu | Lys | Asp | Ala | Ser | Asp | Asn | Ala | Arg | Lys | Asp | Phe |
|     |     |     |     | 575 |     |     |     |     | 580 |     |     |     |     | 585 |
| His | Arg | Glu | Ala | Glu | Leu | Leu | Thr | Asn | Leu | Gln | His | Glu | His | Ile |
|     |     |     |     | 590 |     |     |     |     | 595 |     |     |     |     | 600 |
| Val | Lys | Phe | Tyr | Gly | Val | Cys | Val | Glu | Gly | Asp | Pro | Leu | Ile | Met |
|     |     |     |     | 605 |     |     |     |     | 610 |     |     |     |     | 615 |
| Val | Phe | Glu | Tyr | Met | Lys | His | Gly | Asp | Leu | Asn | Lys | Phe | Leu | Arg |
|     |     |     |     | 620 |     |     |     |     | 625 |     |     |     |     | 630 |
| Ala | His | Gly | Pro | Asp | Ala | Val | Leu | Met | Ala | Glu | Gly | Asn | Pro | Pro |
|     |     |     |     | 635 |     |     |     |     | 640 |     |     |     |     | 645 |
| Thr | Glu | Leu | Thr | Gln | Ser | Gln | Met | Leu | His | Ile | Ala | Gln | Gln | Ile |
|     |     |     |     | 650 |     |     |     |     | 655 |     |     |     |     | 660 |
| Ala | Ala | Gly | Met | Val | Tyr | Leu | Ala | Ser | Gln | His | Phe | Val | His | Arg |
|     |     |     |     | 665 |     |     |     |     | 670 |     |     |     |     | 675 |
| Asp | Leu | Ala | Thr | Arg | Asn | Cys | Leu | Val | Gly | Glu | Asn | Leu | Leu | Val |
|     |     |     |     | 680 |     |     |     |     | 685 |     |     |     |     | 690 |
| Lys | Ile | Gly | Asp | Phe | Gly | Met | Ser | Arg | Asp | Val | Tyr | Ser | Thr | Asp |
|     |     |     |     | 695 |     |     |     |     | 700 |     |     |     |     | 705 |
| Tyr | Tyr | Arg | Val | Gly | Gly | His | Thr | Met | Leu | Pro | Ile | Arg | Trp | Met |
|     |     |     |     | 710 |     |     |     |     | 715 |     |     |     |     | 720 |
| Pro | Pro | Glu | Ser | Ile | Met | Tyr | Arg | Lys | Phe | Thr | Thr | Glu | Ser | Asp |
|     |     |     |     | 725 |     |     |     |     | 730 |     |     |     |     | 735 |
| Val | Trp | Ser | Leu | Gly | Val | Val | Leu | Trp | Glu | Ile | Phe | Thr | Tyr | Gly |
|     |     |     |     | 740 |     |     |     |     | 745 |     |     |     |     | 750 |
| Lys | Gln | Pro | Trp | Tyr | Gln | Leu | Ser | Asn | Asn | Glu | Val | Ile | Glu | Cys |
|     |     |     |     | 755 |     |     |     |     | 760 |     |     |     |     | 765 |
| Ile | Thr | Gln | Gly | Arg | Val | Leu | Gln | Arg | Pro | Arg | Thr | Cys | Pro | Gln |
|     |     |     |     | 770 |     |     |     |     | 775 |     |     |     |     | 780 |
| Glu | Val | Tyr | Glu | Leu | Met | Leu | Gly | Cys | Trp | Gln | Arg | Glu | Pro | His |
|     |     |     |     | 785 |     |     |     |     | 790 |     |     |     |     | 795 |
| Met | Arg | Lys | Asn | Ile | Lys | Gly | Ile | His | Thr | Leu | Leu | Gln | Asn | Leu |
|     |     |     |     | 800 |     |     |     |     | 805 |     |     |     |     | 810 |

| Ala | Lys | Ala | Ser | Pro | Val | Tyr | Leu | Asp | Ile | Leu | Gly |
|-----|-----|-----|-----|-----|-----|-----|-----|-----|-----|-----|-----|
|     |     |     |     | 815 |     |     |     | 820 |     |     | 822 |

( 2 ) INFORMATION FOR SEQ ID NO:3:

( i ) SEQUENCE CHARACTERISTICS:
        ( A ) LENGTH: 1870 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:3:

```
GGAAGGTTTA  AAGAAGAAGC  CGCAAAGCGC  AGGGAAGGCC  TCCCGGCACG         50

GGTGGGGGAA  AGCGGCCGGT  GCAGCGCGGG  GACAGGCACT  CGGGCTGGCA        100

CTGGCTGCTA  GGGATGTCGT  CCTGGATAAG  GTGGCATGGA  CCCGCCATGG        150

CGCGGCTCTG  GGGCTTCTGC  TGGCTGGTTG  TGGGCTTCTG  GAGGGCCGCT        200

TTCGCCTGTC  CCACGTCCTG  CAAATGCAGT  GCCTCTCGGA  TCTGGTGCAG        250

CGACCCTTCT  CCTGGCATCG  TGGCATTTCC  GAGATTGGAG  CCTAACAGTG        300

TAGATCCTGA  GAACATCACC  GAAATTTTCA  TCGCAAACCA  GAAAAGGTTA        350

GAAATCATCA  ACGAAGATGA  TGTTGAAGCT  TATGTGGGAC  TGAGAAATCT        400

GACAATTGTG  GATTCTGGAT  TAAAATTTGT  GGCTCATAAA  GCATTTCTGA        450

AAAACAGCAA  CCTGCAGCAC  ATCAATTTTA  CCCGAAACAA  ACTGACGAGT        500

TTGTCTAGGA  ACATTTCCG   TCACCTTGAC  TTGTCTGAAC  TGATCCTGGT        550

GGGCAATCCA  TTTACATGCT  CCTGTGACAT  TATGTGGATC  AAGACTCTCC        600

AAGAGGCTAA  ATCCAGTCCA  GACACTCAGG  ATTTGTACTG  CCTGAATGAA        650

AGCAGCAAGA  ATATTCCCCT  GGCAAACCTG  CAGATACCCA  ATTGTGGTTT        700

GCCATCTGCA  AATCTGGCCG  CACCTAACCT  CACTGTGGAG  GAAGGAAAGT        750

CTATCACATT  ATCCTGTAGT  GTGGCAGGTG  ATCCGGTTCC  TAATATGTAT        800

TGGGATGTTG  GTAACCTGGT  TTCCAAACAT  ATGAATGAAA  CAAGCCACAC        850

ACAGGGCTCC  TTAAGGATAA  CTAACATTTC  ATCCGATGAC  AGTGGGAAGC        900

AGATCTCTTG  TGTGGCGGAA  AATCTTGTAG  GAGAAGATCA  AGATTCTGTC        950

AACCTCACTG  TGCATTTGC   ACCAACTATC  ACATTTCTCG  AATCTCCAAC       1000

CTCAGACCAC  CACTGGTGCA  TTCCATTCAC  TGTGAAAGGC  AACCCAAAAC       1050

CAGCGCTTCA  GTGGTTCTAT  AACGGGGCAA  TATTGAATGA  GTCCAAATAC       1100

ATCTGTACTA  AAATACATGT  TACCAATCAC  ACGGAGTACC  ACGGCTGCCT       1150

CCAGCTGGAT  AATCCCACTC  ACATGAACAA  TGGGGACTAC  ACTCTAATAG       1200

CCAAGAATGA  GTATGGGAAG  GATGAGAAAC  AGATTTCTGC  TCACTTCATG       1250

GGCTGGCCTG  GAATTGACGA  TGGTGCAAAC  CCAAATTATC  CTGATGTAAT       1300

TTATGAAGAT  TATGGAACTG  CAGCGAATGA  CATCGGGGAC  ACCACGAACA       1350

GAAGTAATGA  AATCCCTTCC  ACAGACGTCA  CTGATAAAAC  CGGTCGGGAA       1400

CATCTCTCGG  TCTATGCTGT  GGTGGTGATT  GCGTCTGTGG  TGGGATTTTG       1450

CCTTTTGGTA  ATGCTGTTTC  TGCTTAAGTT  GGCAAGACAC  TCCAAGTTTG       1500

GCATGAAAGG  TTTTGTTTTG  TTTCATAAGA  TCCCACTGGA  TGGGTAGCTG       1550

AAATAAAGGA  AAAGACAGAG  AAAGGGGCTG  TGGTGCTTGT  TGGTTGATGC       1600

TGCCATGTAA  GCTGGACTCC  TGGGACTGCT  GTTGGCTTAT  CCCGGGAAGT       1650
```

```
GCTGCTTATC  TGGGGTTTTC  TGGTAGATGT  GGGCGGTGTT  TGGAGGCTGT        1700

ACTATATGAA  GCCTGCATAT  ACTGTGAGCT  GTGATTGGGG  AACACCAATG        1750

CAGAGGTAAC  TCTCAGGCAG  CTAAGCAGCA  CCTCAAGAAA  ACATGTTAAA        1800

TTAATGCTTC  TCTTCTTACA  GTAGTTCAAA  TACAAAACTG  AAATGAAATC        1850

CCATTGGATT  GTACTTCTCT                                            1870
```

( 2 ) INFORMATION FOR SEQ ID NO:4:

( i ) SEQUENCE CHARACTERISTICS:
( A ) LENGTH: 477 amino acids
( B ) TYPE: Amino Acid
( D ) TOPOLOGY: Linear ( x i ) SEQUENCE DESCRIPTION: SEQ ID NO:4:

```
Met  Ser  Ser  Trp  Ile  Arg  Trp  His  Gly  Pro  Ala  Met  Ala  Arg  Leu
 1                  5                    10                        15

Trp  Gly  Phe  Cys  Trp  Leu  Val  Val  Gly  Phe  Trp  Arg  Ala  Ala  Phe
                    20                   25                        30

Ala  Cys  Pro  Thr  Ser  Cys  Lys  Cys  Ser  Ala  Ser  Arg  Ile  Trp  Cys
                    35                   40                        45

Ser  Asp  Pro  Ser  Pro  Gly  Ile  Val  Ala  Phe  Pro  Arg  Leu  Glu  Pro
                    50                   55                        60

Asn  Ser  Val  Asp  Pro  Glu  Asn  Ile  Thr  Glu  Ile  Phe  Ile  Ala  Asn
                    65                   70                        75

Gln  Lys  Arg  Leu  Glu  Ile  Ile  Asn  Glu  Asp  Asp  Val  Glu  Ala  Tyr
                    80                   85                        90

Val  Gly  Leu  Arg  Asn  Leu  Thr  Ile  Val  Asp  Ser  Gly  Leu  Lys  Phe
                    95                   100                       105

Val  Ala  His  Lys  Ala  Phe  Leu  Lys  Asn  Ser  Asn  Leu  Gln  His  Ile
                    110                  115                       120

Asn  Phe  Thr  Arg  Asn  Lys  Leu  Thr  Ser  Leu  Ser  Arg  Lys  His  Phe
                    125                  130                       135

Arg  His  Leu  Asp  Leu  Ser  Glu  Leu  Ile  Leu  Val  Gly  Asn  Pro  Phe
                    140                  145                       150

Thr  Cys  Ser  Cys  Asp  Ile  Met  Trp  Ile  Lys  Thr  Leu  Gln  Glu  Ala
                    155                  160                       165

Lys  Ser  Ser  Pro  Asp  Thr  Gln  Asp  Leu  Tyr  Cys  Leu  Asn  Glu  Ser
                    170                  175                       180

Ser  Lys  Asn  Ile  Pro  Leu  Ala  Asn  Leu  Gln  Ile  Pro  Asn  Cys  Gly
                    185                  190                       195

Leu  Pro  Ser  Ala  Asn  Leu  Ala  Ala  Pro  Asn  Leu  Thr  Val  Glu  Glu
                    200                  205                       210

Gly  Lys  Ser  Ile  Thr  Leu  Ser  Cys  Ser  Val  Ala  Gly  Asp  Pro  Val
                    215                  220                       225

Pro  Asn  Met  Tyr  Trp  Asp  Val  Gly  Asn  Leu  Val  Ser  Lys  His  Met
                    230                  235                       240

Asn  Glu  Thr  Ser  His  Thr  Gln  Gly  Ser  Leu  Arg  Ile  Thr  Asn  Ile
                    245                  250                       255

Ser  Ser  Asp  Asp  Ser  Gly  Lys  Gln  Ile  Ser  Cys  Val  Ala  Glu  Asn
                    260                  265                       270

Leu  Val  Gly  Glu  Asp  Gln  Asp  Ser  Val  Asn  Leu  Thr  Val  His  Phe
                    275                  280                       285

Ala  Pro  Thr  Ile  Thr  Phe  Leu  Glu  Ser  Pro  Thr  Ser  Asp  His  His
                    290                  295                       300
```

| | | | | | | | | | | | | | | |
|---|---|---|---|---|---|---|---|---|---|---|---|---|---|---|
| Trp | Cys | Ile | Pro | Phe<br>305 | Thr | Val | Lys | Gly | Asn<br>310 | Pro | Lys | Pro | Ala | Leu<br>315 |
| Gln | Trp | Phe | Tyr | Asn<br>320 | Gly | Ala | Ile | Leu | Asn<br>325 | Glu | Ser | Lys | Tyr | Ile<br>330 |
| Cys | Thr | Lys | Ile | His<br>335 | Val | Thr | Asn | His | Thr<br>340 | Glu | Tyr | His | Gly | Cys<br>345 |
| Leu | Gln | Leu | Asp | Asn<br>350 | Pro | Thr | His | Met | Asn<br>355 | Asn | Gly | Asp | Tyr | Thr<br>360 |
| Leu | Ile | Ala | Lys | Asn<br>365 | Glu | Tyr | Gly | Lys | Asp<br>370 | Glu | Lys | Gln | Ile | Ser<br>375 |
| Ala | His | Phe | Met | Gly<br>380 | Trp | Pro | Gly | Ile | Asp<br>385 | Asp | Gly | Ala | Asn | Pro<br>390 |
| Asn | Tyr | Pro | Asp | Val<br>395 | Ile | Tyr | Glu | Asp | Tyr<br>400 | Gly | Thr | Ala | Ala | Asn<br>405 |
| Asp | Ile | Gly | Asp | Thr<br>410 | Thr | Asn | Arg | Ser | Asn<br>415 | Glu | Ile | Pro | Ser | Thr<br>420 |
| Asp | Val | Thr | Asp | Lys<br>425 | Thr | Gly | Arg | Glu | His<br>430 | Leu | Ser | Val | Tyr | Ala<br>435 |
| Val | Val | Val | Ile | Ala<br>440 | Ser | Val | Val | Gly | Phe<br>445 | Cys | Leu | Leu | Val | Met<br>450 |
| Leu | Phe | Leu | Leu | Lys<br>455 | Leu | Ala | Arg | His | Ser<br>460 | Lys | Phe | Gly | Met | Lys<br>465 |
| Gly | Phe | Val | Leu | Phe<br>470 | His | Lys | Ile | Pro | Leu<br>475 | Asp | Gly<br>477 | | | |

( 2 ) INFORMATION FOR SEQ ID NO:5:

( i ) SEQUENCE CHARACTERISTICS:
        ( A ) LENGTH: 2715 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:5:

| | | | | | |
|---|---|---|---|---|---|
| GGATCCGCGT | CGGAGATGGA | TGTCTCTCTT | TGCCCAGCCA | AGTGTAGTTT | 50 |
| CTGGCGGATT | TTCTTGCTGG | GAAGCGTCTG | GCTGGACTAT | GTGGGCTCCG | 100 |
| TGCTGGCTTG | CCCTGCAAAT | TGTGTCTGCA | GCAAGACTGA | GATCAATTGC | 150 |
| CGGCGGCCGG | ACGATGGGAA | CCTCTTCCCC | CTCCTGGAAG | GGCAGGATTC | 200 |
| AGGGAACAGC | AATGGGAACG | CCAATATCAA | CATCACGGAC | ATCTCAAGGA | 250 |
| ATATCACTTC | CATACACATA | GAGAACTGGC | GCAGTCTTCA | CACGCTCAAC | 300 |
| GCCGTGGACA | TGGAGCTCTA | CACCGGACTT | CAAAAGCTGA | CCATCAAGAA | 350 |
| CTCAGGACTT | CGGAGCATTC | AGCCCAGAGC | CTTTGCCAAG | AACCCCCATT | 400 |
| TGCGTTATAT | AAACCTGTCA | AGTAACCGGC | TCACCACACT | CTCGTGGCAG | 450 |
| CTCTTCCAGA | CGCTGAGTCT | TCGGGAATTG | CAGTTGGAGC | AGAACTTTTT | 500 |
| CAACTGCAGC | TGTGACATCC | GCTGGATGCA | GCTCTGGCAG | GAGCAGGGGG | 550 |
| AGGCCAAGCT | CAACAGCCAG | AACCTCTACT | GCATCAATGC | TGATGGCTCC | 600 |
| CAGCTTCCTC | TCTTCCGCAT | GAACATCAGT | CAGTGTGACC | TTCCTGAGAT | 650 |
| CAGCGTGAGC | CACGTCAACC | TGACCGTACG | AGAGGGTGAC | AATGCTGTTA | 700 |
| TCACTTGCAA | TGGCTCTGGA | TCACCCCTTC | CTGATGTGGA | CTGGATAGTC | 750 |
| ACTGGGCTGC | AGTCCATCAA | CACTCACCAG | ACCAATCTGA | ACTGGACCAA | 800 |
| TGTTCATGCC | ATCAACTTGA | CGCTGGTGAA | TGTGACGAGT | GAGGACAATG | 850 |

```
GCTTCACCCT  GACGTGCATT  GCAGAGAACG  TGGTGGGCAT  GAGCAATGCC           900
AGTGTTGCCC  TCACTGTCTA  CTATCCCCCA  CGTGTGGTGA  GCCTGGAGGA           950
GCCTGAGCTG  CGCCTGGAGC  ACTGCATCGA  GTTTGTGGTG  CGTGGCAACC          1000
CCCCACCAAC  GCTGCACTGG  CTGCACAATG  GCAGCCTCT   GCGGGAGTCC          1050
AAGATCATCC  ATGTGGAATA  CTACCAAGAG  GGAGAGATTT  CCGAGGGCTG          1100
CCTGCTCTTC  AACAAGCCCA  CCCACTACAA  CAATGGCAAC  TATACCCTCA          1150
TTGCCAAAAA  CCCACTGGGC  ACAGCCAACC  AGACCATCAA  TGGCCACTTC          1200
CTCAAGGAGC  CCTTTCCAGA  GAGCACGGAT  AACTTTATCT  TGTTTGACGA          1250
AGTGAGTCCC  ACACCTCCTA  TCACTGTGAC  CCACAAACCA  GAAGAAGACA          1300
CTTTTGGGGT  ATCCATAGCA  GTTGGACTTG  CTGCTTTTGC  CTGTGTCCTG          1350
TTGGTGGTTC  TCTTCGTCAT  GATCAACAAA  TATGGTCGAC  GGTCCAAATT          1400
TGGAATGAAG  GGTCCCGTGG  CTGTCATCAG  TGGTGAGGAG  GACTCAGCCA          1450
GCCCACTGCA  CCACATCAAC  CACGGCATCA  CCACGCCCTC  GTCACTGGAT          1500
GCCGGGCCCG  ACACTGTGGT  CATTGGCATG  ACTCGCATCC  CTGTCATTGA          1550
GAACCCCCAG  TACTTCCGTC  AGGGACACAA  CTGCCACAAG  CCGGACACGT          1600
ATGTGCAGCA  CATTAAGAGG  AGAGACATCG  TGCTGAAGCG  AGAACTGGGT          1650
GAGGGAGCCT  TTGGAAAGGT  CTTCCTGGCC  GAGTGCTACA  ACCTCAGCCC          1700
GACCAAGGAC  AAGATGCTTG  TGGCTGTGAA  GGCCCTGAAG  GATCCCACCC          1750
TGGCTGCCCG  GAAGGATTTC  CAGAGGGAGG  CCGAGCTGCT  CACCAACCTG          1800
CAGCATGAGC  ACATTGTCAA  GTTCTATGGA  GTGTGCGGCG  ATGGGGACCC          1850
CCTCATCATG  GTCTTTGAAT  ACATGAAGCA  TGGAGACCTG  AATAAGTTCC          1900
TCAGGGCCCA  TGGGCCAGAT  GCAATGATCC  TTGTGGATGG  ACAGCCACGC          1950
CAGGCCAAGG  GTGAGCTGGG  GCTCTCCCAA  ATGCTCCACA  TTGCCAGTCA          2000
GATCGCCTCG  GGTATGGTGT  ACCTGGCCTC  CCAGCACTTT  GTGCACCGAG          2050
ACCTGGCCAC  CAGGAACTGC  CTGGTTGGAG  CGAATCTGCT  AGTGAAGATT          2100
GGGGACTTCG  GCATGTCCAG  AGATGTCTAC  AGCACGGATT  ATTACAGGCT          2150
CTTTAATCCA  TCTGGAAATG  ATTTTTGTAT  ATGGTGTGAG  GTGGGAGGAC          2200
ACACCATGCT  CCCCATTCGC  TGGATGCCTC  CTGAAAGCAT  CATGTACCGG          2250
AAGTTCACTA  CAGAGAGTGA  TGTATGGAGC  TTCGGGGTGA  TCCTCTGGGA          2300
GATCTTCACC  TATGGAAAGC  AGCCATGGTT  CCAACTCTCA  AACACGGAGG          2350
TCATTGAGTG  CATTACCCAA  GGTCGTGTTT  TGGAGCGGCC  CCGAGTCTGC          2400
CCCAAAGAGG  TGTACGATGT  CATGCTGGGG  TGCTGGCAGA  GGGAACCACA          2450
GCAGCGGTTG  AACATCAAGG  AGATCTACAA  AATCCTCCAT  GCTTTGGGGA          2500
AGGCCACCCC  AATCTACCTG  GACATTCTTG  CTAGTGGTG   GCTGGTGGTC          2550
ATGAATTCAT  ACTCTGTTGC  CTCCTCTCTC  CCTGCCTCAC  ATCTCCCTTC          2600
CACCTCACAA  CTCCTTCCAT  CCTTGACTGA  AGCGAACATC  TTCATATAAA          2650
CTCAAGTGCC  TGCTACACAT  ACAACACTGA  AAAAAGGAAA  AAAAAGAAA           2700
AAAAAAAAA   ACCGC                                                   2715
```

( 2 ) INFORMATION FOR SEQ ID NO:6:

( i ) SEQUENCE CHARACTERISTICS:
    ( A ) LENGTH: 839 amino acids
    ( B ) TYPE: Amino Acid
    ( D ) TOPOLOGY: Linear ( x i ) SEQUENCE DESCRIPTION: SEQ ID NO:6:

```
Met Asp Val Ser Leu Cys Pro Ala Lys Cys Ser Phe Trp Arg Ile
 1               5                  10                 15

Phe Leu Leu Gly Ser Val Trp Leu Asp Tyr Val Gly Ser Val Leu
                20                  25                 30

Ala Cys Pro Ala Asn Cys Val Cys Ser Lys Thr Glu Ile Asn Cys
                35                  40                 45

Arg Arg Pro Asp Asp Gly Asn Leu Phe Pro Leu Leu Glu Gly Gln
                50                  55                 60

Asp Ser Gly Asn Ser Asn Gly Asn Ala Asn Ile Asn Ile Thr Asp
                65                  70                 75

Ile Ser Arg Asn Ile Thr Ser Ile His Ile Glu Asn Trp Arg Ser
                80                  85                 90

Leu His Thr Leu Asn Ala Val Asp Met Glu Leu Tyr Thr Gly Leu
                95                 100                105

Gln Lys Leu Thr Ile Lys Asn Ser Gly Leu Arg Ser Ile Gln Pro
               110                 115                120

Arg Ala Phe Ala Lys Asn Pro His Leu Arg Tyr Ile Asn Leu Ser
               125                 130                135

Ser Asn Arg Leu Thr Thr Leu Ser Trp Gln Leu Phe Gln Thr Leu
               140                 145                150

Ser Leu Arg Glu Leu Gln Leu Glu Gln Asn Phe Phe Asn Cys Ser
               155                 160                165

Cys Asp Ile Arg Trp Met Gln Leu Trp Gln Glu Gln Gly Glu Ala
               170                 175                180

Lys Leu Asn Ser Gln Asn Leu Tyr Cys Ile Asn Ala Asp Gly Ser
               185                 190                195

Gln Leu Pro Leu Phe Arg Met Asn Ile Ser Gln Cys Asp Leu Pro
               200                 205                210

Glu Ile Ser Val Ser His Val Asn Leu Thr Val Arg Glu Gly Asp
               215                 220                225

Asn Ala Val Ile Thr Cys Asn Gly Ser Gly Ser Pro Leu Pro Asp
               230                 235                240

Val Asp Trp Ile Val Thr Gly Leu Gln Ser Ile Asn Thr His Gln
               245                 250                255

Thr Asn Leu Asn Trp Thr Asn Val His Ala Ile Asn Leu Thr Leu
               260                 265                270

Val Asn Val Thr Ser Glu Asp Asn Gly Phe Thr Leu Thr Cys Ile
               275                 280                285

Ala Glu Asn Val Val Gly Met Ser Asn Ala Ser Val Ala Leu Thr
               290                 295                300

Val Tyr Tyr Pro Pro Arg Val Val Ser Leu Glu Glu Pro Glu Leu
               305                 310                315

Arg Leu Glu His Cys Ile Glu Phe Val Val Arg Gly Asn Pro Pro
               320                 325                330

Pro Thr Leu His Trp Leu His Asn Gly Gln Pro Leu Arg Glu Ser
               335                 340                345

Lys Ile Ile His Val Glu Tyr Tyr Gln Glu Gly Glu Ile Ser Glu
               350                 355                360

Gly Cys Leu Leu Phe Asn Lys Pro Thr His Tyr Asn Asn Gly Asn
```

|   |   |   | 365 |   |   |   |   | 370 |   |   |   | 375 |
|---|---|---|---|---|---|---|---|---|---|---|---|---|

Tyr Thr Leu Ile Ala Lys Asn Pro Leu Gly Thr Ala Asn Gln Thr
                380                 385                 390

Ile Asn Gly His Phe Leu Lys Glu Pro Phe Pro Glu Ser Thr Asp
                395                 400                 405

Asn Phe Ile Leu Phe Asp Glu Val Ser Pro Thr Pro Pro Ile Thr
                410                 415                 420

Val Thr His Lys Pro Glu Glu Asp Thr Phe Gly Val Ser Ile Ala
                425                 430                 435

Val Gly Leu Ala Ala Phe Ala Cys Val Leu Leu Val Val Leu Phe
                440                 445                 450

Val Met Ile Asn Lys Tyr Gly Arg Arg Ser Lys Phe Gly Met Lys
                455                 460                 465

Gly Pro Val Ala Val Ile Ser Gly Glu Glu Asp Ser Ala Ser Pro
                470                 475                 480

Leu His His Ile Asn His Gly Ile Thr Thr Pro Ser Ser Leu Asp
                485                 490                 495

Ala Gly Pro Asp Thr Val Val Ile Gly Met Thr Arg Ile Pro Val
                500                 505                 510

Ile Glu Asn Pro Gln Tyr Phe Arg Gln Gly His Asn Cys His Lys
                515                 520                 525

Pro Asp Thr Tyr Val Gln His Ile Lys Arg Arg Asp Ile Val Leu
                530                 535                 540

Lys Arg Glu Leu Gly Glu Gly Ala Phe Gly Lys Val Phe Leu Ala
                545                 550                 555

Glu Cys Tyr Asn Leu Ser Pro Thr Lys Asp Lys Met Leu Val Ala
                560                 565                 570

Val Lys Ala Leu Lys Asp Pro Thr Leu Ala Ala Arg Lys Asp Phe
                575                 580                 585

Gln Arg Glu Ala Glu Leu Leu Thr Asn Leu Gln His Glu His Ile
                590                 595                 600

Val Lys Phe Tyr Gly Val Cys Gly Asp Gly Asp Pro Leu Ile Met
                605                 610                 615

Val Phe Glu Tyr Met Lys His Gly Asp Leu Asn Lys Phe Leu Arg
                620                 625                 630

Ala His Gly Pro Asp Ala Met Ile Leu Val Asp Gly Gln Pro Arg
                635                 640                 645

Gln Ala Lys Gly Glu Leu Gly Leu Ser Gln Met Leu His Ile Ala
                650                 655                 660

Ser Gln Ile Ala Ser Gly Met Val Tyr Leu Ala Ser Gln His Phe
                665                 670                 675

Val His Arg Asp Leu Ala Thr Arg Asn Cys Leu Val Gly Ala Asn
                680                 685                 690

Leu Leu Val Lys Ile Gly Asp Phe Gly Met Ser Arg Asp Val Tyr
                695                 700                 705

Ser Thr Asp Tyr Tyr Arg Leu Phe Asn Pro Ser Gly Asn Asp Phe
                710                 715                 720

Cys Ile Trp Cys Glu Val Gly Gly His Thr Met Leu Pro Ile Arg
                725                 730                 735

Trp Met Pro Pro Glu Ser Ile Met Tyr Arg Lys Phe Thr Thr Glu
                740                 745                 750

Ser Asp Val Trp Ser Phe Gly Val Ile Leu Trp Glu Ile Phe Thr
                755                 760                 765

```
Tyr Gly Lys Gln Pro Trp Phe Gln Leu Ser Asn Thr Glu Val Ile
                770             775                 780

Glu Cys Ile Thr Gln Gly Arg Val Leu Glu Arg Pro Arg Val Cys
                785             790                 795

Pro Lys Glu Val Tyr Asp Val Met Leu Gly Cys Trp Gln Arg Glu
                800             805                 810

Pro Gln Gln Arg Leu Asn Ile Lys Glu Ile Tyr Lys Ile Leu His
                815             820                 825

Ala Leu Gly Lys Ala Thr Pro Ile Tyr Leu Asp Ile Leu Gly
                830             835             839
```

( 2 ) INFORMATION FOR SEQ ID NO:7:

( i ) SEQUENCE CHARACTERISTICS:
        ( A ) LENGTH: 1858 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:7:

```
GGATCCGCGT CGGAGATGGA TGTCTCTCTT TGCCCAGCCA AGTGTAGTTT           50
CTGGCGGATT TTCTTGCTGG GAAGCGTCTG GCTGGACTAT GTGGGCTCCG          100
TGCTGGCTTG CCCTGCAAAT TGTGTCTGCA GCAAGACTGA GATCAATTGC          150
CGGCGGCCGG ACGATGGGAA CCTCTTCCCC CTCCTGGAAG GGCAGGATTC          200
AGGGAACAGC AATGGGAACG CCAATATCAA CATCACGGAC ATCTCAAGGA          250
ATATCACTTC CATACACATA GAGAACTGGC GCAGTCTTCA CACGCTCAAC          300
GCCGTGGACA TGGAGCTCTA CACCGGACTT CAAAAGCTGA CCATCAAGAA          350
CTCAGGACTT CGGAGCATTC AGCCCAGAGC CTTTGCCAAG AACCCCCATT          400
TGCGTTATAT AAACCTGTCA AGTAACCGGC TCACCACACT CTCGTGGCAG          450
CTCTTCCAGA CGCTGAGTCT TCGGGAATTG CAGTTGGAGC AGAACTTTTT          500
CAACTGCAGC TGTGACATCC GCTGGATGCA GCTCTGGCAG GAGCAGGGGG          550
AGGCCAAGCT CAACAGCCAG AACCTCTACT GCATCAATGC TGATGGCTCC          600
CAGCTTCCTC TCTTCCGCAT GAACATCAGT CAGTGTGACC TTCCTGAGAT          650
CAGCGTGAGC CACGTCAACC TGACCGTACG AGAGGGTGAC AATGCTGTTA          700
TCACTTGCAA TGGCTCTGGA TCACCCCTTC CTGATGTGGA CTGGATAGTC          750
ACTGGGCTGC AGTCCATCAA CACTCACCAG ACCAATCTGA ACTGGACCAA          800
TGTTCATGCC ATCAACTTGA CGCTGGTGAA TGTGACGAGT GAGGACAATG          850
GCTTCACCCT GACGTGCATT GCAGAGAACG TGGTGGGCAT GAGCAATGCC          900
AGTGTTGCCC TCACTGTCTA CTATCCCCCA CGTGTGGTGA GCCTGGAGGA          950
GCCTGAGCTG CGCCTGGAGC ACTGCATCGA GTTTGTGGTG CGTGGCAACC         1000
CCCCACCAAC GCTGCACTGG CTGCACAATG GCAGCCTCT GCGGGAGTCC         1050
AAGATCATCC ATGTGGAATA CTACCAAGAG GGAGAGATTT CCGAGGGCTG         1100
CCTGCTCTTC AACAAGCCCA CCCACTACAA CAATGGCAAC TATACCCTCA         1150
TTGCCAAAAA CCCACTGGGC ACAGCCAACC AGACCATCAA TGGCCACTTC         1200
CTCAAGGAGC CCTTTCCAGA GAGCACGGAT AACTTTATCT TGTTTGACGA         1250
AGTGAGTCCC ACACCTCCTA TCACTGTGAC CCACAAACCA GAAGAAGACA         1300
CTTTTGGGGT ATCCATAGCA GTTGGACTTG CTGCTTTTGC CTGTGTCCTG         1350
```

```
TTGGTGGTTC  TCTTCGTCAT  GATCAACAAA  TATGGTCGAC  GGTCCAAATT                    1400

TGGAATGAAG  GGTCCCGTGG  CTGTCATCAG  TGGTGAGGAG  GACTCAGCCA                    1450

GCCCACTGCA  CCACATCAAC  CACGGCATCA  CCACGCCCTC  GTCACTGGAT                    1500

GCCGGGCCCG  ACACTGTGGT  CATTGGCATG  ACTCGCATCC  CTGTCATTGA                    1550

GAACCCCCAG  TACTTCCGTC  AGGGACACAA  CTGCCACAAG  CCGGACACGT                    1600

GGGTCTTTTC  AAACATAGAC  AATCATGGGA  TATTAAACTT  GAAGGACAAT                    1650

AGAGATCATC  TAGTCCCATC  AACTCACTAT  ATATATGAGG  AACCTGAGGT                    1700

CCAGAGTGGG  GAAGTGTCTT  ACCCAAGGTC  ACATGGTTTC  AGAGAAATTA                    1750

TGTTGAATCC  AATAAGCCTT  CCCGGACATT  CCAAGCCTCT  TAACCATGGC                    1800

ATCTATGTTG  AGGATGTCAA  TGTTTATTTC  AGCAAAGGAC  GTCATGGCCT                    1850

TTAAAAAC                                                                      1858
```

( 2 ) INFORMATION FOR SEQ ID NO:8:

( i ) SEQUENCE CHARACTERISTICS:
        ( A ) LENGTH: 612 amino acids
        ( B ) TYPE: Amino Acid
        ( D ) TOPOLOGY: Linear ( x i ) SEQUENCE DESCRIPTION: SEQ ID NO:8:

```
Met  Asp  Val  Ser  Leu  Cys  Pro  Ala  Lys  Cys  Ser  Phe  Trp  Arg  Ile
 1              5                        10                        15

Phe  Leu  Leu  Gly  Ser  Val  Trp  Leu  Asp  Tyr  Val  Gly  Ser  Val  Leu
               20                        25                        30

Ala  Cys  Pro  Ala  Asn  Cys  Val  Cys  Ser  Lys  Thr  Glu  Ile  Asn  Cys
               35                        40                        45

Arg  Arg  Pro  Asp  Asp  Gly  Asn  Leu  Phe  Pro  Leu  Leu  Glu  Gly  Gln
               50                        55                        60

Asp  Ser  Gly  Asn  Ser  Asn  Gly  Asn  Ala  Asn  Ile  Asn  Ile  Thr  Asp
                    65                        70                        75

Ile  Ser  Arg  Asn  Ile  Thr  Ser  Ile  His  Ile  Glu  Asn  Trp  Arg  Ser
                    80                        85                        90

Leu  His  Thr  Leu  Asn  Ala  Val  Asp  Met  Glu  Leu  Tyr  Thr  Gly  Leu
                    95                       100                       105

Gln  Lys  Leu  Thr  Ile  Lys  Asn  Ser  Gly  Leu  Arg  Ser  Ile  Gln  Pro
                   110                       115                       120

Arg  Ala  Phe  Ala  Lys  Asn  Pro  His  Leu  Arg  Tyr  Ile  Asn  Leu  Ser
                   125                       130                       135

Ser  Asn  Arg  Leu  Thr  Thr  Leu  Ser  Trp  Gln  Leu  Phe  Gln  Thr  Leu
                   140                       145                       150

Ser  Leu  Arg  Glu  Leu  Gln  Leu  Glu  Gln  Asn  Phe  Phe  Asn  Cys  Ser
                   155                       160                       165

Cys  Asp  Ile  Arg  Trp  Met  Gln  Leu  Trp  Gln  Glu  Gln  Gly  Glu  Ala
                   170                       175                       180

Lys  Leu  Asn  Ser  Gln  Asn  Leu  Tyr  Cys  Ile  Asn  Ala  Asp  Gly  Ser
                   185                       190                       195

Gln  Leu  Pro  Leu  Phe  Arg  Met  Asn  Ile  Ser  Gln  Cys  Asp  Leu  Pro
                   200                       205                       210

Glu  Ile  Ser  Val  Ser  His  Val  Asn  Leu  Thr  Val  Arg  Glu  Gly  Asp
                   215                       220                       225

Asn  Ala  Val  Ile  Thr  Cys  Asn  Gly  Ser  Gly  Ser  Pro  Leu  Pro  Asp
                   230                       235                       240
```

-continued

| | | | | | | | | | | | | | | | |
|---|---|---|---|---|---|---|---|---|---|---|---|---|---|---|---|
| Val | Asp | Trp | Ile | Val 245 | Thr | Gly | Leu | Gln | Ser 250 | Ile | Asn | Thr | His | Gln 255 |
| Thr | Asn | Leu | Asn | Trp 260 | Thr | Asn | Val | His | Ala 265 | Ile | Asn | Leu | Thr | Leu 270 |
| Val | Asn | Val | Thr | Ser 275 | Glu | Asp | Asn | Gly | Phe 280 | Thr | Leu | Thr | Cys | Ile 285 |
| Ala | Glu | Asn | Val | Val 290 | Gly | Met | Ser | Asn | Ala 295 | Ser | Val | Ala | Leu | Thr 300 |
| Val | Tyr | Tyr | Pro | Pro 305 | Arg | Val | Val | Ser | Leu 310 | Glu | Glu | Pro | Glu | Leu 315 |
| Arg | Leu | Glu | His | Cys 320 | Ile | Glu | Phe | Val | Val 325 | Arg | Gly | Asn | Pro | Pro 330 |
| Pro | Thr | Leu | His | Trp 335 | Leu | His | Asn | Gly | Gln 340 | Pro | Leu | Arg | Glu | Ser 345 |
| Lys | Ile | Ile | His | Val 350 | Glu | Tyr | Tyr | Gln | Glu 355 | Gly | Glu | Ile | Ser | Glu 360 |
| Gly | Cys | Leu | Leu | Phe 365 | Asn | Lys | Pro | Thr | His 370 | Tyr | Asn | Asn | Gly | Asn 375 |
| Tyr | Thr | Leu | Ile | Ala 380 | Lys | Asn | Pro | Leu | Gly 385 | Thr | Ala | Asn | Gln | Thr 390 |
| Ile | Asn | Gly | His | Phe 395 | Leu | Lys | Glu | Pro | Phe 400 | Pro | Glu | Ser | Thr | Asp 405 |
| Asn | Phe | Ile | Leu | Phe 410 | Asp | Glu | Val | Ser | Pro 415 | Thr | Pro | Pro | Ile | Thr 420 |
| Val | Thr | His | Lys | Pro 425 | Glu | Glu | Asp | Thr | Phe 430 | Gly | Val | Ser | Ile | Ala 435 |
| Val | Gly | Leu | Ala | Ala 440 | Phe | Ala | Cys | Val | Leu 445 | Leu | Val | Val | Leu | Phe 450 |
| Val | Met | Ile | Asn | Lys 455 | Tyr | Gly | Arg | Arg | Ser 460 | Lys | Phe | Gly | Met | Lys 465 |
| Gly | Pro | Val | Ala | Val 470 | Ile | Ser | Gly | Glu | Glu 475 | Asp | Ser | Ala | Ser | Pro 480 |
| Leu | His | His | Ile | Asn 485 | His | Gly | Ile | Thr | Thr 490 | Pro | Ser | Ser | Leu | Asp 495 |
| Ala | Gly | Pro | Asp | Thr 500 | Val | Val | Ile | Gly | Met 505 | Thr | Arg | Ile | Pro | Val 510 |
| Ile | Glu | Asn | Pro | Gln 515 | Tyr | Phe | Arg | Gln | Gly 520 | His | Asn | Cys | His | Lys 525 |
| Pro | Asp | Thr | Trp | Val 530 | Phe | Ser | Asn | Ile | Asp 535 | Asn | His | Gly | Ile | Leu 540 |
| Asn | Leu | Lys | Asp | Asn 545 | Arg | Asp | His | Leu | Val 550 | Pro | Ser | Thr | His | Tyr 555 |
| Ile | Tyr | Glu | Glu | Pro 560 | Glu | Val | Gln | Ser | Gly 565 | Glu | Val | Ser | Tyr | Pro 570 |
| Arg | Ser | His | Gly | Phe 575 | Arg | Glu | Ile | Met | Leu 580 | Asn | Pro | Ile | Ser | Leu 585 |
| Pro | Gly | His | Ser | Lys 590 | Pro | Leu | Asn | His | Gly 595 | Ile | Tyr | Val | Glu | Asp 600 |
| Val | Asn | Val | Tyr | Phe 605 | Ser | Lys | Gly | Arg | His 610 | Gly | Phe 612 | | | |

( 2 ) INFORMATION FOR SEQ ID NO:9:

( i ) SEQUENCE CHARACTERISTICS:
        ( A ) LENGTH: 790 amino acids ( B ) TYPE: Amino Acid
( D ) TOPOLOGY: Linear ( x i ) SEQUENCE DESCRIPTION: SEQ ID NO:9:

```
Met  Leu  Arg  Gly  Gly  Arg  Arg  Gly  Gln  Leu  Gly  Trp  His  Ser  Trp
 1              5                        10                       15

Ala  Ala  Gly  Pro  Gly  Ser  Leu  Leu  Ala  Trp  Leu  Ile  Leu  Ala  Ser
                    20                       25                       30

Ala  Gly  Ala  Ala  Pro  Cys  Pro  Asp  Ala  Cys  Cys  Pro  His  Gly  Ser
                    35                       40                       45

Ser  Gly  Leu  Arg  Cys  Thr  Arg  Asp  Gly  Ala  Leu  Asp  Ser  Leu  His
                    50                       55                       60

His  Leu  Pro  Gly  Ala  Glu  Asn  Leu  Thr  Glu  Leu  Tyr  Ile  Glu  Asn
                    65                       70                       75

Gln  Gln  His  Leu  Gln  His  Leu  Glu  Leu  Arg  Asp  Leu  Arg  Gly  Leu
                    80                       85                       90

Gly  Glu  Leu  Arg  Asn  Leu  Thr  Ile  Val  Lys  Ser  Gly  Leu  Arg  Phe
                    95                      100                      105

Val  Ala  Pro  Asp  Ala  Phe  His  Phe  Thr  Pro  Arg  Leu  Ser  Arg  Leu
                   110                      115                      120

Asn  Leu  Ser  Phe  Asn  Ala  Leu  Glu  Ser  Leu  Ser  Trp  Lys  Thr  Val
                   125                      130                      135

Gln  Gly  Leu  Ser  Leu  Gln  Glu  Leu  Val  Leu  Ser  Gly  Asn  Pro  Leu
                   140                      145                      150

His  Cys  Ser  Cys  Ala  Leu  Arg  Trp  Leu  Gln  Arg  Trp  Glu  Glu  Glu
                   155                      160                      165

Gly  Leu  Gly  Gly  Val  Pro  Glu  Gln  Lys  Leu  Gln  Cys  His  Gly  Gln
                   170                      175                      180

Gly  Pro  Leu  Ala  His  Met  Pro  Asn  Ala  Ser  Cys  Gly  Val  Pro  Thr
                   185                      190                      195

Leu  Lys  Val  Gln  Val  Pro  Asn  Ala  Ser  Val  Asp  Val  Gly  Asp  Asp
                   200                      205                      210

Val  Leu  Leu  Arg  Cys  Gln  Val  Glu  Gly  Arg  Gly  Leu  Glu  Gln  Ala
                   215                      220                      225

Gly  Trp  Ile  Leu  Thr  Glu  Leu  Glu  Gln  Ser  Ala  Thr  Val  Met  Lys
                   230                      235                      240

Ser  Gly  Gly  Leu  Pro  Ser  Leu  Gly  Leu  Thr  Leu  Ala  Asn  Val  Thr
                   245                      250                      255

Ser  Asp  Leu  Asn  Arg  Lys  Asn  Leu  Thr  Cys  Trp  Ala  Glu  Asn  Asp
                   260                      265                      270

Val  Gly  Arg  Ala  Glu  Val  Ser  Val  Gln  Val  Asn  Val  Ser  Phe  Pro
                   275                      280                      285

Ala  Ser  Val  Gln  Leu  His  Thr  Ala  Val  Glu  Met  His  His  Trp  Cys
                   290                      295                      300

Ile  Pro  Phe  Ser  Val  Asp  Gly  Gln  Pro  Ala  Pro  Ser  Leu  Arg  Trp
                   305                      310                      315

Leu  Phe  Asn  Gly  Ser  Val  Leu  Asn  Glu  Thr  Ser  Phe  Ile  Phe  Thr
                   320                      325                      330

Glu  Phe  Leu  Glu  Pro  Ala  Ala  Asn  Glu  Thr  Val  Arg  His  Gly  Cys
                   335                      340                      345

Leu  Arg  Leu  Asn  Gln  Pro  Thr  His  Val  Asn  Asn  Gly  Asn  Tyr  Thr
                   350                      355                      360

Leu  Leu  Ala  Ala  Asn  Pro  Phe  Gly  Gln  Ala  Ser  Ala  Ser  Ile  Met
                   365                      370                      375
```

```
Ala  Ala  Phe  Met  Asp  Asn  Pro  Phe  Glu  Phe  Asn  Pro  Glu  Asp  Pro
               380                     385                     390

Ile  Pro  Asp  Thr  Asn  Ser  Thr  Ser  Gly  Asp  Pro  Val  Glu  Lys  Lys
               395                     400                     405

Asp  Glu  Thr  Pro  Phe  Gly  Val  Ser  Val  Ala  Val  Gly  Leu  Ala  Val
               410                     415                     420

Phe  Ala  Cys  Leu  Phe  Leu  Ser  Thr  Leu  Leu  Leu  Val  Leu  Asn  Lys
               425                     430                     435

Cys  Gly  Arg  Arg  Asn  Lys  Phe  Gly  Ile  Asn  Arg  Pro  Ala  Val  Leu
               440                     445                     450

Ala  Pro  Glu  Asp  Gly  Leu  Ala  Met  Ser  Leu  His  Phe  Met  Thr  Leu
               455                     460                     465

Gly  Gly  Ser  Ser  Leu  Ser  Pro  Thr  Glu  Gly  Lys  Gly  Ser  Gly  Leu
               470                     475                     480

Gln  Gly  His  Ile  Ile  Glu  Asn  Pro  Gln  Tyr  Phe  Ser  Asp  Ala  Cys
               485                     490                     495

Val  His  His  Ile  Lys  Arg  Arg  Asp  Ile  Val  Leu  Lys  Trp  Glu  Leu
               500                     505                     510

Gly  Glu  Gly  Ala  Phe  Gly  Lys  Val  Phe  Leu  Ala  Glu  Cys  His  Asn
               515                     520                     525

Leu  Leu  Pro  Glu  Gln  Asp  Lys  Met  Leu  Val  Ala  Val  Lys  Ala  Leu
               530                     535                     540

Lys  Glu  Ala  Ser  Glu  Ser  Ala  Arg  Gln  Asp  Phe  Gln  Arg  Glu  Ala
               545                     550                     555

Glu  Leu  Leu  Thr  Met  Leu  Gln  His  Gln  His  Ile  Val  Arg  Phe  Phe
               560                     565                     570

Gly  Val  Cys  Thr  Glu  Gly  Arg  Pro  Leu  Leu  Met  Val  Phe  Glu  Tyr
               575                     580                     585

Met  Arg  His  Gly  Asp  Leu  Asn  Arg  Phe  Leu  Arg  Ser  His  Gly  Pro
               590                     595                     600

Asp  Ala  Lys  Leu  Leu  Ala  Gly  Gly  Glu  Asp  Val  Ala  Pro  Gly  Pro
               605                     610                     615

Leu  Gly  Leu  Gly  Gln  Leu  Leu  Ala  Val  Ala  Ser  Gln  Val  Ala  Ala
               620                     625                     630

Gly  Met  Val  Tyr  Leu  Ala  Gly  Leu  His  Phe  Val  His  Arg  Asp  Leu
               635                     640                     645

Ala  Thr  Arg  Asn  Cys  Leu  Val  Gly  Gln  Gly  Leu  Val  Val  Lys  Ile
               650                     655                     660

Gly  Asp  Phe  Gly  Met  Ser  Arg  Asp  Ile  Tyr  Ser  Thr  Asp  Tyr  Tyr
               665                     670                     675

Arg  Val  Gly  Gly  Arg  Thr  Met  Leu  Pro  Ile  Arg  Trp  Met  Pro  Pro
               680                     685                     690

Glu  Ser  Ile  Leu  Tyr  Arg  Lys  Phe  Thr  Thr  Glu  Ser  Asp  Val  Trp
               695                     700                     705

Ser  Phe  Gly  Val  Val  Leu  Trp  Glu  Ile  Phe  Thr  Tyr  Gly  Lys  Gln
               710                     715                     720

Pro  Trp  Tyr  Gln  Leu  Ser  Asn  Thr  Glu  Ala  Ile  Asp  Cys  Ile  Thr
               725                     730                     735

Gln  Gly  Arg  Glu  Leu  Glu  Arg  Pro  Arg  Ala  Cys  Pro  Pro  Glu  Val
               740                     745                     750

Tyr  Ala  Ile  Met  Arg  Gly  Cys  Trp  Gln  Arg  Glu  Pro  Gln  Gln  Arg
               755                     760                     765

His  Ser  Ile  Lys  Asp  Val  His  Ala  Arg  Leu  Gln  Ala  Leu  Ala  Gln
               770                     775                     780
```

Ala Pro Pro Val Tyr Leu Asp Val Leu Gly
                785                     790

( 2 ) INFORMATION FOR SEQ ID NO:10:

( i ) SEQUENCE CHARACTERISTICS:
           ( A ) LENGTH: 23 base pairs
           ( B ) TYPE: Nucleic Acid
           ( C ) STRANDEDNESS: Single
           ( D ) TOPOLOGY: Linear ( x i ) SEQUENCE DESCRIPTION: SEQ ID NO:10:

TGYGAYATHA TGTGGYTNAA RAC               23

( 2 ) INFORMATION FOR SEQ ID NO:11:

( i ) SEQUENCE CHARACTERISTICS:
           ( A ) LENGTH: 23 base pairs
           ( B ) TYPE: Nucleic Acid
           ( C ) STRANDEDNESS: Single
           ( D ) TOPOLOGY: Linear ( x i ) SEQUENCE DESCRIPTION: SEQ ID NO:11:

TGGATGCARY TNTGGCARCA RCA               23

( 2 ) INFORMATION FOR SEQ ID NO:12:

( i ) SEQUENCE CHARACTERISTICS:
           ( A ) LENGTH: 21 base pairs
           ( B ) TYPE: Nucleic Acid
           ( C ) STRANDEDNESS: Single
           ( D ) TOPOLOGY: Linear ( x i ) SEQUENCE DESCRIPTION: SEQ ID NO:12:

YTCRTCYTTN CCRTAYTCRT T                 21

( 2 ) INFORMATION FOR SEQ ID NO:13:

( i ) SEQUENCE CHARACTERISTICS:
           ( A ) LENGTH: 23 base pairs
           ( B ) TYPE: Nucleic Acid
           ( C ) STRANDEDNESS: Single
           ( D ) TOPOLOGY: Linear ( x i ) SEQUENCE DESCRIPTION: SEQ ID NO:13:

CCYTCYTGRT ARTAYTCNAC GTG               23

( 2 ) INFORMATION FOR SEQ ID NO:14:

( i ) SEQUENCE CHARACTERISTICS:
           ( A ) LENGTH: 22 base pairs
           ( B ) TYPE: Nucleic Acid
           ( C ) STRANDEDNESS: Single
           ( D ) TOPOLOGY: Linear ( x i ) SEQUENCE DESCRIPTION: SEQ ID NO:14:

CACGTCAACA ACGGCAACTA CA                22

( 2 ) INFORMATION FOR SEQ ID NO:15:

( i ) SEQUENCE CHARACTERISTICS:
           ( A ) LENGTH: 25 base pairs
           ( B ) TYPE: Nucleic Acid
           ( C ) STRANDEDNESS: Single
           ( D ) TOPOLOGY: Linear ( x i ) SEQUENCE DESCRIPTION: SEQ ID NO:15:

GGAAGGATGA GAAACAGATT TCTGC                                                                                              25

(2) INFORMATION FOR SEQ ID NO:16:

(i) SEQUENCE CHARACTERISTICS:
        (A) LENGTH: 23 base pairs
        (B) TYPE: Nucleic Acid
        (C) STRANDEDNESS: Single
        (D) TOPOLOGY: Linear (xi) SEQUENCE DESCRIPTION: SEQ ID NO:16:

CATCAATGGC CACTTCCTCA AGG                                                                                                23

(2) INFORMATION FOR SEQ ID NO:17:

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (xi) SEQUENCE DESCRIPTION: SEQ ID NO:17:

AGGTGTTTCG TCCTTCTTCT CC                                                                                                 22

(2) INFORMATION FOR SEQ ID NO:18:

(i) SEQUENCE CHARACTERISTICS:
        (A) LENGTH: 24 base pairs
        (B) TYPE: Nucleic Acid
        (C) STRANDEDNESS: Single
        (D) TOPOLOGY: Linear (xi) SEQUENCE DESCRIPTION: SEQ ID NO:18:

GAGATGTGCC CGACCGGTTG TATC                                                                                               24

(2) INFORMATION FOR SEQ ID NO:19:

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (xi) SEQUENCE DESCRIPTION: SEQ ID NO:19:

CACAGTGATA GGAGGTGTGG GA                                                                                                 22

(2) INFORMATION FOR SEQ ID NO:20:

(i) SEQUENCE CHARACTERISTICS:
        (A) LENGTH: 19 base pairs
        (B) TYPE: Nucleic Acid
        (C) STRANDEDNESS: Single
        (D) TOPOLOGY: Linear (xi) SEQUENCE DESCRIPTION: SEQ ID NO:20:

GGATGTGGCT CCAGGCCCC                                                                                                     19

(2) INFORMATION FOR SEQ ID NO:21:

(i) SEQUENCE CHARACTERISTICS:
        (A) LENGTH: 19 base pairs
        (B) TYPE: Nucleic Acid
        (C) STRANDEDNESS: Single
        (D) TOPOLOGY: Linear (xi) SEQUENCE DESCRIPTION: SEQ ID NO:21:

GGGCAACCCG CCCACGGAA                                                                                                     19

( 2 ) INFORMATION FOR SEQ ID NO:22:

( i ) SEQUENCE CHARACTERISTICS:
        ( A ) LENGTH: 19 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:22:

ACGCCAGGCC AAGGGTGAG                                              19

( 2 ) INFORMATION FOR SEQ ID NO:23:

( i ) SEQUENCE CHARACTERISTICS:
        ( A ) LENGTH: 20 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:23:

TAACCACTCC CAGCCCCTGG                                           20

( 2 ) INFORMATION FOR SEQ ID NO:24:

( i ) SEQUENCE CHARACTERISTICS:
        ( A ) LENGTH: 20 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:24:

TTGGTGGCCT CCAGCGGCAG 20

( 2 ) INFORMATION FOR SEQ ID NO:25:

( i ) SEQUENCE CHARACTERISTICS:
        ( A ) LENGTH: 22 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:25:

AATTCATGAC CACCAGCCAC CA                                        22

( 2 ) INFORMATION FOR SEQ ID NO:26:

( i ) SEQUENCE CHARACTERISTICS:
        ( A ) LENGTH: 20 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:26:

GCTCCTCGGG ACTGCGATGC                                           20

( 2 ) INFORMATION FOR SEQ ID NO:27:

( i ) SEQUENCE CHARACTERISTICS:
        ( A ) LENGTH: 24 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:27:

ATGTCGCCCT GGCCGAGGTG GCAT                                    24

( 2 ) INFORMATION FOR SEQ ID NO:28:

(i) SEQUENCE CHARACTERISTICS:
  (A) LENGTH: 21 base pairs
  (B) TYPE: Nucleic Acid
  (C) STRANDEDNESS: Single
  (D) TOPOLOGY: Linear (xi) SEQUENCE DESCRIPTION: SEQ ID NO:28:

AAGCTCAACA GCCAGAACCT C        21

(2) INFORMATION FOR SEQ ID NO:29:

(i) SEQUENCE CHARACTERISTICS:
  (A) LENGTH: 21 base pairs
  (B) TYPE: Nucleic Acid
  (C) STRANDEDNESS: Single
  (D) TOPOLOGY: Linear (xi) SEQUENCE DESCRIPTION: SEQ ID NO:29:

CAGCTCTGTG AGGATCCAGC C        21

(2) INFORMATION FOR SEQ ID NO:30:

(i) SEQUENCE CHARACTERISTICS:
  (A) LENGTH: 21 base pairs
  (B) TYPE: Nucleic Acid
  (C) STRANDEDNESS: Single
  (D) TOPOLOGY: Linear (xi) SEQUENCE DESCRIPTION: SEQ ID NO:30:

CCGACCGGTT TTATCAGTGA C        21

(2) INFORMATION FOR SEQ ID NO:31:

(i) SEQUENCE CHARACTERISTICS:
  (A) LENGTH: 23 base pairs
  (B) TYPE: Nucleic Acid
  (C) STRANDEDNESS: Single
  (D) TOPOLOGY: Linear (xi) SEQUENCE DESCRIPTION: SEQ ID NO:31:

ATGATCTTGG ACTCCCGCAG AGG      23

(2) INFORMATION FOR SEQ ID NO:32:

(i) SEQUENCE CHARACTERISTICS:
  (A) LENGTH: 21 base pairs
  (B) TYPE: Nucleic Acid
  (C) STRANDEDNESS: Single
  (D) TOPOLOGY: Linear (xi) SEQUENCE DESCRIPTION: SEQ ID NO:32:

CTTGGCCAAG GCATCTCCGG T        21

(2) INFORMATION FOR SEQ ID NO:33:

(i) SEQUENCE CHARACTERISTICS:
  (A) LENGTH: 21 base pairs
  (B) TYPE: Nucleic Acid
  (C) STRANDEDNESS: Single
  (D) TOPOLOGY: Linear (xi) SEQUENCE DESCRIPTION: SEQ ID NO:33:

ATGTGCAGCA CATTAAGAGG A        21

(2) INFORMATION FOR SEQ ID NO:34:

(i) SEQUENCE CHARACTERISTICS:

(A) LENGTH: 24 base pairs
        (B) TYPE: Nucleic Acid
        (C) STRANDEDNESS: Single
        (D) TOPOLOGY: Linear (xi) SEQUENCE DESCRIPTION: SEQ ID NO:34:

TTATACACAG GCTTAAGCCA TCCA                                                      24

(2) INFORMATION FOR SEQ ID NO:35:

(i) SEQUENCE CHARACTERISTICS:
        (A) LENGTH: 19 base pairs
        (B) TYPE: Nucleic Acid
        (C) STRANDEDNESS: Single
        (D) TOPOLOGY: Linear (xi) SEQUENCE DESCRIPTION: SEQ ID NO:35:

AGGAGGCATC CAGCGAATG                                                            19

(2) INFORMATION FOR SEQ ID NO:36:

(i) SEQUENCE CHARACTERISTICS:
        (A) LENGTH: 9 amino acids
        (B) TYPE: Amino Acid
        (D) TOPOLOGY: Linear (xi) SEQUENCE DESCRIPTION: SEQ ID NO:36:

Glu  Ser  Thr  Asp  Asn  Phe  Ile  Leu  Phe
 1                    5                    9

(2) INFORMATION FOR SEQ ID NO:37:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO:37:

Leu  Phe  Asn  Pro  Ser  Gly  Asn  Asp  Phe  Cys  Ile  Trp  Cys  Glu
 1                    5                         10                   14

(2) INFORMATION FOR SEQ ID NO:38:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:38:

TCTCCTTCTC GCCGGTGG                                                             18

(2) INFORMATION FOR SEQ ID NO:39:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:39:

Ser  Pro  Ser  Arg  Arg  Trp
 1                    5    6

(2) INFORMATION FOR SEQ ID NO:40:

(i) SEQUENCE CHARACTERISTICS:
        (A) LENGTH: 11 amino acids
        (B) TYPE: Amino Acid (D) TOPOLOGY: Linear (xi) SEQUENCE DESCRIPTION: SEQ ID NO:40:

```
Phe Val Leu Phe His Lys Ile Pro Leu Asp Gly
 1               5                   10  11
```

(2) INFORMATION FOR SEQ ID NO:41:

(i) SEQUENCE CHARACTERISTICS:
        (A) LENGTH: 84 amino acids
        (B) TYPE: Amino Acid
        (D) TOPOLOGY: Linear (xi) SEQUENCE DESCRIPTION: SEQ ID NO:41:

```
Trp Val Phe Ser Asn Ile Asp Asn His Gly Ile Leu Asn Leu Lys
 1               5                   10                  15
Asp Asn Arg Asp His Leu Val Pro Ser Thr His Tyr Ile Tyr Glu
                20                   25                  30
Glu Pro Glu Val Gln Ser Gly Glu Val Ser Tyr Pro Arg Ser His
                35                   40                  45
Gly Phe Arg Glu Ile Met Leu Asn Pro Ile Ser Leu Pro Gly His
                50                   55                  60
Ser Lys Pro Leu Asn His Gly Ile Tyr Val Glu Asp Val Asn Val
                65                   70                  75
Tyr Phe Ser Lys Gly Arg His Gly Phe
                80            84
```

We claim:

1. An isolated nucleic acid molecule comprising a nucleotide sequence encoding a chimeric polypeptide comprising an immunoglobulin constant domain sequence fused to a neurotrophin-binding polypeptide sequence comprising a second immunoglobulin-like domain sequence of human trkA, human trkB, or human trkC, wherein the chimeric polypeptide binds a neurotrophin that binds human trkA, human trkB, or human trkC.

2. An expression vector comprising the nucleic acid molecule of claim 1 operably linked to control sequences recognized by a host cell transformed with the vector.

3. A host cell transformed with the vector of claim 2.

4. The nucleic acid molecule of claim 1, wherein the second immunoglobulin-like domain sequence is that in human trkA.

5. The nucleic acid molecule of claim 1, wherein the second immunoglobulin-like domain sequence is encoded by SEQ ID NO: 1 or encoded by SEQ ID NO: 5.

6. The nucleic acid molecule of claim 1, wherein the neurotrophin-binding polypeptide sequence comprises an extracellular domain of human trkA, human trkB, or human trkC.

7. The nucleic acid molecule of claim 6, wherein the extracellular domain has amino acids 36 to 402, inclusive, of human trkA SEQ ID NO: 9.

8. The nucleic acid molecule of claim 6, wherein the extracellular domain has amino acids 32 to 430, inclusive, of the amino acid sequence encoded by SEQ ID NO: 1 or amino acids 32 to 429, inclusive, of the amino acid sequence encoded by SEQ ID NO: 5 with a deletion of amino acids ESTDNFILF (SEQ ID NO: 36) at amino acid positions 402 to 410.

9. The nucleic acid molecule of claim 8, wherein the extracellular domain has amino acids 32 to 429, inclusive, of the amino acid sequence encoded by SEQ ID NO: 5.

10. The nucleic acid molecule of claim 6, wherein the neurotrophin-binding polypeptide sequence comprises amino acids 36 to 790, inclusive, of human trkA SEQ ID NO 9 with amino acid residues 410 to 433 deleted.

11. The nucleic acid molecule of claim 6, wherein the neurotrophin-binding polypeptide sequence comprises amino acids 32 to 822, inclusive, of the amino acid sequence encoded by SEQ. ID. NO: 1, with amino acid residues 430 to 454, deleted.

12. The nucleic acid molecule of claim 11, wherein amino acid residues corresponding to 457 to 822, inclusive, of the amino acid sequence encoded by SEQ ID NO: 1 are replaced by the amino acid sequence FVLFHKIPLDG (SEQ ID NO: 40).

13. The nucleic acid molecule of claim 6, wherein the neurotrophin-binding polypeptide sequence comprises amino acids 32 to 839, inclusive, of the amino acid sequence encoded by SEQ. ID. NO: 5, with amino acid residues 430 to 453 deleted.

14. The nucleic acid molecule of claim 13, wherein amino acid residues corresponding to 529 to 839, inclusive, of the amino acid sequence encoded by SEQ ID NO: 5 are replaced by the amino acid sequence encoded by SEQ ID NO: 41.

15. The nucleic acid molecule of claim 1, wherein the immunoglobulin constant domain sequence is an immunoglobulin Fc domain sequence.

16. The nucleic acid molecule of claim 15, wherein the Fc domain sequence is that of an human IgG heavy chain.

17. The host cell of claim 3, that is a eucaryotic cell.

18. The host cell of claim 17 that is a mammalian cell.

* * * * *

UNITED STATES PATENT AND TRADEMARK OFFICE
CERTIFICATE OF CORRECTION

| | | |
|---|---|---|
| PATENT NO. | : 5,877,016 | |
| APPLICATION NO. | : 08/286846 | |
| DATED | : March 2, 1999 | |
| INVENTOR(S) | : Leonard G. Presta et al. | |

It is certified that error appears in the above-identified patent and that said Letters Patent is hereby corrected as shown below:

Col. 82, line 10, please change the residue at position 1849 of SEQ ID NO: 7 from "C" to "T". The change has been incorporated below.

ATCTATGTTG AGGATGTCAA TGTTTATTTC AGCAAAGGAC GTCATGGC<u>T</u>T   1850

Signed and Sealed this
Eighth Day of March, 2011

David J. Kappos
*Director of the United States Patent and Trademark Office*